(12) United States Patent
Goldsmith et al.

(10) Patent No.: US 12,420,014 B2
(45) Date of Patent: Sep. 23, 2025

(54) DOSING OF INCRETIN PATHWAY DRUGS

(71) Applicant: Closed Loop Medicine Ltd., Cambridge (GB)

(72) Inventors: Paul Goldsmith, London (GB); David Bruce Campbell, London (GB); Michael Catt, Wellingborough (GB); Tom Godec, London (GB); Joe Coghlin, London (GB)

(73) Assignee: CLOSED LOOP MEDICINE LTD., Cambridge (GB)

( * ) Notice: Subject to any disclaimer, the term of this patent is extended or adjusted under 35 U.S.C. 154(b) by 0 days.

(21) Appl. No.: 18/968,283

(22) Filed: Dec. 4, 2024

(65) Prior Publication Data
US 2025/0090755 A1    Mar. 20, 2025

Related U.S. Application Data

(63) Continuation-in-part of application No. 18/734,284, filed on Jun. 5, 2024.

(30) Foreign Application Priority Data

Jun. 5, 2023  (GB) .................................. 2308359
Jun. 5, 2023  (GB) .................................. 2308362
(Continued)

(51) Int. Cl.
*A61M 5/172* (2006.01)
*A61K 38/23* (2006.01)
*A61K 38/26* (2006.01)

(52) U.S. Cl.
CPC ........... *A61M 5/1723* (2013.01); *A61K 38/23* (2013.01); *A61K 38/26* (2013.01)

(58) Field of Classification Search
None
See application file for complete search history.

(56) References Cited

U.S. PATENT DOCUMENTS 5,605,911 A    2/1997  Olney
5,629,336 A    5/1997  Hutson
(Continued)

FOREIGN PATENT DOCUMENTS

CA    3 220 596 A1    11/2022
JP    2005-511615 A    4/2005
(Continued)

OTHER PUBLICATIONS

Obesity Care, Novo Nordisk, CMD22 Capital Markets Day Conference, date: Mar. 3, 2022. (Year: 2022).*
(Continued)

*Primary Examiner* — Manuel A Mendez
(74) *Attorney, Agent, or Firm* — SQUIRE PATTON BOGGS (US) LLP

(57) ABSTRACT

A method for administering a dosage of Cagrisema to a patient for the treatment of obesity, the method comprising: administering a dosage of Cagrisema to the patient, wherein the dosage of Cagrisema is determined by: receiving patient data relating to a patient, wherein the patient data includes patient weight data; and processing the patient data including the patient weight data with a dosage calculator to determine the dosage of Cagrisema for administering to the patient wherein the dosage calculator is derived from a pharmacokinetic, PK, model.

24 Claims, 26 Drawing Sheets

(30) Foreign Application Priority Data

Jun. 5, 2023 (GB) .................................... 2308365
Jun. 5, 2024 (WO) ............... PCT/GB2024/051450

(56) References Cited

U.S. PATENT DOCUMENTS

| | | | |
|---|---|---|---|
| 8,992,464 | B2 | 3/2015 | Bashan et al. |
| 10,231,664 | B2 | 3/2019 | Ganesh |
| 2003/0028031 | A1 | 2/2003 | Xitian |
| 2005/0023291 | A1 | 2/2005 | Hynes et al. |
| 2006/0100667 | A1 | 5/2006 | Machado et al. |
| 2007/0049576 | A1 | 3/2007 | Barlow et al. |
| 2007/0150026 | A1 | 6/2007 | Bourget et al. |
| 2007/0292883 | A1 | 12/2007 | Ossovskaya et al. |
| 2008/0275309 | A1 | 11/2008 | Stivoric et al. |
| 2008/0288023 | A1 | 11/2008 | John |
| 2010/0073170 | A1 | 3/2010 | Siejko et al. |
| 2010/0235178 | A1 | 9/2010 | Firminger et al. |
| 2010/0235195 | A1 | 9/2010 | Firminger et al. |
| 2012/0108984 | A1 | 5/2012 | Bennett et al. |
| 2012/0116194 | A1 | 5/2012 | Gross et al. |
| 2012/0203573 | A1* | 8/2012 | Mayer ............. G16H 20/13 705/3 |
| 2014/0310025 | A1 | 10/2014 | Sayada et al. |
| 2014/0323536 | A1 | 10/2014 | Sabovic |
| 2015/0133886 | A1 | 5/2015 | Morris et al. |
| 2016/0175310 | A1 | 6/2016 | Castelleno |
| 2016/0224760 | A1 | 8/2016 | Petak et al. |
| 2016/0350509 | A1 | 12/2016 | Sharma |
| 2018/0140835 | A1 | 5/2018 | Sharma |
| 2019/0121935 | A1 | 4/2019 | Ho et al. |
| 2019/0367903 | A1 | 12/2019 | Domenyuk |
| 2020/0321096 | A1 | 10/2020 | Mould |
| 2020/0350073 | A1 | 11/2020 | Goldsmith et al. |
| 2021/0106592 | A1 | 4/2021 | Mehra |
| 2021/0259993 | A1 | 8/2021 | Witkin et al. |

FOREIGN PATENT DOCUMENTS

| | | |
|---|---|---|
| JP | 2010-533927 A | 10/2010 |
| JP | 2013-157026 A | 8/2013 |
| JP | 2013-182493 A | 9/2013 |
| JP | 2016-221056 A | 12/2016 |
| JP | 2018-514026 A | 5/2018 |
| JP | 2019-504402 A | 2/2019 |
| WO | WO 2001/061616 A2 | 8/2001 |
| WO | WO 2005/023291 A2 | 3/2005 |
| WO | WO 2008/077092 A2 | 6/2008 |
| WO | WO 2012/089318 A1 | 7/2012 |
| WO | WO 2016/149529 A1 | 9/2016 |
| WO | WO 2017/214630 A1 | 12/2017 |
| WO | WO 2017/220734 A1 | 12/2017 |
| WO | WO 2018/020239 A1 | 2/2018 |
| WO | WO 2018/049250 A1 | 3/2018 |
| WO | WO 2019/008571 A1 | 1/2019 |
| WO | WO 2019/027003 A1 | 2/2019 |
| WO | WO 2020/221993 A1 | 11/2020 |
| WO | WO 2021/097653 A | 5/2021 |

OTHER PUBLICATIONS

Rune Overgaard et al., "Clinical Pharmacokinetics of Oral Semaglutide: Analyses of Data from Clinical Pharmacology Trials," Clinical Pharmacokinetics, 2021, vol. 60, pp. 1335-1348.

Daniel R. Quast et al., "Macronutrient intake, appetite, food preferences and exocrine pancreas function after treatment with short- and long-acting glucagon-like peptide-1 receptor agonists in type 2 diabetes," Diabetes, Obesity and Metabolism, 2021, vol. 23, pp. 2344-2353.

Diana M. Isaacs et al., "Optimizing Therapeutic Outcomes With Oral Semaglutide: A Patient-Centered Approach," Diabetes Spectrum, 2021, vol. 34, No. 1, pp. 7-19.

Hae Jin Kim, "Recent Updates on Glucagon-Like Peptide 1 Receptor Agonist," The Journal of Korean Diabetes, 2021, vol. 22, No. 2, pp. 126-133.

Jaime P. Almandoz et al., "Switching Between Glucagon-Like Peptide-1 Receptor Agonists: Rationale and Practical Guidance," Clinical Diabetes Journal, 2020, vol. 38, No. 4, pp. 390-402.

Lene Jensen et al., "Absorption, metabolism and excretion of the GLP-1 analogue semaglutide in humans and nonclinical species," European Journal of Pharmaceutical Sciences, 2017, vol. 104, pp. 31-41.

Lene Jensen et al., "Pharmacokinetics and tolerability of semaglutide in people with hepatic impairment," Diabetes Obesity and Metabolism, 2018, vol. 20, pp. 998-1005.

Malik Elharram et al., "Novel glucose lowering agents are associated with a lower risk of cardiovascular and adverse events in type 2 diabetes: A population based analysis," International Journal of Cardiology, 2020, vol. 310, pp. 147-154.

Rune Overgaard et al., "Population Pharmacokinetics of Semaglutide for Type 2 Diabetes," Diabetes Therapy, 2019, vol. 10, pp. 649-662.

Kirstin Cecilie Carlsson Petri et al., "Semaglutide s.c. Once-Weekly in Type 2 Diabetes: A Population Pharmacokinetic Analysis," Diabetes Therapy, 2018, vol. 9, pp. 1533-1547.

Rybelsus (semaglutide) tablets, for oral use, Prescribing Information, Initial U.S. Approval: 2017.

Center for Drug Evaluation and Research, Clinical Review(s), Novo Nordisk, Rybelsus FDA Application No. 213051Orig1s000, 2019.

Ozempic (semaglutide) injection, for subcutaneous use, Prescribing Information, Initial U.S. Approval: 2017.

Center for Drug Evaluation and Research, Clinical Pharmacology Biopharmaceutics Review(s), Novo Nordisk Inc., Ozempic FDA Application No. 209637Orig1s000, 2016.

Ozempic, European Medicines Agency, European Public Assessment Report, 2017.

Dilip Sharma et al., "Recent updates on GLP-1 agonists: Current advancements & challenges," Biomedicine & Pharmacotherapy, 2018, vol. 108, pp. 952-962.

Stephen A. Brunton et al., "GLP-1 receptor agonists in the treatment of type 2 diabetes: role and clinical experience to date," Postgraduate Medicine, 2020, vol. 132, No. S2, pp. 3-14.

Center for Drug Evaluation and Research, Other Review(s), Review of Patient Labeling: Medication Guide (MG) and Instructions for Use (IFU), Novo Nordisk Inc., Wegovy FDA Application No. 215256Orig1s000, 2021.

Center for Drug Evaluation and Research, Clinical Review(s), Novo Nordisk, Wegovy FDA Application No. 215256Orig1s000, 2021.

William H. Polonsky et al., "Higher Rates of Persistence and Adherence in Patients with Type 2 Diabetes Initiating Once-Weekly vs Daily Injectable Glucagon-Like Peptide-1 Receptor Agonists in US Clinical Practice (STAY Study)," Diabetes Therapy, 2022, vol. 13, pp. 175-187.

Amartya Mukhopadhyay et al., "Personalised Dosing Using the curate.ai Algorithm: Protocol for a Feasibility Study in Patients with Hypertension and Type II Diabetes Mellitus," International Journal of Environment Research and Public Health, 2022, vol. 19, No. 8979, pp. 1-11.

Center for Drug Evaluation and Research, Clinical Review(s), Eli Lilly and Company (Lilly), Mounjaro FDA Application No. 215866Orig1s000, 2022.

Mariana Lenharo, "What Scientists are Learning About Potent New Obesity Drugs," 2023, Nature, vol. 618, pp. 17-18.

Miriam E. Tucker, "If at First Tirzepatide Doesn't Succeed, Keep Trying," Medscape Medical News, 2024, accessed at https://www.medscape.com/viewarticle/if-first-tirzepatide-doesnt-succeed-keep-trying-2024a100090d?form=fpf.

Center for Drug Evaluation and Research, Clinical Pharmacology Review(s), Eli Lilly and Company, Mounjaro FDA Application No. 215866Orig1s000, 2021.

Corey Gerving et al., "Predicting Energy Intake in Adults who are Dieting and Exercising," International Journal of Obesity, 2022, vol. 46, No. 12, pp. 2095-2101.

Sarayut Janmahasatian et al., "Quantification of Lean Bodyweight," Clin Pharmacokinet, 2005, vol. 44, No. 10, pp. 1051-1065.

(56) References Cited

OTHER PUBLICATIONS

Timo D. Müller et al., "Anti-obesity drug discovery: advances and challenges," Nature Reviews Drug Discovery, 2022, vol. 21, pp. 201-223.
Sadjad Anzabi Zadeh et al., "Optimizing Warfarin Dosing using Deep Reinforcement Learning," Journal of Biomedical Informatics, 2022, pp. 1-32.
Wegovy (semaglutide) injection, for subcutaneous use, Prescribing Information, Initial U.S. Approval: 2017.
Final Office Action mailed Jul. 20, 2022, in U.S. Appl. No. 16/860,665, 43 pages.
International Search Report and Written Opinion mailed Aug. 20, 2020 in International Patent Application No. PCT/GB2020/051027, 20pgs.
Dimitris Bertsimas et al., "Personalized Diabetes Management Using Electronic Medical Records," Diabetes Care, 2017, vol. 40, pp. 210-217.
Kelly Glazer Baron et al., "Next Steps for Patients Who Fail to Respond to Cognitive Behavioral Therapy for Insomnia (CBT-I): the Perspective from Behavioral Sleep Medicine Psychologists," Curr Sleep Medicine Rep., 2017, vol. 3, pp. 327-332.
Muxuan Liang et al., "Estimating individualized optimal combination therapies through outcome weighted deep learning algorithms," Statistics in Medicine, 2018, vol. 37, pp. 3869-3886.
Wolfgang Linden et al., "Clinical Effectiveness of Non-Drug Treatment for Hypertension: a Meta-Analysis," Annals of Behavioral Medicine, 1994, vol. 16, Issue 1, pp. 35-45, https://doi.org/10.1093/abm/16.1.35.
Office Action issued in corresponding Japanese Patent Application No. 2021-565715 dated May 21, 2024, with English language machine-translation thereof.
Examination Report issued in corresponding Indian Patent Application No. 202117051464 dated May 1, 2024.
LB Enebo et al., "Safety, tolerability, pharmacokinetics, and pharmacodynamics of concomitant administration of multiple doses of cagrilintide with semaglutide 2.4 mg for weight management: a randomised, controlled, phase 1b trial," Lancet, May 8, 2021, vol. 397, pp. 1736-1748.

\* cited by examiner

A

B

C

DOSING OF INCRETIN PATHWAY DRUGS

CROSS-REFERENCE TO RELATED APPLICATIONS

The present application is a continuation in part of U.S. patent application Ser. No. 18/734,284, filed on Jun. 5, 2024, which claims priority to GB Patent Application Nos. 2308362.9, 2308365.2, and 2308359.5 each filed on Jun. 5, 2023, and PCT International Patent Application No. PCT/GB2024/051450, filed on Jun. 5, 2024. The present application incorporates all of these referenced applications by reference in their entirety.

FIELD

The present disclosure relates to systems and methods for determining a dosage of an incretin pathway drug, such as Cagrisema, for administering to a patient.

BACKGROUND

The natural GLP1 (Glucagon-like peptide-1) hormone suppresses appetite and increases satiety. GLP1 slows gastric emptying and may additionally contribute to satiation via increased thermogenesis.

GLP1 agonists (Glucagon-like peptide-1 receptor agonists) are a synthetic analogue derivative of the natural GLP1 hormone which have been modified to increase stability in the human body. GLP1 agonists, such as Semaglutide, may be provided with drug label instructions having a substantially fixed dosing regimen (only providing flexibility if side effects are experienced) which advises use in combination with multidisciplinary dietary advice, including from a dietitian. These nondrug therapies are delivered as a standalone treatment independent of the drug dosage regimen (e.g. face to face therapy, written dietary instructions or a separate diet app).

SUMMARY

According to a first aspect of the present disclosure there is provided a computer implemented method for determining a dosage of an incretin pathway drug for administering to a patient for the treatment of obesity, the method comprising:
receiving patient data relating to a patient, wherein the patient data includes patient weight data;
processing the patient data with a dosage calculator to determine the dosage of the incretin pathway drug for administering to the patient; and
indicating the dosage.

The incretin pathway drug may comprise semaglutide.
The incretin pathway drug may comprise a GIP agonist or a dual GLP1/GIP agonist.
The incretin pathway drug may comprise tirzepatide.
The incretin pathway drug may comprise Cagrisema (cagrilintide and semaglutide coformulation).
The incretin pathway drug may comprise a GLP-1 receptor agonist. The incretin pathway drug may comprise one of: albiglutide, dulaglutide, exenatide, liraglutide, efpeglenatide (also called langlenatide) or lixisenatide. The incretin pathway drug may comprise one of: beinaglutide or ecnoglutide. The incretin pathway drug may comprise an oxyntomodulin analogue such as DA-1726.
The incretin pathway drug may comprise a GLP-1 and glucagon receptor co-agonist. The incretin pathway drug may comprise one of: bamadutide, cotadutide, pegapamodutide, pemvidutide, or survodutide. The incretin pathway drug may comprise a GLP-1/GCCR/GIP triple agonist such as retatrutide.

The incretin pathway drug may include: maridebart cafraglutide (Maritide), cagrilintide/semaglutide (Cagrisema), pemvidutide, mazdutide or efinopegdutide. The incretin pathway drug may comprise a GLP-1, GCCR and/or GIP drug in development including: Orforglipron, CT-388, CT-868, GX-G6, GMA 105, HM11260C, Danuglipron, GSBR-1290, Pegapamodutide, VK-2735, Dapiglutide, AMG-786, ECC5004, YH 25724, CT-996, DD-01, UBT251, HM15136, HDM1002, NNC-9204-1706, PB-119, SAR425899 [68Ga] Ga-DO3A-VS-Cys40-Tuna-2, XW 014, XW-004, TAK-094, GMA-106, Utreglutide, TERN 601 or DR-10624.

The dosage calculator may be derived from a pharmacokinetic, PK, model.
The PK model may comprise a personalised energy intake—total daily energy expenditure model.
The method may comprise processing the patient data with the dosage calculator to determine an initial dosage for administering to the patient and indicating the initial dosage.
Processing the patient data with the dosage calculator to determine an initial dosage may comprise:
determining a target end point based on the patient data; and
determining the initial dosage based on the target end point.
The target end point may comprise one or more of: a target weight loss; and a target side effect level.
The method may comprise:
determining a target plasma level based on the target end point; and
determining an initial dosage based on the target plasma level and the target end point.
The patient weight data may include an initial weight and a target weight. The method may comprise processing the initial weight and the target weight with the dosage calculator to determine the initial dosage.
Processing the initial weight and the target weight with the dosage calculator to determine the dosage may comprise:
setting a target drug concentration based on the initial weight and the target weight; and
determining the initial dosage based on the target drug concentration and the initial weight.
The target drug concentration may comprise: a target drug plasma level, a target whole blood drug level or a target drug serum level.
The incretin pathway drug may comprise semaglutide and the method may comprise:
setting a target drug concentration comprising a target plasma level from 50 nmol/L to 100 nmol/L; and
determining an initial dosage based on the target drug concentration and the initial weight.
The patient data may comprise one or more of: a patient age; a patient ethnicity; a patient gender; a patient diabetes history; a kidney function metric; a pharmacogenomic profile; a treatment purpose; an obesity type; a dosage route and a patient medication list.
The patient data further may comprise one or more of: a patient age; a patient ethnicity; a patient gender; a patient diabetes history; a kidney function metric; a treatment purpose; a dosage route; a pharmacogenomic profile and a patient medication list, and wherein the method the method may comprise determining the initial dosage based on the target drug concentration and the patient data.

The dosage route may comprise an oral dosage and the patient data may further comprise fasting time data and water intake data.

The dosage route may comprise a subcutaneous dosage and the patient data may further comprise an injection site.

The patient data may further comprise a patient side effect tolerance and the method may comprise processing the patient side effect tolerance with the dosage calculator to determine an initial dosage.

Processing the patient side effect tolerance with the dosage calculator may comprise:
  setting a target drug concentration based on the side effect tolerance; and
  determining the initial dosage based on the target drug concentration and the patient data.

The target drug concentration may comprise: a target drug plasma level, a target whole blood drug level and a target drug serum level.

The method may comprise:
  processing the patient side effect tolerance and the patient data with the dosage calculator to obtain a target drug concentration that satisfies the patient side effect tolerance; and
  processing the target drug concentration with the dosage calculator to determine the initial dosage.

The dosage calculator may comprise a side-effect calculator derived from a side effect model. The side effect model may comprise a discrete-time Markov side effect model or an Emax exposure response side effect model.

Processing the patient side effect tolerance and the patient data with the dosage calculator may comprise processing the patient side effect tolerance and the patient data with the side effect calculator. The side effect calculator may comprise a machine learning model. The machine learning model may have been trained using simulated population data generated by the discrete-time Markov side effect model or the Emax exposure response side effect model. The simulated population data may be generated by processing simulated patient data with the discrete-time Markov model or the Emax exposure side effect model. The simulated population data may be generated by processing the simulated patient data with the discrete-time Markov model at a plurality of times, and defining the simulated population data as summary metrics. The summary metrics may comprise one or more of: the mean number of adverse event occasions, the mean duration of each adverse event occasion, the mean time spent experiencing each adverse event, the mean time spent experiencing an adverse event of a given severity, the mean proportion of the entire treatment period spent experiencing each adverse event, and the mean proportion of the entire treatment period spent experiencing an adverse event of a given severity. The side effect tolerance may comprise one or more of: a gastro-intestinal side effect tolerance, a nausea side effect tolerance, a vomiting side effect tolerance; and a diarrhoea side effect tolerance.

Processing the patient side effect tolerance with the dosage calculator may comprise:
  determining a nominal initial dosage based on the patient data; and
  adjusting the nominal initial dosage based on the side effect tolerance.

The dosage may comprise an initial dosage and the method may comprise:
  determining one or more expectation trajectories based on the initial dosage, wherein the one or more expectation trajectories include:
    a dosage trajectory;
    a patient weight loss trajectory;
    an expected calorie intake trajectory; and
    a side effect trajectory.

The method may further comprise:
  receiving updated patient data including updated patient weight data; and
  processing the updated patient data with the dosage calculator to determine an updated dosage; and
  indicating the updated dosage.

Processing the updated patient data with the dosage calculator to determine an updated dosage may comprise one or more of:
  increasing the dosage if the updated weight data indicates a weight loss is less than a lower weight loss threshold; and
  reducing the dosage if the updated weight data indicates a weight loss greater than an upper weight loss threshold.

The dosage may comprise an initial dosage and the method may comprise determining a weight loss trajectory based on the initial dosage. The lower weight loss threshold and upper weight loss threshold may correspond to a prediction range of the weight loss trajectory.

The updated patient data may include patient satiety data. Processing the updated patient data with the dosage calculator to determine an updated dosage may comprise one or more of:
  reducing the dosage if the patient satiety data indicates a patient satiety greater than a first patient satiety threshold; and
  increasing the dosage if the patient satiety data indicates a patient satiety less than a second patient satiety threshold.

The patient satiety data may include a patient satiety score or a patient hunger score.

Indicating the updated dosage may comprise indicating the updated dosage if an elapsed time since a previous dose adjustment exceeds a drug effect time threshold.

The updated patient data may include reported side effect data. Processing the updated patient data with the dosage calculator to determine an updated dosage may comprise reducing the dosage if the reported side effect data satisfies one or more side effect severity thresholds.

The updated patient data may include reported side effect data and processing the updated patient data with the dosage calculator to determine an updated dosage may comprise reducing the dosage if the reported side effect data satisfies one or more side effect severity thresholds unless the reported side effect data indicates a patient willingness to proceed.

The updated patient data may include a patient metabolism metric from a physiological test result. The method may comprise updating the dosage calculator based on the patient metabolism metric.

The dosage calculator may be derived from a PK model comprising a time-based differential equation model for modelling a time dependence of a plasma concentration of the incretin pathway drug as a function of the patient data.

The dosage calculator may be derived from the PK model and an energy intake—total daily energy expenditure model.

The method may comprise:
  receiving updated patient data comprising updated patient weight data;
  updating the dosage calculator based on the updated patient data; and processing the updated patient data with the updated dosage calculator to determine an updated dosage; and indicating the updated dosage.

The updated patient data may comprise energy intake data and/or physical activity data. The method comprises updating an energy intake—total energy expenditure model using the updated patient weight data and the energy intake data and/or the physical activity data.

Processing the patient data with a dosage calculator to determine the dosage of the incretin pathway drug for administering to the patient may comprise:

setting an initial value of a dose estimate;

processing the dose estimate with the dosage calculator to determine a predicted drug concentration;

comparing the predicted drug concentration to a target drug concentration; and determining the dosage for administering to the patient by refining the dose estimate based on the comparison.

Refining the dose estimate may comprise:

iteratively adjusting the dose estimate and recalculating the predicted drug concentration until a difference between the predicted drug concentration and the target drug concentration is less than a difference threshold; or setting one or more further values of the dose estimate and processing the one or more further values with the dosage calculator to estimate one or more further predicted drug concentrations; and determining the dosage for administering to the patient by interpolating the dosage value corresponding to the target drug concentration based on the relationship between the initial value of the dose estimate, the one or more further values of the dose estimate, the predicted drug concentration and the one or more further predicted drug concentrations.

The target drug concentration may comprise a target plasma level. The target plasma level may comprise one or more of:

a target trough plasma level comprising an ideal therapeutic level;

a target maximum plasma level being less than a maximum level threshold;

a target average plasma level over a dosing interval at steady state comprising an ideal therapeutic level;

a target area under the curve of a plasma level time profile comprising an ideal therapeutic level;

a target ratio of a maximum plasma level to a trough plasma level comprising an ideal therapeutic ratio and level; or a target ratio of the maximum plasma level to the area under the curve of the plasma level time profile comprising an ideal therapeutic ratio and level.

The dosage calculator may comprise a machine learning algorithm trained using a PK model.

The machine learning algorithm may be trained using a PK model and an energy intake—total daily energy expenditure model.

The dosage calculator may comprise a machine learning algorithm trained using simulated population data obtained from the PK model.

The calculator may comprise a machine learning algorithm trained using:

simulated population data obtained from the PK model; and real population data.

The machine learning algorithm may be locked to prevent further adjustment to the machine learning algorithm.

The machine learning algorithm may comprises an adjustable machine learning algorithm. The method may comprise:

receiving updated patient data including a metabolism metric from a physiological test result; and adjusting the machine learning model based on the metabolism metric.

The dosage calculator may comprise a PK model.

The dosage calculator may comprise a PK model and an energy intake—total daily energy expenditure model.

The dosage calculator may comprise one or more look-up tables defined according to simulated population data obtained from a PK model.

Processing the patient data with the dosage calculator to determine the dosage of the incretin pathway drug for administering to the patient may comprise:

processing the patient data with the dosage calculator to determine an ideal dosage regime; and selecting the dosage for administering to the patient from a selection of available dosage regimes based on the ideal dosage regime.

The selection of available dosage regimes may comprise dosage amounts comprising: 0.25, 0.5, 1.0, 1.7 and 2.4 mg of subcutaneous semaglutide for administration once weekly.

The selection of available dosage regimes may comprise dosage amounts of subcutaneous semaglutide comprising any integer multiple of 0.05 mg from 0.05 mg up to 10.00 mg.

The selection of available dosage regimes may comprise dosage amounts of oral semaglutide comprising any integer multiple of 0.25 mg from 0.25 mg up to 30.00 mg.

The selection of available dosage regimes may comprise dosage amounts comprising: 2.5, 5, 7.5, 10, 12.5, and 15 mg of subcutaneous tirzepatide administered once weekly.

The selection of available dosage regimes may comprise dosage amounts of subcutaneous tirzepatide comprising any integer multiple of 0.5 mg from 0.5 mg up to 60 mg once weekly.

The selection of available dosage regimes may comprise dosage amounts comprising: 0.25, 0.5, 1.0, 1.7, 2.0, 2.4, 3.4 and 4.8 mg subcutaneous Cagrisema once weekly.

The selection of available dosage regimes may comprise dosage amounts comprising dosage amounts of subcutaneous Cagrisema comprising any integer multiple of 0.05 mg from 0.05 mg up to 10.00 mg.

Processing the patient data with the dosage calculator to determine the dosage of the incretin pathway drug for administering to the patient may comprise processing the patient data with the dosage calculator to determine one or more of: a dosage amount; a dosage time; a dosage frequency; and/or a dosage type.

Processing the patient data with the dosage calculator to determine the dosage of the incretin pathway drug for administering to the patient may comprise processing the patient data with the dosage calculator to determine:

a personalised dosage amount for a fixed dosage frequency;

a personalised dosage frequency for a fixed dosage amount; or a personalised dosage amount and a personalised dosage frequency.

Indicating the dosage may comprise indicating the dosage to a health care professional and/or to the patient.

The method may comprise:
  setting a calorie intake regimen based on the patient data; and
  indicating the calorie intake regimen.

The dosage may comprise an initial dosage and the method may comprise:
  determining an expected energy intake trajectory based on the initial dosage; and
  setting the calorie intake regimen based on the expected energy intake trajectory.

The method may comprise setting the calorie intake regimen based on an initial weight and a target weight of the patient weight data.

The method may comprise:
  receiving updated patient data;
  adjusting the calorie intake regimen based on the updated patient data;
  processing the updated patient data with the dosage calculator to determine an updated dosage for administering to the patient; and
  indicating the updated calorie intake regimen and the updated dosage.

According to a second aspect of the present disclosure there may be provided a computer readable medium comprising instructions which, when executed by one or more processors, cause the one or more processors to carry out the method of any method disclosed herein.

According to a third aspect of the present disclosure there is provided a system for determining a dosage of an incretin pathway drug for administering to a patient, the system comprising one or more processors configured to perform any method disclosed herein.

According to a fourth aspect of the present disclosure there is provided a dosage calculator for determining a dosage of an incretin pathway drug for administering to a patient for the treatment of obesity, the dosage calculator comprising one or more processors configured to:
  receive patient data relating to a patient, wherein the patient data includes patient weight data;
  process the patient data with a dosage calculator to determine the dosage of the incretin pathway drug for administering to the patient; and
  indicate the dosage.

According to a fifth aspect of the present disclosure there is provided semaglutide for use in the treatment of obesity, wherein the semaglutide dosage is determined by steps comprising:
  receiving patient data relating to a patient, wherein the patient data includes patient weight data;
  processing the patient data with a dosage calculator to determine the dosage of semaglutide for administering to the patient; and
  indicating the dosage.

According to a further aspect of the present disclosure there is provided tirzepatide for use in the treatment of obesity, wherein the tirzepatide dosage is determined by steps comprising:
  receiving patient data relating to a patient, wherein the patient data includes patient weight data;
  processing the patient data with a dosage calculator to determine the dosage of tirzepatide for administering to the patient; and
  indicating the dosage.

According to a further aspect of the present disclosure there is provided Cagrisema for use in the treatment of obesity, wherein the Cagrisema dosage is determined by steps comprising:
  receiving patient data relating to a patient, wherein the patient data includes patient weight data;
  processing the patient data with a dosage calculator to determine the dosage of Cagrisema for administering to the patient; and
  indicating the dosage.

According to a sixth aspect of the present disclosure there is provided a method of treating obesity comprising administering an incretin pathway drug to a patient in need thereof, wherein the incretin pathway drug dosage is determined by the steps comprising:
  receiving patient data relating to a patient, wherein the patient data includes patient weight data;
  processing the patient data with a dosage calculator to determine the dosage of the incretin pathway drug for administering to the patient; and
  indicating the dosage.

According to a seventh aspect of the present disclosure there is provided a computer implemented method for determining a dosage of an incretin pathway drug for administering to a patient for the treatment of type 2 diabetes, the method comprising:
  receiving patient data relating to a patient, wherein the patient data includes patient weight data;
  processing the patient data with a dosage calculator to determine the dosage of incretin pathway drug for administering to the patient; and
  indicating the dosage.

The incretin pathway drug may comprise semaglutide.

The incretin pathway drug may comprise a GIP agonist or a dual GLP1/GIP agonist.

The incretin pathway drug may comprise tirzepatide.

The incretin pathway drug may comprise Cagrisema (cagrilintide and semaglutide coformulation).

The incretin pathway drug may comprise a GLP-1 receptor agonist. The incretin pathway drug may comprise one of: albiglutide, dulaglutide, exenatide, liraglutide, efpeglenatide (also called langlenatide) or lixisenatide. The incretin pathway drug may comprise one of: beinaglutide or ecnoglutide. The incretin pathway drug may comprise an oxyntomodulin analogue such as DA-1726.

The incretin pathway drug may comprise a GLP-1 and glucagon receptor co-agonist. The incretin pathway drug may comprise one of: bamadutide, cotadutide, pegapamodutide, pemvidutide, or survodutide. The incretin pathway drug may comprise a GLP-1/GCCR/GIP triple agonist such as retatrutide.

The incretin pathway drug may include: maridebart cafraglutide (Maritide), cagrilintide/semaglutide (Cagrisema), pemvidutide, mazdutide or efinopegdutide. The incretin pathway drug may comprise a GLP-1, GCCR and/or GIP drug in development including: Orforglipron, CT-388, CT-868, GX-G6, GMA 105, HM11260C, Danuglipron, GSBR-1290, Pegapamodutide, VK-2735, Dapiglutide, AMG-786, ECC5004, YH 25724, CT-996, DD-01, UBT251, HM15136, HDM1002, NNC-9204-1706, PB-119, SAR425899 [68Ga] Ga-DO3A-VS-Cys40-Tuna-2, XW 014, XW-004, TAK-094, GMA-106, Utreglutide, TERN 601 or DR-10624.

The dosage calculator may be derived from a pharmacokinetic, PK, model.

The patient data may further comprise one or more of: a patient age; a patient ethnicity; a patient gender; a patient diabetes history; a kidney function metric; a pharmacogenomic profile; a dosage route and a patient medication list.

The dosage route may comprise an oral dosage. The patient data may further comprise fasting time data and water intake data.

The dosage route may comprise a subcutaneous dosage. The patient data may further comprise an injection site.

Processing the patient data with a dosage calculator to determine the dosage of the incretin pathway drug for administering to the patient may comprise:
receiving a target drug concentration; and
calculating the dosage for administering to the patient by processing the patient data and the target drug concentration with the dosage calculator.

The target drug concentration may comprise: a target drug plasma level, a target whole blood drug level or a target drug serum level.

The incretin pathway drug may comprise semaglutide and the target drug concentration may comprise a target plasma level from 10 nmol/L to 40 nmol/L.

The patient data may comprise diabetes metric data. The method may comprise determining the target drug concentration based on the diabetes metric data.

The diabetes metric data may comprise one or more of: Hba1c data, fasting blood glucose data and continuous glucose monitoring data.

The method may be for use in determining a dosage for administering to a patient for the treatment of diabetes and obesity.

The incretin pathway drug may comprise semaglutide and the target drug concentration may comprise a target plasma level from 50 nmol/L to 100 nmol/L.

The patient data comprises an initial weight and a target weight and the method comprises determining the target drug concentration based on the initial weight and the target weight.

The method may comprise processing the patient data with a dosage calculator to determine an initial dosage of the incretin pathway drug for administering to the patient.

The patient data may further comprise a patient side effect tolerance. The method may comprise processing the patient side effect tolerance with the dosage calculator to determine the initial dosage.

Processing the patient side effect tolerance with the dosage calculator may comprise:
setting a target drug concentration based on the side effect tolerance; and
determining the initial dosage based on the target drug concentration and the patient data.

The target drug concentration may comprise: a target drug plasma level, a target whole blood drug level, or a target drug serum level.

The method may comprise:
processing the patient side effect tolerance and the patient data with the dosage calculator to obtain a target drug concentration that satisfies the patient side effect tolerance; and
processing the target drug concentration with the dosage calculator to determine the initial dosage.

The dosage calculator may comprise a side-effect calculator derived from a side effect model. The side effect model may comprise a discrete-time Markov side effect model or an Emax exposure response side effect model.

Processing the patient side effect tolerance and the patient data with the dosage calculator may comprise processing the patient side effect tolerance and the patient data with the side effect calculator. The side effect calculator may comprise a machine learning model. The machine learning model may have been trained using simulated population data generated by the discrete-time Markov side effect model or the Emax exposure response side effect model. The simulated population data may be generated by processing simulated patient data with the discrete-time Markov model or the Emax exposure side effect model. The simulated population data may be generated by processing the simulated patient data with the discrete-time Markov model a plurality of times, and defining the simulated population data as summary metrics. The summary metrics may comprise one or more of: the mean number of adverse event occasions, the mean duration of each adverse event occasion, the mean time spent experiencing each adverse event, the mean time spent experiencing an adverse event of a given severity, the mean proportion of the entire treatment period spent experiencing each adverse event, and the mean proportion of the entire treatment period spent experiencing an adverse event of a given severity. The side effect tolerance may comprise one or more of: a gastro-intestinal side effect tolerance, a nausea side effect tolerance, a vomiting target; and a diarrhoea side effect tolerance.

Processing the patient side effect tolerance with the dosage calculator may comprise: determining a nominal initial dosage based on the patient data; and adjusting the nominal initial dosage based on the side effect tolerance.

The method may further comprise:
receiving updated patient data including updated patient weight data; and
processing the updated patient data with the dosage calculator to determine an updated dosage; and
indicating the updated dosage.

Indicating the updated dosage may comprise indicating the updated dosage if an elapsed time since a previous dose adjustment exceeds a drug effect time threshold.

Processing the updated patient data with the dosage calculator to determine an updated dosage may comprise:
comparing weight loss data from the patient weight data to a weight loss limit; and
reducing the dosage if the weight loss data indicates a weight loss greater than the weight loss limit.

The updated patient data may include reported side effect data. Processing the updated patient data with the dosage calculator to determine an updated dosage may comprise reducing the dosage if the reported side effect data satisfies one or more side effect severity thresholds.

The updated patient data may include reported side effect data and Processing the updated patient data with the dosage calculator to determine an updated dosage may comprise reducing the dosage if the reported side effect data satisfies one or more side effect severity thresholds unless the reported side effect data indicates a patient willingness to proceed.

The updated patient data may include updated diabetic metric data. The method may comprise processing the diabetic metric data with the dosage calculator to determine the updated dosage.

The method may comprise:
reducing the dosage if the diabetes metric data is representative of a risk of hypoglycaemia; and
indicating the reduced dosage.

The method may comprise:
reducing the dosage if the diabetes metric data indicates glycemic control within normal range; and
indicating the reduced dosage.

The method may comprise:
increasing the dosage if the diabetes metric data indicates an improvement in glycemic control that is less than a threshold improvement; and
indicating the increase dosage.

The diabetes metric data may comprise one or more of: Hba1c data, fasting blood glucose data and continuous glucose monitoring data.

The dosage calculator may be derived from a PK model comprising a time-based differential equation model for modelling a time dependence of a plasma concentration of the incretin pathway drug as a function of the patient data.

Processing the patient data with a dosage calculator to determine the dosage of the incretin pathway drug for administering to the patient may comprise:
setting an initial value of a dose estimate;
processing the dose estimate with the dosage calculator to determine a predicted drug concentration;
comparing the predicted drug concentration to a target drug concentration; and
determining the dosage for administering to the patient by refining the dose estimate based on the comparison.

Refining the dose estimate may comprise:
iteratively adjusting the dose estimate and recalculating the predicted drug concentration until a difference between the predicted drug concentration and the target drug concentration is less than a difference threshold; or
setting one or more further values of the dose estimate and processing the one or more further values with the dosage calculator to estimate one or more further predicted drug concentrations; and
determining the dosage for administering to the patient by interpolating the dosage value corresponding to the target drug concentration based on the relationship between the initial value of the dose estimate, the one or more further values of the dose estimate, the predicted drug concentration and the one or more further predicted drug concentrations.

The dosage calculator may comprise a machine learning algorithm trained using a PK model.

The dosage calculator may comprise a machine learning algorithm trained using simulated population data obtained from the PK model.

The dosage calculator may comprise a machine learning algorithm trained using:
simulated population data obtained from the PK model; and
real population data.

The machine learning algorithm may be locked to prevent further adjustment to the machine learning algorithm.

The machine learning algorithm may comprise an adjustable machine learning algorithm. The method may further comprise:
receiving updated patient data including diabetic metric data from a physiological test result; and
adjusting the machine learning model based on the diabetic metric data.

The diabetes metric data may comprise one or more of: Hba1c data, fasting blood glucose data and continuous glucose monitoring data.

The dosage calculator may comprise a PK model.

The dosage calculator may comprise one or more look-up tables defined according to simulated population data obtained from a PK model.

Processing the patient data with the dosage calculator to determine the dosage of the incretin pathway drug for administering to the patient may comprise:
processing the patient data with the dosage calculator to determine an ideal dosage regime; and
selecting the dosage for administering to the patient from a selection of available dosage regimes based on the ideal dosage regime.

The selection of available dosage regimes may comprise dosage amounts comprising: 0.5 and 1.0 mg of subcutaneous semaglutide for administration once weekly.

The selection of available dosage regimes may comprise dosage amounts of subcutaneous semaglutide comprising any integer multiple of 0.05 mg from 0.05 mg up to 10.00 mg.

The selection of available dosage regimes may comprise dosage amounts of oral semaglutide comprising any integer multiple of 0.25 mg from 0.25 mg up to 30.00 mg.

The selection of available dosage regimes may comprise dosage amounts comprising: 2.5, 5, 7.5, 10, 12.5, and 15 mg of subcutaneous tirzepatide administered once weekly.

The selection of available dosage regimes may comprise dosage amounts of subcutaneous tirzepatide comprising any integer multiple of 0.5 mg from 0.5 mg up to 60 mg once weekly.

The selection of available dosage regimes may comprise dosage amounts comprising: 0.25, 0.5, 1.0, 1.7, 2.0, 2.4, 3.4 and 4.8 mg subcutaneous Cagrisema once weekly.

The selection of available dosage regimes may comprise dosage amounts comprising dosage amounts of subcutaneous Cagrisema comprising any integer multiple of 0.05 mg from 0.05 mg up to 10.00 mg.

Processing the patient data with the dosage calculator to determine the dosage of the incretin pathway drug for administering to the patient may comprise processing the patient data with the dosage calculator to determine one or more of: a dosage amount; a dosage time; a dosage frequency; and/or a dosage type.

Processing the patient data with the dosage calculator to determine the dosage of the incretin pathway drug for administering to the patient may comprise processing the patient data with the dosage calculator to determine:
a personalised dosage amount for a fixed dosage frequency;
a personalised dosage frequency for a fixed dosage amount; or
a personalised dosage amount and a personalised dosage frequency.

Indicating the dosage may comprise indicating the dosage to a health care professional and/or to the patient.

The method may further comprise:
setting a behavioural regimen based on the patient data; and
indicating the behavioural regimen.

The behavioural regimen may comprise one or more of: a calorie intake regimen, a physical activity regimen and a sleep regimen.

According to an eighth aspect of the present disclosure there is provide a dosage calculator for determining a dosage of an incretin pathway drug for administering to a patient for the treatment of diabetes, the dosage calculator comprising one or more processors configured to:
receive patient data relating to a patient, wherein the patient data includes patient weight data;

process the patient data with a dosage calculator to determine the dosage of the incretin pathway drug for administering to the patient; and indicate the dosage.

According to a ninth aspect of the present disclosure there is provided semaglutide for use in the treatment of diabetes, wherein the semaglutide dosage is determined by steps comprising:

receiving patient data relating to a patient, wherein the patient data includes patient weight data;

processing the patient data with a dosage calculator to determine the dosage of semaglutide for administering to the patient; and indicating the dosage.

According to a yet further aspect of the present disclosure there is provided tirzepatide for use in the treatment of diabetes, wherein the tirzepatide dosage is determined by steps comprising:

receiving patient data relating to a patient, wherein the patient data includes patient weight data;

processing the patient data with a dosage calculator to determine the dosage of tirzepatide for administering to the patient; and indicating the dosage.

According to a yet further aspect of the present disclosure there is provided Cagrisema for use in the treatment of diabetes, wherein the Cagrisema dosage is determined by steps comprising:

receiving patient data relating to a patient, wherein the patient data includes patient weight data;

processing the patient data with a dosage calculator to determine the dosage of Cagrisema for administering to the patient; and indicating the dosage.

According to a tenth aspect of the present disclosure there is provided a method of treating diabetes comprising administering an incretin pathway drug to a patient in need thereof, wherein the incretin pathway drug dosage is determined by the steps comprising:

receiving patient data relating to a patient, wherein the patient data includes patient weight data;

processing the patient data with a dosage calculator to determine the dosage of the incretin pathway drug for administering to the patient; and indicating the dosage.

According to an eleventh aspect of the present disclosure there is provided a method for generating a co-therapy for a patient for the treatment of obesity, wherein the co-therapy comprises an incretin pathway drug for administering to the patient according to a dosage regimen and a digital therapeutic program comprising a behavioural regimen for administering using an electronic device, wherein the method comprises:

receiving personalised patient data;

setting an incretin drug dosage of the dosage regimen based on the personalised patient data;

setting a calorie intake regimen of the behavioural regimen based on the personalised patient data;

indicating the incretin drug dosage and the calorie intake regimen.

The method may comprise setting a timing of the behavioural regimen to synchronise with a timing of the administration of the dose of the incretin pathway drug.

The method may comprise setting a timing of the calorie intake regimen in accordance with a timing of a satiety effect of the incretin drug dosage.

The personalised patient data may comprise an initial weight and a target weight for the patient. The method may comprise setting the calorie intake regimen based on the initial weight and the target weight.

The personalised patient data may comprise an initial weight and a target weight for the patient and the method may comprise setting an initial incretin dosage regimen based on the initial weight and the target weight.

The incretin drug dosage may comprise an initial incretin drug dosage. The method may comprise:

determining an expected energy intake trajectory based on the initial incretin drug dosage; and setting the calorie intake regimen based on the expected energy intake trajectory.

The personalised patient data may comprise patient progress data comprising one or more of: patient weight loss data, patient calorie intake data, patient motivation score, patient satiety score; patient side effect data; and patient activity data.

The method may comprise:

adjusting the incretin drug dosage and/or the calorie intake regimen based on the patient progress data; and indicating the adjusted incretin drug dosage and/or the adjusted calorie intake regimen.

Setting or adjusting the incretin drug dosage may comprise setting one or more dosage amounts or one or more corresponding dosage timings of the dosage regimen of the incretin pathway drug.

Adjusting the calorie intake may comprise one or more of: increasing or decreasing a calorie intake allowance; increasing or decreasing a rate of change of the calorie intake allowance; and adjusting instructions relating to timing of calorie intake or types of food consumed.

The method may comprise:

adjusting the incretin drug dosage based on the patient progress data if an elapsed time exceeds a dosage effect time threshold; and indicating the adjusted incretin drug dosage.

The method may comprise:

increasing a calorie intake allowance of the calorie intake regimen if:

the patient calorie intake data represents a calorie intake greater than a first upper calorie intake threshold;

the patient motivation score is less than a motivation score threshold; or the patient satiety score is less than a first lower patient satiety threshold; and indicating the increased calorie intake allowance.

The method may comprise temporarily increasing the calorie intake allowance of the calorie intake regimen for a time period corresponding to a drug effect time following an increase in the incretin drug dosage.

The method may comprise:

increasing a calorie intake allowance of the calorie intake regimen and increasing the incretin drug dosage if:

the patient calorie intake data represents a calorie intake greater than a second upper calorie intake threshold;

the patient motivation score is less than a motivation score threshold; or the patient satiety score is less than a second lower patient satiety threshold; and indicating the increased incretin drug dosage and the increased calorie intake allowance.

The method may comprise:
increasing the incretin drug dosage if:
    the patient weight loss data represents a weight loss less that is less than an acceptable weight loss trajectory;
    the patient calorie intake data represents a calorie intake greater than a third upper calorie intake threshold; or
    the patient satiety score is less than a third lower patient satiety threshold; and
indicating the increased incretin drug dosage.

The method may comprise:
decreasing the incretin drug dosage if:
    the patient weight loss data represents a weight loss greater than an acceptable weight loss trajectory; or
    the patient side effect data is representative of a level of side effects greater than a side effect intolerance threshold; and
indicating the decreased incretin drug dosage.

The method may comprise:
decreasing a calorie intake allowance of the calorie intake regimen if:
    the patient calorie intake data represents a calorie intake less than a first lower calorie intake threshold;
    the patient motivation score is greater than a motivation score threshold; or
    the patient satiety score is greater than a first upper patient satiety threshold.

The method may comprise:
during a weight loss phase of the treatment, adjusting the incretin pathway dosage and/or the calorie intake regimen based on the patient progress data to promote a weight loss trajectory towards the target weight; and
indicating the adjusted incretin pathway dosage and/or the adjusted calorie intake regimen.

The method may comprise indicating a transition from a weight loss phase to a weight maintenance phase if the patient weight loss data indicates a rate of weight loss has been less than a threshold weight loss rate for a period of time exceeding a stability time threshold.

The method may comprise:
during a weight maintenance phase of the treatment, adjusting the incretin pathway dosage and/or the calorie intake regimen based on the patient progress data to promote maintenance of the patient weight within a threshold range of the target weight; and
indicating the adjusted incretin pathway dosage and/or the adjusted calorie intake regimen.

The method may comprise:
during a weight loss phase of the treatment or a weight maintenance phase of the treatment, adjusting the incretin pathway dosage to promote maintenance of the patient satiety within a threshold patient satiety range; and
indicating the adjusted incretin pathway dosage and/or the adjusted calorie intake regimen.

The method may comprise:
during a drug withdrawal phase of the treatment, reducing the incretin pathway dosage and adjusting the calorie intake regimen based on the patient progress data to promote maintenance of the patient weight within a threshold range of the target weight and stop administration of the incretin pathway drug.

The method may comprise:
receiving patient weight loss data;
setting a physical activity regimen based on the patient weight loss data; and
indicating the physical activity regimen.

The method may comprise setting the physical activity regimen if the weight loss data indicates a weight loss satisfying a weight loss milestone.

The method may comprise setting an intensity of the physical activity regimen setting intensity based on the patient weight loss data.

The incretin pathway drug may comprise an agonist, a partial agonists, a small molecule, an antagonists, an analogues and receptor or a pathway drug.

The incretin pathway drug may comprise a GLP1 agonist or a GIP agonist.

The incretin pathway drug may comprise semaglutide.

The incretin pathway drug may comprise a GIP agonist or a dual GLP1/GIP agonist.

The incretin pathway drug may comprise tirzepatide.

The incretin pathway drug may comprise Cagrisema (cagrilintide and semaglutide coformulation).

The incretin pathway drug may comprise a GLP-1 receptor agonist. The incretin pathway drug may comprise one of: albiglutide, dulaglutide, exenatide, liraglutide, efpeglenatide (also called langlenatide) or lixisenatide. The incretin pathway drug may comprise one of: beinaglutide or ecnoglutide. The incretin pathway drug may comprise an oxyntomodulin analogue such as DA-1726.

The incretin pathway drug may comprise a GLP-1 and glucagon receptor co-agonist. The incretin pathway drug may comprise one of: bamadutide, cotadutide, pegapamodutide, pemvidutide, or survodutide. The incretin pathway drug may comprise a GLP-1/GCCR/GIP triple agonist such as retatrutide.

The incretin pathway drug may include: maridebart cafraglutide (Maritide), cagrilintide/semaglutide (Cagrisema), pemvidutide, mazdutide or efinopegdutide. The incretin pathway drug may comprise a GLP-1, GCCR and/or GIP drug in development including: Orforglipron, CT-388, CT-868, GX-G6, GMA 105, HM11260C, Danuglipron, GSBR-1290, Pegapamodutide, VK-2735, Dapiglutide, AMG-786, ECC5004, YH 25724, CT-996, DD-01, UBT251, HM15136, HDM1002, NNC-9204-1706, PB-119, SAR425899 [68Ga] Ga-DO3A-VS-Cys40-Tuna-2, XW 014, XW-004, TAK-094, GMA-106, Utreglutide, TERN 601 or DR-10624.

According to a twelfth aspect of the present disclosure there is provided a method of treating obesity comprising administering an incretin pathway drug to a patient in need thereof and administering a behavioural regimen using an electronic device, wherein the incretin pathway drug dosage and the behavioural regimen are determined by the steps comprising:
    receiving personalised patient data;
    setting an incretin drug dosage of the dosage regimen based on the personalised patient data;
    setting a calorie intake regimen of the behavioural regimen based on the personalised patient data;
    indicating the incretin drug dosage and the calorie intake regimen.

According to a thirteenth aspect of the present disclosure there is provided a method for treating obesity in a patient, the method comprising:
    administering a dose of an incretin pathway drug to the patient in a treatment regimen effective to manage the patient's satiety and thereby effect a reduction in the patient's weight; and,
    in conjunction with the administration of the dose of the incretin pathway drug, engaging in a directed digital therapeutic program that manages patient weight loss and the treatment regimen for the incretin pathway drug with the objective of achieving a predetermined target weight for the patient, wherein the patient achieves the target weight.

The incretin pathway drug may comprise an agonist, a partial agonist, a small molecule, an antagonist, an analogue and receptor or a pathway drug.

The incretin pathway drug may comprise a GLP1 agonist or a GIP agonist.

The incretin pathway drug may comprise semaglutide.

The incretin pathway drug may comprise a GIP agonist or a dual GLP1/GIP agonist.

The incretin pathway drug may comprise tirzepatide.

The incretin pathway drug may comprise Cagrisema (cagrilintide and semaglutide coformulation).

The incretin pathway drug may comprise a GLP-1 receptor agonist. The incretin pathway drug may comprise one of: albiglutide, dulaglutide, exenatide, liraglutide, efpeglenatide (also called langlenatide) or lixisenatide. The incretin pathway drug may comprise one of: beinaglutide or ecnoglutide. The incretin pathway drug may comprise an oxyntomodulin analogue such as DA-1726.

The incretin pathway drug may comprise a GLP-1 and glucagon receptor co-agonist. The incretin pathway drug may comprise one of: bamadutide, cotadutide, pegapamodutide, pemvidutide, or survodutide. The incretin pathway drug may comprise a GLP-1/GCCR/GIP triple agonist such as retatrutide.

The incretin pathway drug may include: maridebart cafraglutide (Maritide), cagrilintide/semaglutide (Cagrisema), pemvidutide, mazdutide or efinopegdutide. The incretin pathway drug may comprise a GLP-1, GCCR and/or GIP drug in development including: Orforglipron, CT-388, CT-868, GX-G6, GMA 105, HM11260C, Danuglipron, GSBR-1290, Pegapamodutide, VK-2735, Dapiglutide, AMG-786, ECC5004, YH 25724, CT-996, DD-01, UBT251, HM15136, HDM1002, NNC-9204-1706, PB-119, SAR425899 [68Ga] Ga-DO3A-VS-Cys40-Tuna-2, XW 014, XW-004, TAK-094, GMA-106, Utreglutide, TERN 601 or DR-10624.

There may be provided a computer program, which when run on a computer, causes the computer to configure any apparatus, including a circuit, controller, converter, or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

The computer program may be provided on a computer readable medium, which may be a physical computer readable medium such as a disc or a memory device, or may be embodied as a transient signal. Such a transient signal may be a network download, including an internet download. There may be provided one or more non-transitory computer-readable storage media storing computer-executable instructions that, when executed by a computing system, causes the computing system to perform any method disclosed herein.

BRIEF DESCRIPTION OF THE DRAWINGS

One or more embodiments will now be described by way of example only with reference to the accompanying drawings in which.

DETAILED DESCRIPTION

Figure 1:
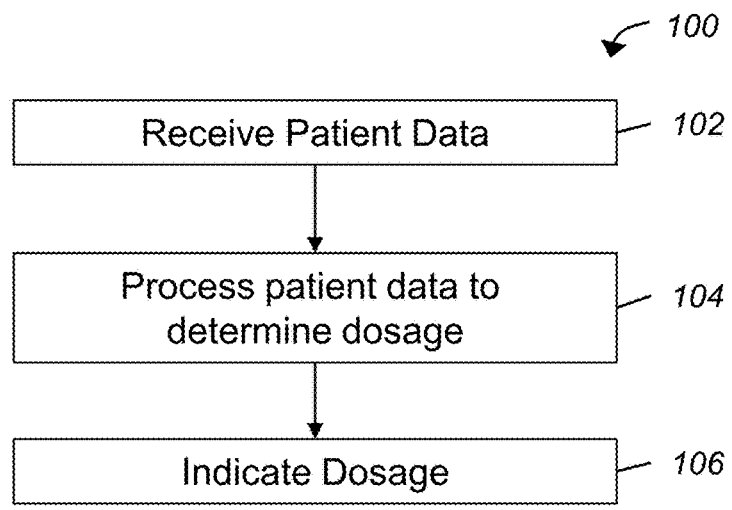
FIG. 1 illustrates a method for determining a dosage of an incretin pathway drug such as semaglutide for administering to the patient according to an embodiment of the present disclosure.

Type 2 diabetes (T2D) is a condition when blood glucose levels are no longer constrained within clinically defined limits. In healthy individuals, fasting glucose is regulated within very narrow limits ('normal' defined as between 60 mg/mL (3.3. mmol/L) and 100 mg/mL (5.5 mmol/L). Levels below this are classed as hypoglycaemia. Levels between 100 mg/ml (5.5 mmol/L) and 126 mg/mL (7.8 mmol/L) is classified as impaired fasting glucose (IFG) and above this as indicative of T2D. Type 2 diabetes mellitus (T2D) is the most common type of diabetes, making up approximately 90% of the total number of patients with diabetes in high-in-come countries.

The main risk factor for developing T2D is obesity which occurs in >60% of diabetic patients and it has been shown that even a moderate reduction in weight of 5% can lead to improvements in glycemic control and CV risk factors.

As well as being a major contributor to T2D, obesity is an independent growing health problem and a risk factor for cardiovascular disease, musculoskeletal disorders and some cancers. Thermodynamics dictates that energy is conserved. In terms of maintaining a stable body weight, this means that total daily energy intake ('EI') equals total daily energy expenditure ('TDEE'). Energy intake can be from new calories from food intake or from burning existing calories. Energy expenditure is a combination of calories burned from basal metabolic rate together with calories burned through activity. If new calories from food intake are less than the calories burned, then the deficit is made up from burning up calories stored in the body, particularly from glycogen and fat stores.

The majority of energy is stored in fat, particularly in obese individuals. Therefore, to lose weight, fundamentally one needs to enter into a calorie deficit from the perspective of eating. i.e., one needs to be on a diet.

There are a profusion of weight-loss diets with different food compositions and food timings including many forms of commercial meal replacement diets, Atkins, 5:2 diet, Weight Watchers and the ketogenic diet. A problem with all diets is sustainability. Typically, an individual may manage to embark on a diet and see some early weight loss, but then the intrinsic drive from the parts of our brain controlling appetite, in particular the hypothalamus, drive behaviour to return to the previous weight set point through increased consumption of food. Indeed, the body will also try to maintain weight whilst in calorie restriction through a decrease in the basal metabolic rate. One long term consequence of the temporary shift in weight and then homeostatic drive to return to baseline can be an overshoot from prior baseline such that the individual eventually ends up at a higher weight.

Successful weight loss requires dietary restriction that can be sustained long term with an ultimate permanent lower calorie intake, ideally accompanied by increased physical activity/exercise levels. Increasing the basal metabolic rate and maintaining the new lower weight set point can be facilitated by exercise.

The drive to eat can be considered as reflecting two states—hunger and satiety. There is also a sense of fullness, but this can be dissociated from satiety. For example, a patient may feel bloated or have delayed emptying of food from their stomach yet still feel calorie depleted and hungry. The term satiety is used herein to define a patient's desire to eat and the term is intended to encompass a level of: hunger, fullness, satiety or any other similar measure of a patient's desire to eat.

With healthy energy metabolism, post-prandial levels are well controlled with pancreatic B-cells increasing insulin to promote glucose uptake and alpha-cells signalling via lowered glucagon levels to reduce hepatic glucose output. The gut responds to nutrient intake by producing incretin hormones. Incretin hormones are gut hormones that work both in the GI tract and in the brain to control food intake and insulin release and thus glucose and fatty acid transport and metabolism, inter alia, with effects on multiple organs, pancreas, muscle, fat, bone, cardiovascular system. These hormones tend to be lower in diabetes and obese subjects. The incretin hormone GLP-1 (glucagon like peptide) inhibits glucagon secretion and hepatic glucose production. GIP acts on pancreatic B-cells to increase insulin production. During a meal, plasma-levels of GLP-1 rise within minutes and return to very low levels in the fasting state.

An incretin pathway drug refers to any drug that acts through or influences an incretin hormone effect. Incretin pathway drugs may include agonists, partial agonists, small molecules, large molecules, antagonists, analogues and receptor or pathway drugs. For example, incretin hormone agonists are synthetic analogue derivatives of the respective naturally occurring gut hormone which may be modified to increase stability in the human body.

Incretin pathway drugs have utility in diabetes management. GLP-1 asserts its effects through binding to the GLP-1Rs expressed in the pancreas and a variety of other tissues including: lung, heart, blood vessels, gastrointestinal tract, kidney, breast and central nervous system (CNS). In the pancreatic beta cell, receptor-binding of GLP-1 in the presence of elevated glucose concentrations leads to stimulation of insulin and inhibition of glucagon secretion when administrated large doses producing drug levels in excess of those seen physiologically.

A variety of incretin pathway drugs can also facilitate weight loss. One example class of incretin hormone agonists are GLP1 (glucagon like protein) agonists (which may simply be referred to herein as GLP1s) which can facilitate weight loss by: promoting a feeling of satiety (and fullness); slowing gastric emptying (feel fuller for longer); increased insulin secretion (which regulates glucose metabolism preventing excess glucose from being stored as fat) and decreasing glucagon secretion. It therefore makes it easier for the patient to calorie restrict. However, the GLP1 will not achieve weight loss in the absence of calorie restriction. A further class of incretin hormone agonists are GIP (gastric inhibitory protein) agonists which can facilitate patient weight loss by stimulating insulin in the pancreas thereby increasing glucose transport and metabolism.

Patients can be administered incretin pathway drugs, such as GLP1 agonists, for the treatment of: (i) obesity/weight loss independent of diabetes; (ii) weight loss/obesity and diabetes; and (iii) diabetes independently. In relation to (ii), in cases where obesity is the driver of type 2 diabetes, GLP1s can be administered for improved glycemic control and weight loss. The weight loss effects can beneficially result in remission of the type 2 diabetes. In particular, the removal of excess fat accumulation in the liver and pancreas (which causes diabetes) can normalise hepatic insulin responsiveness. In relation to (iii), type 2 diabetes can be brought on by factors other than obesity including age, genetic linkage (ethnicity and family), glycogen storage disease, mitochondrial disease and childhood cancer. For some of these patients the weight loss effect of GLP1s may be undesirable.

The methods and systems of the present disclosure can determine a dosage of an incretin pathway drug for administering to a patient. The dosage of the incretin pathway drug may be for the treatment of diabetes and/or obesity. The methods and systems can receive patient data, including patient weight data, and process the patient weight data with a dosage calculator to determine the dosage of the incretin pathway drug for administering to the patient, before indicating the dosage, for example to a clinician or patient. The dosage may be indicated using a digital app on a mobile device. In some examples, the dosage calculator is derived from a pharmacokinetic (PK) model (which may be a plasma level prediction model), or a pharmacokinetic pharmacodynamic (PKPD) model, for the incretin pathway drug. As referred to herein, a PK model may refer to a PK model or a PKPD model. In some examples, the incretin pathway drug is the GLP1 agonist semaglutide. In some examples, the incretin pathway drug is the GLP-1/GIP receptor co-agonist Tirzepatide. Tirzepatide is a glucose-dependent insulinotropic polypeptide (GIP) and glucagon-like peptide-1 (GLP-1) receptor co-agonist which suppresses glucagon secretion, slows gastric emptying, increases insulin sensitivity and secretion, and reduces appetite. In some examples, the incretin pathway drug comprises Cagrisema. Cagrisema comprises a coformulation of semaglutide (a GLP-1 receptor agonist) and cagrilintide (an amylin analogue) and targets multiple pathways to regulate appetite, weight, and glucose levels.

The methods and systems of the present disclosure can also provide or generate a co-therapy for a patient living with obesity. The co-therapy can comprise an incretin pathway drug and a behavioural regimen for administering using an electronic device (for example using the same digital app that indicates the dosage of the incretin pathway drug). The incretin pathway drug may comprise a GLP1 agonist, in particular semaglutide, a GIP agonist or a dual GLP1/GIP agonist. The methods and systems can receive personalised patient data and set a personalised dosage of the incretin pathway drug and/or a personalised calorie intake regimen of the behavioural regimen, based on the personalised patient data. The disclosed methods and systems can advantageously enable coordination of the drug therapy and the behavioural therapy to achieve a target weight loss. The disclosed methods and systems can advantageously enable synchronisation of the timing of a behavioural regimen provided by an electronic device with the drug treatment regimen, resulting in strong patient compliance with the treatment program and effective weight loss. As described below, the disclosed systems and methods can recommend provision of the treatment in a phased manner comprising a weight loss phase, a weight maintenance phase and a drug withdrawal phase. The systems and methods may incorporate a feedback loop which monitors patient progress data and recommends adjustments of the drug dosage and/or the behavioural regimen to maintain patient compliance and stay on a patient weight loss trajectory towards a target weight with a minimum of side effects.

Personalised Incretin Pathway Drug Dosage

As noted above, incretin pathway drugs, such as the GLP1 agonist semaglutide or the GIP and GLP-1 co-agonist tirzepatide, are provided with substantially fixed dosage regimens for adults, with limited flexibility (The term dosage regimen may also be referred to herein as dosage regime).

For example, in the UK, the administration of semaglutide is prescribed for an adult as:

Subcutaneous Injection for Obesity—

A maintenance dose of semaglutide 2.4 mg once-weekly is reached by starting with a dose of 0.25 mg. To reduce the likelihood of gastrointestinal symptoms, the dose should be escalated over a 16-week period to a maintenance dose of 2.4 mg once weekly (see Table 1). In case of significant gastrointestinal symptoms, consider delaying dose escalation or lowering to the previous dose until symptoms have improved.

TABLE 1

Dose escalation schedule

| Dose escalation | Weekly dose |
|---|---|
| Week 1-4 | 0.25 mg |
| Week 5-8 | 0.5 mg |
| Week 9-12 | 1 mg |
| Week 13-16 | 1.7 mg |
| Maintenance dose | 2.4 mg |

Weekly doses higher than 2.4 mg are not recommended.

Oral—the oral form of semaglutide is currently only licensed for diabetes with the current dosage regimen:
  Initial: 3 mg PO once daily×30 days; the 3-mg dose is intended for treatment initiation and is not effective for glycemic control
  After 30 days on 3 mg/day: Increase to 7 mg PO once daily After 30 days on 7 mg/day: May increase dose to 14 mg PO once daily if additional glycemic control needed
Subcutaneous injection for use in diabetes is:
  0.25 mg SC once weekly for 4 weeks initially; THEN increase to 0.5 mg once weekly
  If glycemic control not achieved after at least 4 weeks on 0.5-mg dose, can increase to 1 mg once weekly
  If glycemic control not achieved after at least 4 weeks on 1-mg dose, may increase to 2 mg once weekly; not to exceed 2 mg/week In the USA, the administration of Mounjaro (a brand of tirzepatide) is prescribed as an adjunct to diet and exercise to improve glycemic control in adults with type 2 diabetes mellitus (T2DM). The recommended starting dose of Mounjaro is 2.5 mg, which is injected subcutaneously once weekly. The 2.5 mg dosage is for treatment initiation and is not intended for glycemic control. After 4 weeks, the dosage is increased to 5 mg once weekly. If additional glycemic control is needed, the dosage is increased in 2.5 mg increments after at least 4 weeks on the current dose. The maximum dosage is 15 mg once weekly.

Similarly, in the USA, the administration of Zepbound (another brand of tirzepatide) is prescribed as an adjunct to a reduced-calorie diet and increased physical activity for chronic weight management in adults with an initial body mass index (BMI) of 30 kg/m$^2$ or greater (obesity) or 27 kg/m$^2$ or greater (overweight) in the presence of at least one weight-related comorbid condition (e.g. hypertension, dyslipidaemia, T2DM, obstructive sleep apnoea, or cardiovascular disease). The recommended starting dosage is 2.5 mg injected subcutaneously once weekly. The 2.5 mg dosage is for treatment initiation and is not intended to be a maintenance dose for chronic weight management. After 4 weeks, the dosage is increased to 5 mg once weekly. The dosage may then be increased by 2.5 mg after at least 4 weeks on the current dose. The recommended maintenance dosages in adults are 5 mg, 10 mg, and 15 mg once weekly. The transitional dosages of 2.5 mg, 7.5 mg and 12.5 mg are not recommended maintenance dosages. The treatment response and tolerability is considered when selecting the maintenance dosage. If patients do not tolerate a maintenance dosage, a lower maintenance dosage may be considered. The maximum dosage is 15 mg once weekly.

These stipulated, minimal flexibility dosing regimens do not allow for inter-patient drug effect variability. No dose adjustment is recommended to account for age, type 2 diabetes, renal impairment, or hepatic impairment, only to advise caution or against use for severe renal or hepatic impairment or avoid combination with other GLP1 agonists for type 2 diabetes. There is also no recommendations to account for inter-subject variability in response to the drug effect on weight reduction or side effects. The present disclosure allows for personalised and optimised dosing of incretin pathway drugs for providing effective glycemic control and managing side effects. The present disclosure allows for personalised and optimised dosing of incretin pathway drugs to improve weight loss therapy, improve patient adherence/concordance to the therapy and minimise side effects, among other advantages. The following description uses the examples of semaglutide, tirzepatide and Cagrisema, however the teachings are equally applicable to other GLP1 and/or GIP agonists and other incretin pathway drugs more generally.

FIG. 1 illustrates a method 100 for determining a dosage of semaglutide for administering to the patient according to an embodiment of the present disclosure.

A first step 102 comprises receiving patient data relating to a patient. The patient data includes a patient weight data. Patient weight can be the most significant driver of semaglutide drug plasma level variability between patients and will likely change over the course of therapy due to the effect of semaglutide on weight loss.

A second step 104 comprises processing the patient data with a dosage calculator to determine the dosage of semaglutide for administering to the patient. The dosage calculator may be derived from a PK model for semaglutide such as a plasma level prediction model. Example dosage calculators and plasma level prediction models are discussed in detail below.

A third step 106 comprises indicating the dosage. Indicating the dosage may comprise indicating the dosage to a patient and/or a healthcare provider (HCP) (which refers to practitioners generally (carers, nurses, pharmacists, doctors) but may also be referred to herein as a clinician). As described herein "indicating the dosage" refers to indicating a recommended dosage to a patient or clinician. It does not encompass an instruction to administer a dosage.

The method advantageously accounts for the biggest driver of variability in semaglutide drug plasma levels—patient weight. The term semaglutide drug plasma level may also be referred to herein as semaglutide plasma level, drug plasma level or simply plasma level. The term level may be referred to as a concentration. As described below, embodiments of the method can process patient data comprising a plurality of parameters that contribute to plasma level variability, such as demographic data, physiological data and patient behavioural data, to advantageously provide personalised dosages for patients. The method can calculate a starting dose for a patient. The method can also continue to monitor patient data and provide a revised dose for a patient as their patient data changes. In this way, the method can provide personalised starting doses and an ongoing personalised semaglutide dosage regimen.

The method of FIG. 1 may be applied to tirzepatide, Cagrisema or any other incretin pathway drug and the term drug plasma level may be construed accordingly.

The disclosed systems and methods may be particularly advantageous for the paediatric population, where dosing requirements will differ from adults on account of their lower overall weight and height.

The US CDC reports that for children and adolescents aged 2-19 years in 2017-2020:
- The prevalence of obesity was 19.7% and affected about 14.7 million children and adolescents.
- Obesity prevalence was 12.7% among 2- to 5-year-olds, 20.7% among 6- to 11-year-olds, and 22.2% among 12- to 19-year-olds. Childhood obesity is also more common among certain populations.
- Obesity prevalence was 26.2% among Hispanic children, 24.8% among non-Hispanic Black children, 16.6% among non-Hispanic White children, and 9.0% among non-Hispanic Asian children.

Dosage Calculator

Determining an Initial Dosage

In its simplest form, the dosage calculator can process the patient weight data and determine an initial incretin pathway drug dosage, such as a semaglutide dosage, for administration (which may be different from that prescribed in the patient information leaflet). The initial incretin pathway drug dosage/semaglutide dosage may comprise an initial dosage regimen comprising one or more dosage amounts and one or more corresponding dosage timings. The initial dosage may comprise a step-wise increase in dosage amount over time to a steady-state maximum dose. As referred to herein, the initial dosage may correspond to this steady-state maximum dosage (or maintenance dosage) at the end of the stepwise increase. As referred to herein, determining, setting or adjusting the incretin pathway drug/semaglutide dosage may refer to determining, setting or adjusting a dosage titration trajectory or ramp profile in which a dosage amount is gradually increased and/or decreased in discrete steps over a period of time (e.g. as the incretin pathway drug/semaglutide is first introduced at the start of treatment, adjusted in response to patient data or withdrawn at the end of treatment).

Target Plasma Level

In some examples, the second step 104 may comprise setting or receiving a target plasma level and determining the initial dosage based on the target plasma level. The target plasma level will differ depending on whether the incretin pathway drug/semaglutide is to be administered for diabetes or obesity (or both).

Obesity

For the treatment of obesity, the target plasma level may be determined based on a target weight loss. The patient weight data may include an initial weight (e.g. an initial weight measurement) and a target weight. The target weight may be agreed between the patient and a clinician when the treatment is prescribed. In some examples, the target weight loss may be determined based on clinical guidelines, patient comorbidities, patient motivation level, patient's risk of adverse cardiovascular health outcomes. The target weight loss may be determined by any of the systems or methods disclosed herein. The target weight may be determined by a third party such as a payor or payor intermediary. The target weight may be determined based on a particular totality of administered drug and/or associated cost. The difference between the initial weight and a target weight may define the target weight loss.

In some examples, the second step 104 may comprise: setting a target plasma level based on the initial weight and the target weight; and determining an initial dosage based on the target plasma level and the initial weight.

Figure 2A:
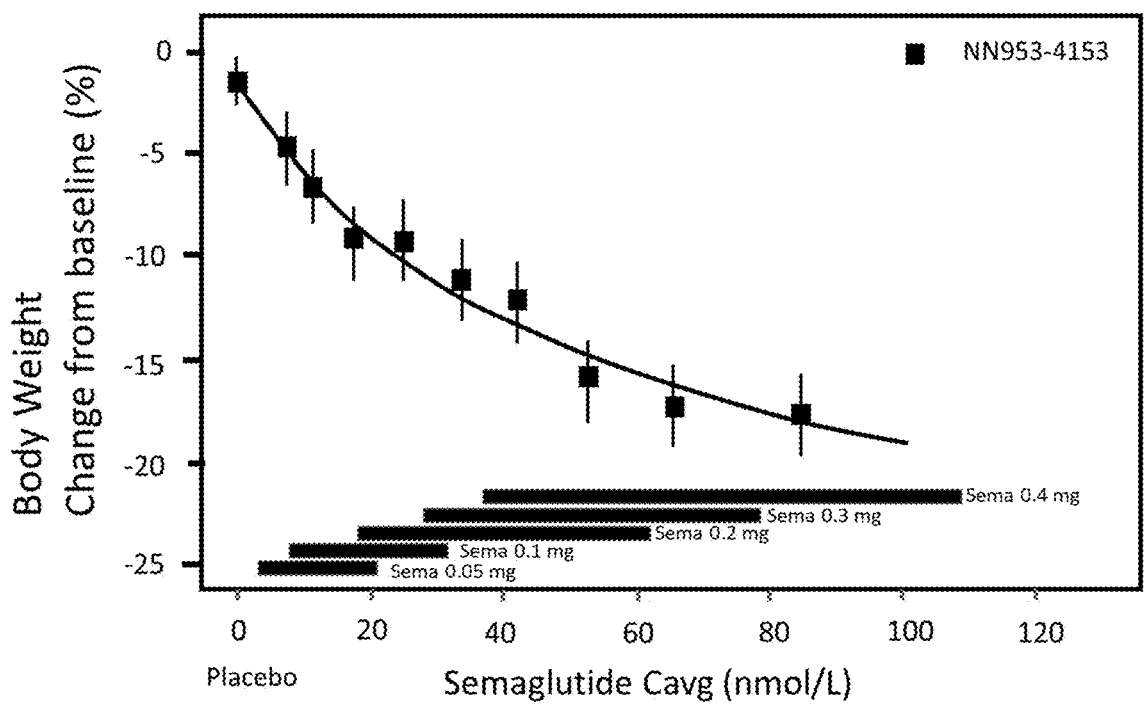
FIG. 2A shows patient study data illustrating a logarithmic relationship between achieved weight loss and a steady state GLP1 plasma level concentration.

FIG. 2A shows patient study data [1] illustrating a logarithmic relationship between achieved weight loss and a steady state GLP1 plasma level concentration, in this example semaglutide. The method may comprise converting the target weight loss to a target blood concentration using such a predetermined weight loss to plasma concentration relationship. The predetermined weight loss to plasma concentration relationship may comprise a sigmoidal Emax model that models drug effect (weight loss) as a function of plasma level, an example of which is described below. The sigmoidal Emax model may be derived from patient study data. The sigmoidal Emax model may comprise a personalised sigmoidal Emax model that defines a personalised relationship based on the patient data parameters (e.g. age, ethnicity, diabetes history, sex etc.). Such sigmoidal Emax models are known and not described in further detail here. The predetermined weight loss to plasma concentration relationship may form part of the dosage calculator.

In some examples, the method may set the target plasma level as an ideal therapeutic level (ITL) that is independent of the patient weight data. For example, the data of FIG. 2A illustrates maximum drug effect at plasma levels between 50 and 100 nmol/L. The ideal therapeutic level for semaglutide may therefore be from 50 to 100 nmol/L, for example 75 nmol/L. ITL values for tirzepatide, Cagrisema or other incretin pathway drugs may be defined by guidelines or determined from appropriate patient study data and exposure-response relationships.

Diabetes

Figure 2B:
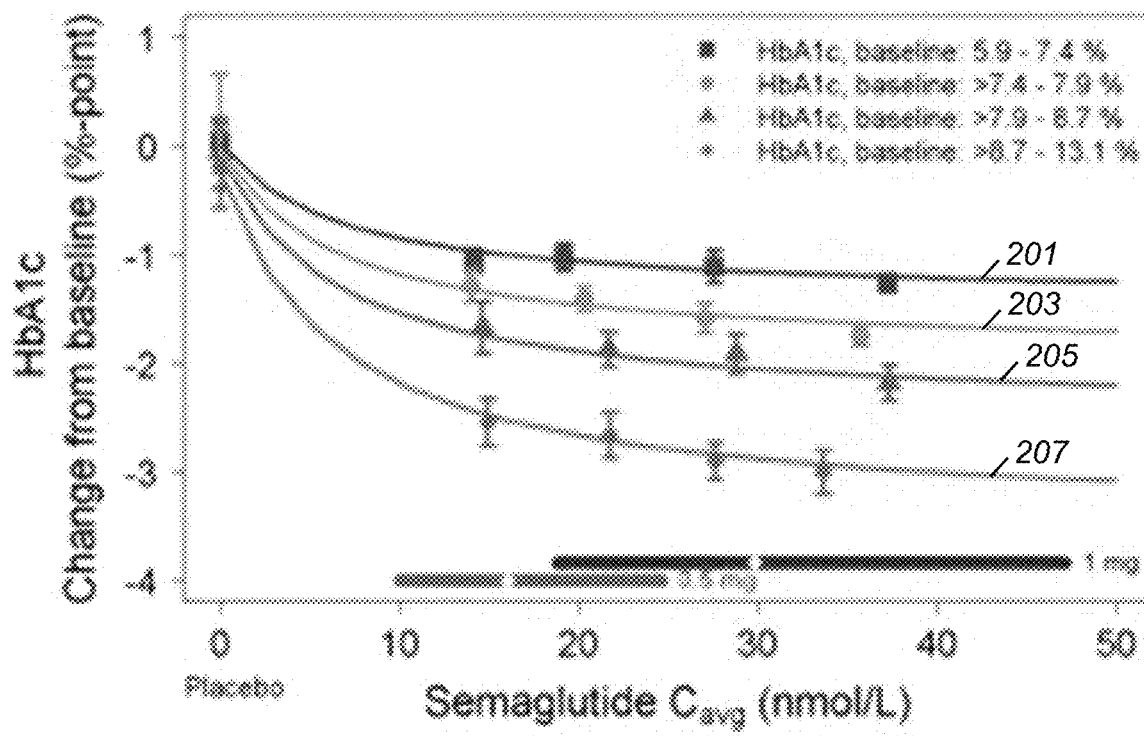
FIG. 2B shows study data illustrating the relationship between glycemic control and plasma level for patients administered subcutaneous semaglutide.

FIG. 2B shows study data illustrating the relationship between glycemic control (HbA1c reduction after 30 weeks) and plasma level for patients administered either 0.5 mg or 1.0 mg weekly subcutaneous semaglutide [2].

Various protein glycation products have been proposed in relation to T2D monitoring but glycated haemoglobin (HbA1c) has been adopted internationally both for diagnosis and disease progression monitoring. Haemoglobin is present in high concentrations in circulating red blood cells and so are exposed to plasma glucose. Red blood cells typically remain in circulation for some 2-3 months and glycation of Haemoglobin has been found to reliably reflect integrated exposure to glucose over the past 90-day period.

The adoption of HbA1c as a marker for T2D was made in the context:

HbA1c is a measure of average blood glucose over the past 3 months. This makes it a more accurate reflection of a person's overall glucose control than a single fasting blood glucose test.

HbA1c is less affected by transient glucose changes arising from exercise and diet than fasting blood glucose. This makes it a more reliable test for people with fluctuating blood glucose levels.

HbA1c is a simpler and more convenient test than the oral glucose tolerance test (OGTT), which was previously the gold standard for diagnosing diabetes.

HbA1c is regarded as normal below 42 mmol of glycated Haemoglobin/per mol of Haemoglobin present (6%). In individuals diagnosed with T2D DiabetesUK recommend that the HbA1c level is ideally managed to below 48 mmol/mol (6.5%).

The data of FIG. 2B includes four plots illustrating the trend for different groups of starting HbA1c level. A first plot 201 illustrates the trend of patients with a baseline HbA1c from 5.9-7.4%; a second plot 203 illustrates the trend of patients with a baseline HbA1c from 7.4-7.9%; a third plot 205 illustrates the trend of patients with a baseline HbA1c from 7.9-8.7%; and a fourth plot 207 illustrates the trend of patients with a baseline from 8.7-13.1%.

The data suggests that for all four groups, only a limited increase in effectiveness can be obtained by increasing the dose/plasma level. Therefore, in some examples, the method may comprise setting or receiving the target plasma level as an ideal therapeutic level. For example, the data of FIG. 2B illustrates a relatively constant drug effect at plasma levels from 15 to 40 nmol/L. The ideal therapeutic level for semaglutide may therefore be from 15 to 40 nmol/L, for example 20 nmol/L. In some examples, the ideal therapeutic level may be set to the lowest end of the range, i.e. nmol/L, to minimise the probability of side effects. ITL values for tirzepatide, Cagrisema or other incretin pathway drugs may be defined by guidelines or determined from appropriate patient study data and exposure-response relationships.

The data also illustrates that the slope and effectiveness of the drug for a given plasma level is dependent on starting HbA1c level and at high levels (>8.7%) the reduction was 3-fold higher than those with lower starting levels (<7.4%). Furthermore, the data illustrates that a plasma level greater than 15 nmol/L for patients with a lower starting point (first plot 201) are unnecessary (and not worth the increased side effect risk) because the slope is substantially fat. In contrast, higher plasma levels up to 35 nmol/L may benefit patients with a higher starting point HbA1c (fourth plot 207). Therefore, in some examples, the patient data may comprise diabetes metric data and the method may comprise setting a target plasma level based on the diabetes metric data. The diabetes metric data may comprise a starting HbA1c level or another diabetes metric (e.g. continuous glucose measurements (CGM) integrated over a number of days or weeks).

In some examples, the patient data may comprise a target end point of the incretin pathway drug/semaglutide treatment comprising a target glycemic control (e.g. a target HbA1c reduction). The method may set the target plasma level based on the target glycemic control and a predetermined relationship between plasma level and glycemic control, such as the relationship of FIG. 2B. As described above for obesity, the predetermined relationship may comprise a sigmoidal Emax model that models drug effect (glycemic control) as a function of plasma level. The sigmoidal Emax model may comprise a personalised sigmoidal Emax model (e.g. based on the patient data parameters (e.g. age, ethnicity, diabetes history, sex etc.)). In some examples, if the target glycemic control is too ambitious and not achievable (e.g. a patient with 12% starting HbA1c has a target HbA1c reduction of 4%) the method may revise the target glycemic control to the maximum achievable e.g. 3%.

For patients administered incretin pathway drugs/semaglutide for the treatment of both obesity and type 2 diabetes, the method may use the target plasma level approach described above in relation to obesity because the required plasma levels are higher for effective weight loss. Patients administered incretin pathway drugs/semaglutide solely for diabetes may also experience weight loss because the circulating plasma levels (e.g. 15 nmol/L) will still affect hunger and satiety and may lead to weight loss (FIG. 2A).

As discussed further below, for both obesity and diabetes, the target plasma level may be further refined based on a side effect tolerance of the patient. The term side effect tolerance may also be referred to herein as a side effect target or side effect threshold (i.e. a maximum level of tolerance for a particular side effect).

For both obesity and diabetes, the dosage calculator may determine an initial dosage based on the target plasma level and the initial weight using relationships derived from a PK model or a PKPD model. Although the terms plasma level and target plasma level are referred to throughout the detailed description, the terms are examples of (body) drug concentrations and target drug concentrations (i.e. in a (central) compartment). The methods and systems herein may use other drug concentrations and corresponding targets including: a plasma level, a whole blood level, and a serum level.

PK Model

The dosage calculator may be derived from a PK model (or PKPD model) for the incretin pathway drug, such as semaglutide, tirzepatide or Cagrisema. As outlined below, this may mean that the dosage calculator comprises the PK model itself, look-up tables derived from the PK model, or a machine learning calculator trained on simulated data from the PK model. PK models may comprise compartment models such as a single compartment model, a two-compartment model or a higher number of compartments. The PK model can enable the calculation of an incretin pathway drug/semaglutide plasma concentration as a function of time for a particular incretin pathway drug/semaglutide dosage for a specific patient having personalised patient data, including patient weight in particular.

Figure 3:
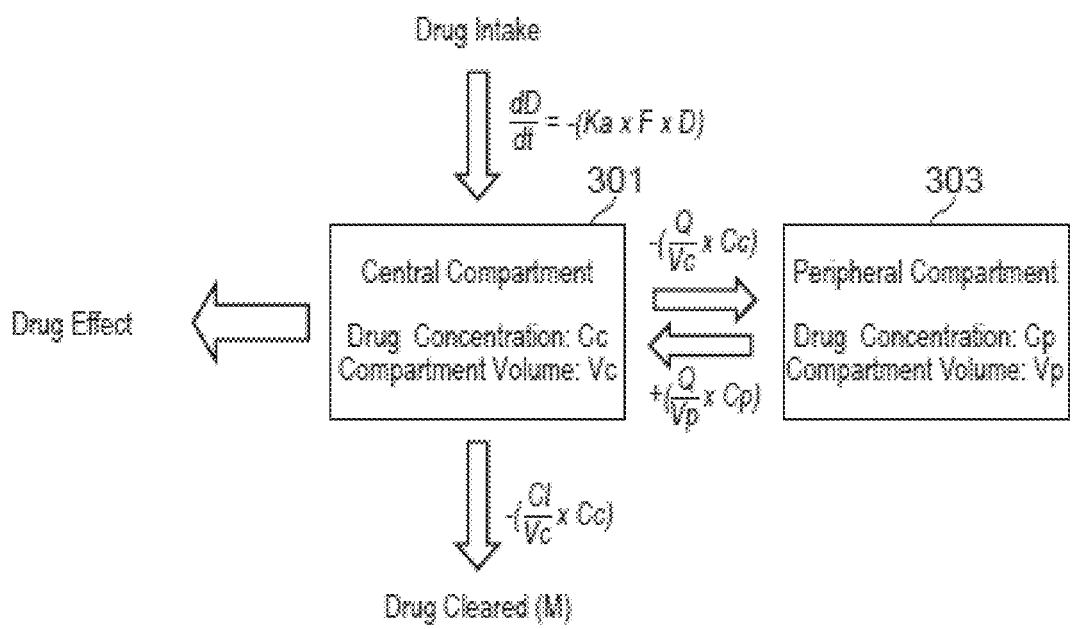
FIG. 3 illustrates an example two-compartment model that may provide a PK model according to one or more embodiments.

FIG. 3 illustrates an example two-compartment model that may provide the PK model according to one or more embodiments. A central compartment 301 has a central compartment drug concentration, Cc, (the drug plasma level in this example) and a central compartment volume, Vc. Drug intake to the central compartment 301 from the administered drug may be defined by:

$$dD/dt = -(ka \times F \times D) \quad \text{(Eq 1)}$$

where ka is a first order drug absorption rate constant; F is a relative bioavailability of the drug; and D is the drug dosage.

Drug clearance from the central compartment 301, for example via the kidneys, may be defined in terms of a change in central compartment concentration Cc:

$$dCc/dt = -(Cl/Vc \times Cc) \quad \text{(Eq 2)}$$

where Cl is the total body clearance of the drug from the central compartment. In some examples, Cc may be converted to a drug mass, M, cleared from the central compartment.

A peripheral compartment 303 may represent locations in the body in which the drug may reside as a depot and not necessarily provide a therapeutic effect. The peripheral compartment 303 has a peripheral compartment drug concentration, Cp, and a peripheral compartment volume, Vp. A rate of change of the peripheral compartment drug concentration, Cp, resulting from the flow of drug between the two compartments may be defined as:

$$dCp/dt = +(Q/Vc \times Cc) - (Q/Vp \times Cp) \quad \text{(Eq 3)}$$

where Q is an intercompartmental clearance between the central and peripheral compartments.

Combining everything together, the rate of change of the central compartment drug concentration, Cc, can be written as:

$$dCc/dt = +(ka/Vc \times F \times D) - (Cl/Vc \times Cc) - (Q/Vc \times Cc) + \quad \text{(Eq 4)}$$
$$(Q/Vp \times Cp)$$

Two compartmental models have been used to model plasma concentration for oral dosing of semaglutide. Two compartmental models have also been used to model plasma concentration for subcutaneous dosing of tirzepatide and Cagrisema [8]. Two compartmental models are more computationally intensive to solve due to the inter-dependent differential equations and typically perform modelling in an iterative time-step manner.

A single compartment model (volume of distribution Vd=Vc+Vp) results in simpler versions of equations 1 to 4 (peripheral component terms drop away). The simpler equations can be solved to provide explicit equations for plasma concentration, C:

Single dose:

$$C = \frac{F \cdot D \cdot k_a}{Vd(k_a - k_e)} \cdot \left(e^{-k_e \cdot t} - e^{-k_a \cdot t}\right) \quad \text{(Eq 5)}$$

Multi dose (steady state):

$$C = \frac{F \cdot D \cdot k_a}{Vd(k_a - k_e)} \cdot \left(\frac{e^{-k_e \cdot t}}{(1 - e^{-k_e \cdot \tau})} - \frac{e^{-k_a \cdot t}}{(1 - e^{-k_a \cdot \tau})}\right) \quad \text{(Eq 6)}$$

wherein C is the plasma concentration, Vd is the volume of distribution (Vd=Vc+Vp), ke is the elimination rate constant which relates to total body clearance (Cl) and Vd and τ is the dosing interval.

The two compartmental model can also yield explicit equations for the time of maximum concentration, tmax, and the average concentration at steady state, Cave:

$$t_{max} = \frac{\ln\left(\frac{k_a \cdot (1 - e^{-k_e \cdot \tau})}{k_e \cdot (1 - e^{-k_a \cdot \tau})}\right)}{(k_a - k_e)} \quad \text{(Eq 7)}$$

$$Cave = \frac{F \cdot D}{Cl \cdot \tau} \quad \text{(Eq 8)}$$

Estimated values of the specific parameters for the model can be obtained from one or more patient studies. For example, previous work by Overgaard et al [3] and Petri et al [4] determined values and expressions for F, Ka, Vc, Cl etc of a single compartment PK model using publicly available patient study data for subcutaneous semaglutide administration. Study data indicates individual characteristics can modulate the plasma level. As a result, the parameters F and/or Cl can be defined as a function of weight, sex, age, kidney function, race/ethnicity, type 2 diabetes history, water intake (oral), fasting time (oral) and injection site (subcutaneous). For example, the clearance can be expressed as:

$$Cl = Cl\_typ * E\_dose * E\_weight * \quad \text{(Eq 9)}$$
$$E\_sex * E\_age \ldots * E\_GFR * E\_T2D * E\_race * E\_ethnicity * E\_inj\_site$$

where Cl_typ is an average population value of the clearance, and the listed E factors respectively relate to the contribution from dose, weight, sex, age, glomerular filtration rate (GFR) (kidney function), type 2 diabetes, race, ethnicity and injection site. Weight is the dominant factor affecting drug clearance. 12% higher clearance has been observed in patients with Type 2 diabetes. Such PK models enable the calculation of a semaglutide plasma concentration as a function of time for a particular semaglutide dosage for a specific patient having personalised patient data including patient weight in particular.

As a further example, previous work published in the CDER Clinical Pharmacology Review for Tirzepatide (Mounjaro) [5] determined values and expressions for the Cl, Q, Vc, and Vp of a two-compartment PK model using patient study data for subcutaneous tirzepatide administration. Study data indicates individual characteristics can modulate the plasma level. As a result, Cl and Q can be defined as a function of body weight, while Vc and Vp can be defined as a function of fat mass (FM) and fat-free mass (FFM). The absorption rate constant (ka) may also be modified depending on whether the drug is administered as a lyophilised or solution formulation.

For example, the clearance can be expressed as:

$$Cl = Cl_{typ}\left(\frac{\text{body weight}}{70}\right)^{0.8} \quad \text{(Eq 11)}$$

where $Cl_{typ}$ is an average population value (or reference value) of the clearance.

The intercompartmental clearance between the central and peripheral compartments can be expressed as:

$$Q = Q_{typ}\left(\frac{\text{body weight}}{70}\right)^{0.8} \quad \text{(Eq 12)}$$

where $Q_{typ}$ is an average population value of the intercompartmental clearance between the central and peripheral compartments.

The volume of the central compartment can be expressed as:

$$Vc = Vc_{typ}\left(FFM + \frac{0.482 \cdot FM}{70}\right) \quad \text{(Eq 13)}$$

where $Vc_{typ}$ is an average population value of the volume of the central compartment.

The volume of the central compartment can be expressed as:

$$Vp = Vp_{typ}\left(FFM + \frac{0.482 \cdot FM}{70}\right) \quad \text{(Eq 14)}$$

where $Vp_{typ}$ is an average population value of the volume of the central compartment.

Values of fat-free mass can be estimated using a known approach such as the equations from Janmahasatian et al. [7], which take inputs of sex, body weight (BW) and BMI, as shown below:

$$FFM(\text{for males}) = \frac{9270 \cdot BW}{6680 + 216 \cdot BMI} \quad \text{(Eq 15)}$$

$$FFM(\text{for females}) = \frac{9270 \cdot BW}{8780 + 244 \cdot BMI} \quad \text{(Eq 16)}$$

Fat mass can then be estimated as the difference between body weight and fat-free mass.

Such PK models enable the calculation of a tirzepatide plasma concentration as a function of time for a particular tirzepatide dosage for a specific patient having personalised patient data including patient weight in particular.

As a further example, previous work [8] determined values and expressions for the Cl, Q, V etc of a PK model using patient study data, for subcutaneous administration of Cagrisema.

The study [8] evaluated the safety, tolerability, pharmacokinetics, and pharmacodynamics of the coformulation therapy, with a focus on bodyweight reduction, glycemic parameters, and hormonal changes.

The study measured mean values for the clearance (CL), volume of distribution (V), half-life ($t_{1/2}$), maximum concentration ($C_{max}$), and the area under the curve (AUC) for the coformulation.

PK models such as described in [8] enable the calculation of Cagrisema plasma concentration as a function of time for a particular Cagrisema coformulation dosage for a specific patient having personalised patient data including patient weight in particular.

More generally, similar compartment-based PK models can be provided for any incretin pathway drug, enabling calculation of plasma concentrations as a function of time for a particular dosage administered to a particular patient having personalised patient data including patient weight in particular.

Figure 4A:
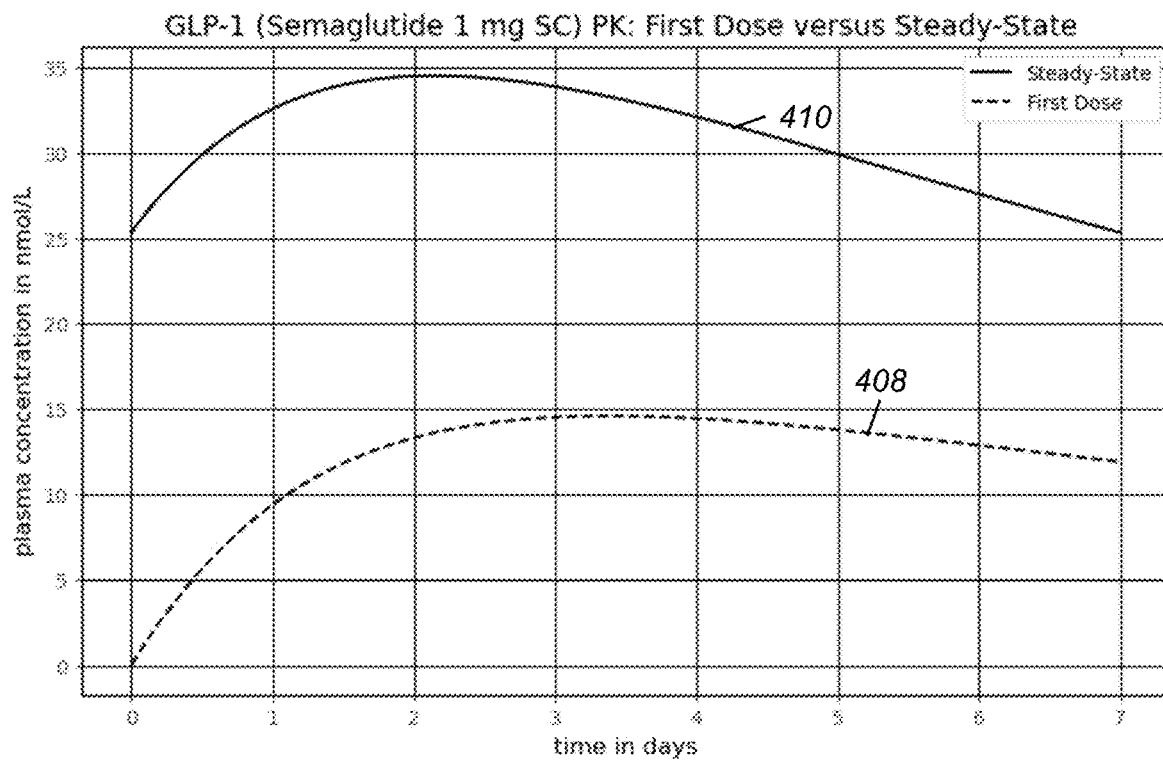
FIGS. 4A to 4C illustrate results from a PK model for subcutaneous administration of semaglutide according to an embodiment of the present disclosure.
Figure 4B:
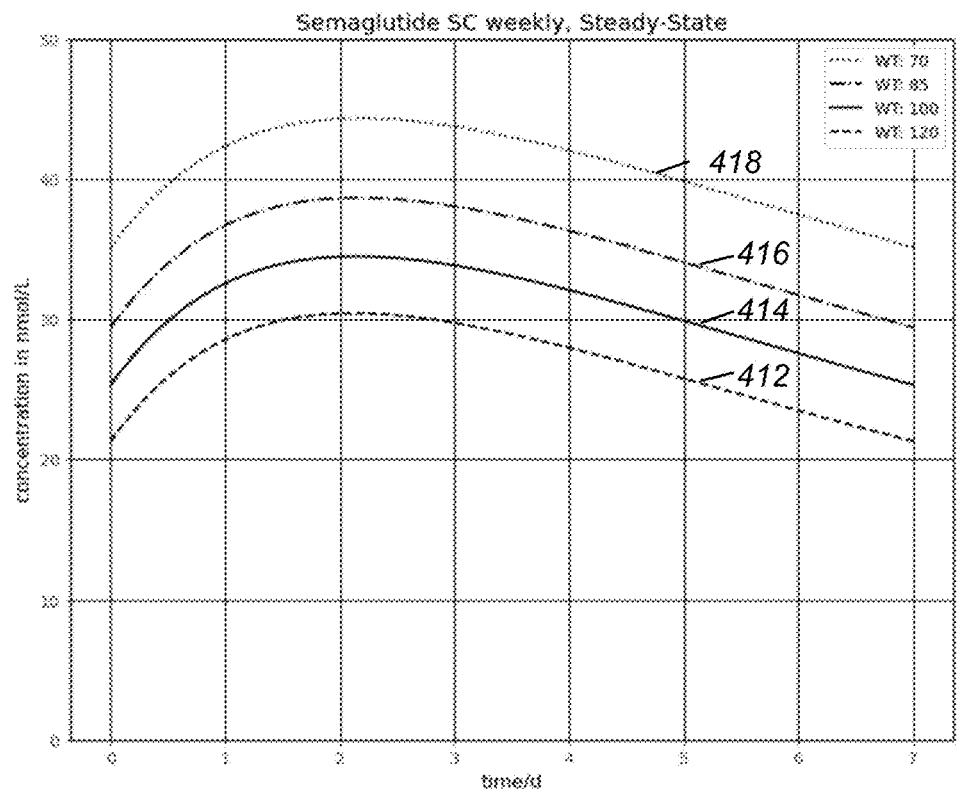
Figure 4C:
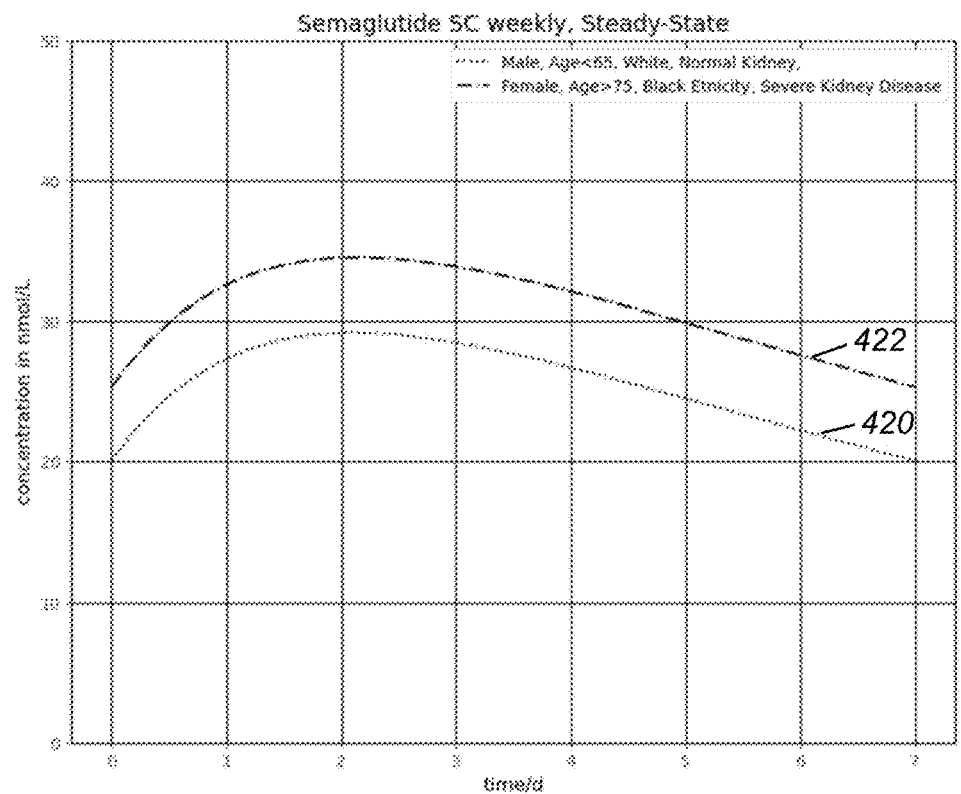

FIGS. 4A to 4C illustrate results from a PK model for subcutaneous administration of semaglutide according to an embodiment of the present disclosure. A single compartmental PK model was developed to produce the results and used parameter values from Overgaard [3] (see Annex).

FIG. 4A illustrates variation in plasma concentration over the course of 7 days (the typical administration frequency for subcutaneous semaglutide). A first plot 408 shows plasma concentration in the 7 days immediately following administration of a single 1.0 mg dose (determined using equation 5 above). A second plot 410 shows plasma concentration at steady state after the administration of multiple 1.0 mg doses at 7-day intervals (determined using equation 6 above). In practice, steady-state is reached after approximately 20 days with weekly administration of a constant dose. The figure illustrates that drug accumulation in the plasma occurs over several weeks and the drug therefore takes such time to provide a maximum effect on satiety.

FIG. 4B illustrates the variation in steady state plasma concentration as a function of weight (determined using equation 6 with weight variation applied via equation 9). Four plots are shown to illustrate patients with identical patient data other than patient weight. A first plot 412 illustrates steady-state plasma concentration after administration of multiple 1.0 mg doses of subcutaneous semaglutide at 7-day intervals for a patient with a weight of 120 kg. A second plot 414 illustrates steady-state plasma concentration after administration of multiple 1.0 mg doses of subcutaneous semaglutide at 7-day intervals for a patient with a weight of 100 kg. A third plot 416 illustrates steady-state plasma concentration after administration of multiple 1.0 mg doses of subcutaneous semaglutide at 7-day intervals for a patient with a weight of 85 kg. A fourth plot 418 illustrates steady-state plasma concentration after administration of multiple 1.0 mg doses of subcutaneous semaglutide at 7-day intervals for a patient with a weight of 70 kg. The plots illustrate weight as the primary driver of inter-patient variability in semaglutide plasma concentration.

FIG. 4C illustrates the variation in steady state plasma concentration as a function of parameters of patient data other than weight (determined using equation 6 with parameter variation applied via equation 9). A first plot 420 and a second plot 422 both illustrate steady-state plasma concentration after administration of multiple 1.0 mg doses of subcutaneous semaglutide at 7-day intervals for a patient with a weight of 85 kg. However, the first plot 420 is for a male patient, who is white, has a normal kidney function metric (GFR (glomerular filtration rate)), less than 65 years of age and injects the semaglutide in his upper arm. The second plot 422 is for a male patient, who is black African, has a severe impairment kidney function metric (GFR (glomerular filtration rate)), is over 75 years of age and injects the semaglutide in his thigh. The plots illustrate that the secondary patient data parameters (i.e. those other than weight) can result in a significant difference in plasma level concentration between the two patients for the same administered dosage.

The second plot 410 of FIG. 4A and FIGS. 4B and 4C illustrate steady plasma concentrations for a fixed dose, D. This fixed dose, D, may be the maximum dose or maintenance dose at the end of a dosage ramp profile. In some examples, the dosage ramp profile may be implemented in the model by defining the dose, D, as a step-wise function dependent on time, t, corresponding to the ramped increase in dosage amounts (e.g. as defined in table 1 above). The time dependent change in plasma level can then be modelled through repetitive application of equation 5.

Figure 4D:
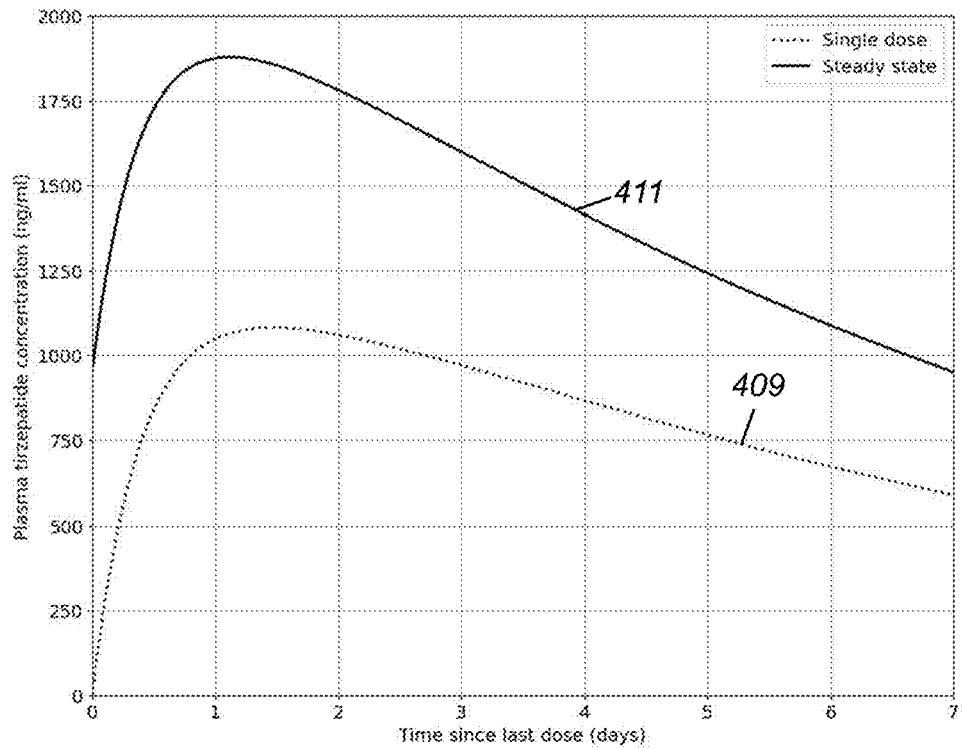
FIGS. 4D to 4F illustrate results from an example PK model for subcutaneous administration of tirzepatide.
Figure 4E:
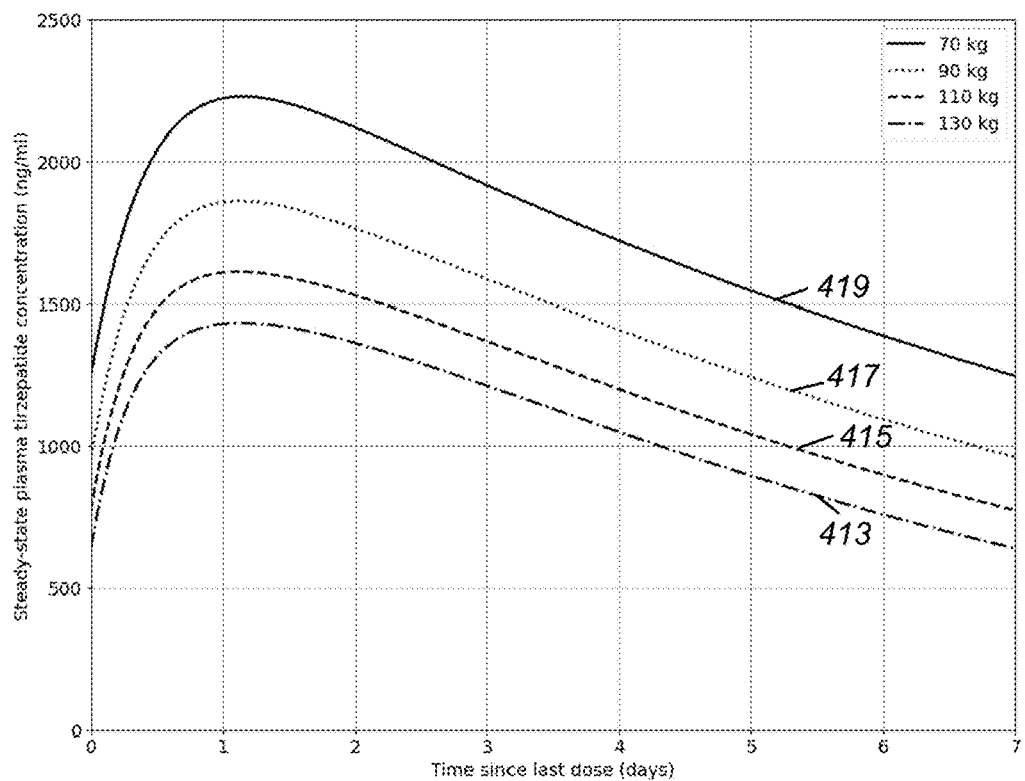
Figure 4F:
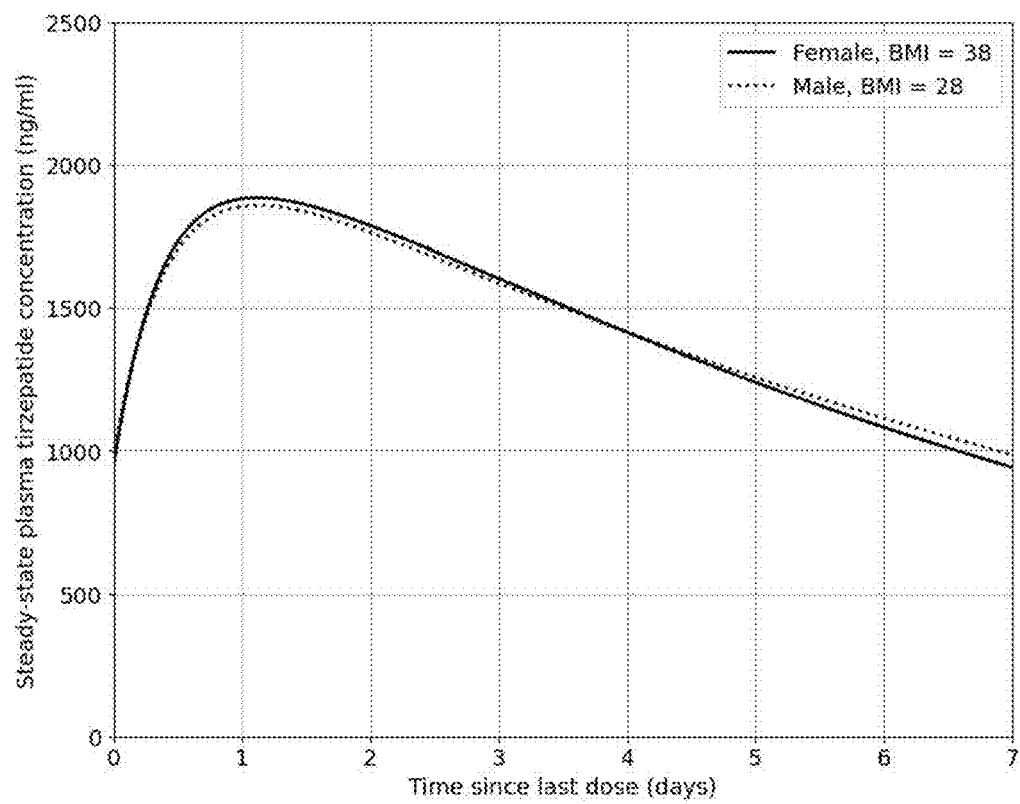

FIGS. 4D to 4F illustrate results from a PK model for subcutaneous administration of tirzepatide according to an embodiment of the present disclosure. A two compartmental PK model was developed to produce the results and used parameter values from [ref].

FIG. 4D illustrates variation in plasma concentration over the course of 7 days (the typical administration frequency for subcutaneous tirzepatide). A first plot 409 shows plasma concentration in the 7 days immediately following administration of a single 15.0 mg dose (determined using equations 1-4 and 11-16 above). The patient was a female individual weighing 89.4 kg and with a BMI of 32.1 kg/m$^2$. A second plot 411 shows plasma concentration at steady state after the administration of multiple 15.0 mg doses of tirzepatide at 7-day intervals (determined using equations 1-4 and 11-16 above) for the same patient. In practice, steady-state is reached after approximately 20 days with weekly administration of a constant dose. The figure illustrates that drug accumulation in the plasma occurs over several weeks and the drug therefore takes such time to provide a maximum effect on satiety.

FIG. 4E illustrates the variation in steady state plasma concentration as a function of weight (determined using equations 1-4 and 11-16 above). Four plots are shown to illustrate patients with identical patient data other than patient weight. A first plot 413 illustrates steady-state plasma concentration after administration of multiple 15.0 mg doses of subcutaneous tirzepatide at 7-day intervals for a female patient with a weight of 130 kg and a BMI of 32.1 kg/m$^2$. A second plot 415 illustrates steady-state plasma concentration after administration of multiple 15.0 mg doses of subcutaneous tirzepatide at 7-day intervals for a female patient with a weight of 110 kg and a BMI of 32.1 kg/m$^2$. A third plot 417 illustrates steady-state plasma concentration after administration of multiple 15.0 mg doses of subcutaneous tirzepatide at 7-day intervals for a female patient with a weight of 90 kg and a BMI of 32.1 kg/m$^2$. A fourth plot 419 illustrates steady-state plasma concentration after administration of multiple 15.0 mg doses of subcutaneous tirzepatide at 7-day intervals for a patient with a weight of 70 kg and a BMI of 32.1 kg/m$^2$. The plots illustrate weight as the primary driver of inter-patient variability in tirzepatide plasma concentration.

FIG. 4F illustrates the variation in steady state plasma concentration as a function of parameters of patient data other than weight. A first plot 420 and a second plot 422 both illustrate steady-state plasma concentration after administration of multiple 15.0 mg doses of subcutaneous tirzepatide at 7-day intervals for a patient with a weight of 89.4 kg. However, the first plot 421 is for a male patient, with a BMI of 28 kg/m$^2$. The second plot 423 is for a female patient with a BMI of 38 kg/m$^2$. The plots illustrate that secondary patient data parameters, such as sex, can result in plasma level differences between the two patients for the same administered dosage.

Figure 4G:
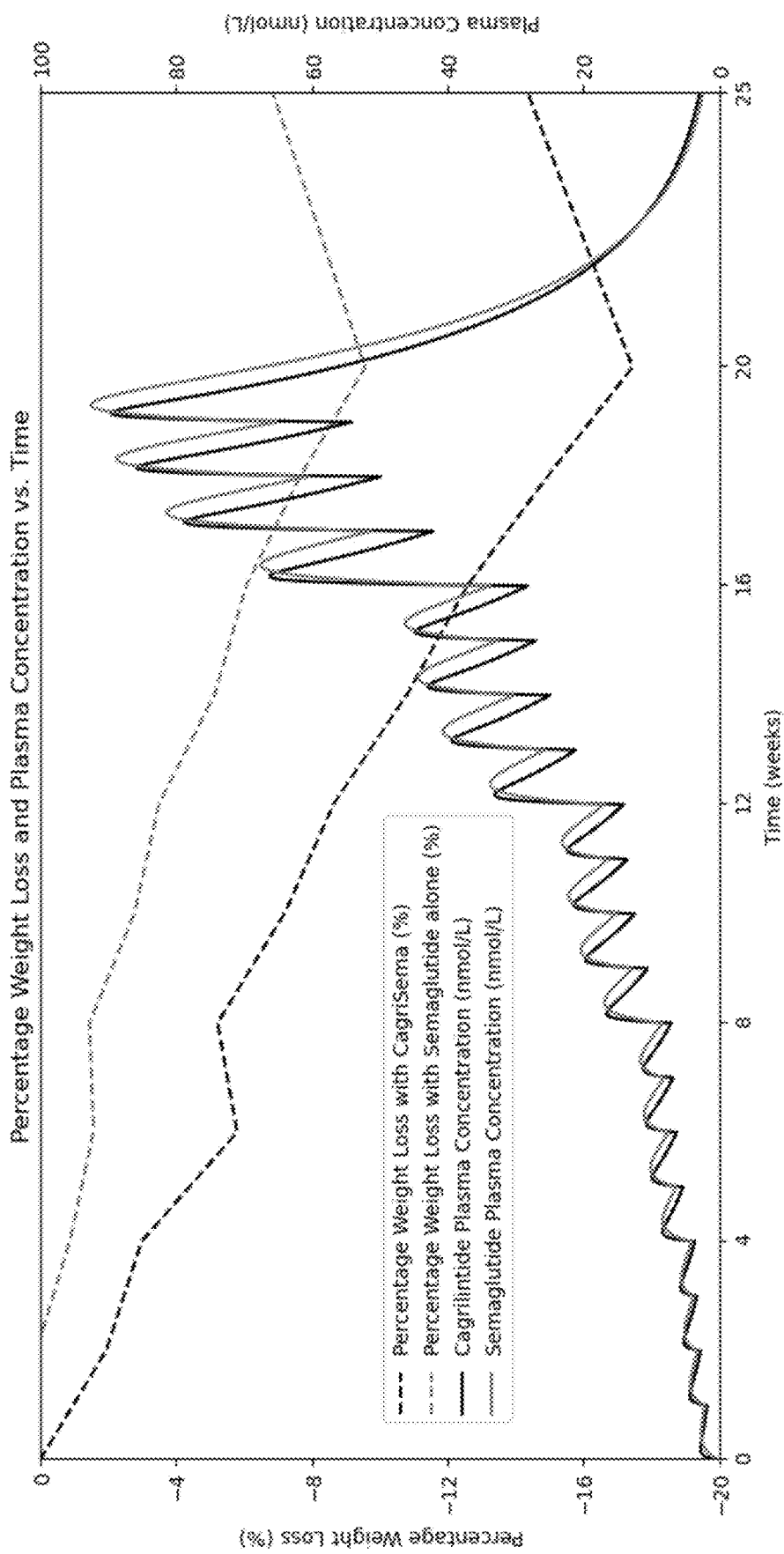
FIG. 4G shows a plot of plasma concentration for Cagrisema coformulation over a treatment titration.

FIG. 4G shows a plot of plasma concentration for the Cagrisema coformulation over a treatment titration derived from data from [8]. Cagrisema is titrated every 4 weeks until the coformulation components (cagrilintide and semaglutide) reach a maximum dose of 2.4 mg. After Week 20 patients were removed from treatment.

For all PK models, the fixed dose, D, may be the maximum dose or maintenance dose at the end of a dosage ramp profile. In some examples, the dosage ramp profile may be implemented in the model by defining the dose, D, as a stepwise function dependent on time, t, corresponding to the ramped increase in dosage amounts (e.g. as defined in table 1 above). The time dependent change in plasma level can then be modelled through repetitive application of equations 1-4 and 11-16.

Therefore, the PK model can calculate plasma levels based on the dosage and patient data. The patient data includes the dominant parameter patient weight. The patient data can also include one or more secondary patient data parameters. The secondary parameters are dependent parameters of the PK model. The secondary parameters may include one or more of: a patient age; a patient ethnicity; a patient gender; a patient diabetes history; a kidney function metric; a treatment purpose; a dosage route; a pharmacogenomic profile; and a patient medication list.

The treatment purpose may include treatment of obesity and/or treatment of diabetes.

A pharmacogenomic profile, or more generally a phenotype, may provide an indication of the responsiveness of a patient to semaglutide, tirzepatide, Cagrisema or incretin drugs more generally. Examples of phenotypes include: (a)"hungry brain," characterized by excessive calories consumed before eating is terminated; (b) "emotional hunger," characterized by emotional eating and reward-seeking, in the face of otherwise normal homeostatic eating behaviours (39); (c) "hungry gut," characterized by reduced duration of fullness, quantified objectively by rapid gastric emptying; and (d) "slow burn," characterized by reduced REE, physical activity, exercise and muscle mass. People with a "hungry gut", who tend to get hungry in between meals, have been shown to respond best to GLP1 agonists. These patients may have low levels of naturally occurring GLP1 hormones which may be a cause of obesity and/or type 2 diabetes. As a result, such patients can have an above average response to GLP1 agonists.

The dosage route may comprise an oral dosage, a subcutaneous dosage or any other dosage route that is used or may be used in future (e.g. intramuscular injection, topical, rectal etc.). Although oral dosage is only licensed for diabetes, it is expected to be approved for obesity in future and the present disclosure encompasses oral dosing for obesity. Oral dosing may be preferred for obesity because it reinforces behavioural control. When the dosage route is oral dosage, additional secondary parameters can include fasting time data relating to a prescribed fasting time prior to dosage administration and water intake data relating to a volume of water to be taken with the dosage. Both fasting time and water intake affect the bioavailability, F, of the orally administered drug. When the dosage route is oral dosage, a two-compartment PK model may be used. When the dosage route is subcutaneous dosage, an additional secondary parameter can include injection site at which the drug is administered. When the dosage route is subcutaneous dosage, a one-compartment PK model may be used.

A dosage calculator derived from the PK model can therefore enable the method to determine an initial dosage based on the target plasma level (or target end point (target weight loss, target glycemic control, target side effect)) and the patient data. As noted above, the initial dosage may correspond to a steady-state maintenance dosage at the end of an initial stepwise ramp profile. In this way, the initial dosage may comprise a first estimate of the maintenance dosage at the end of the initial dose titration.

Dosage Calculator Example 1

In some examples, the dosage calculator may implement the PK model itself utilising the relevant equations above (e.g. equations 1-4 for a two-compartment model and equations 6 and 9 for a single compartment model) and the patient data parameter dependencies. The dosage calculator may then proceed according to the method of FIG. 12, which illustrates a method of determining a dosage for administering to a patient according to an embodiment of the present disclosure.

A first step 1224 comprises receiving the target plasma level. As described above, the target plasma level may comprise an ideal therapeutic level or may be determined from the relevant drug effect to plasma concentration relationship (e.g. FIG. 2A or 2B for semaglutide).

A second step 1226 comprises setting an initial value of an initial dosage estimate. The initial value may comprise an average dosage for the patient population.

A third step 1228 comprises processing the initial dosage estimate and the patient data with the dosage calculator (PK model) to determine a predicted plasma level. The predicted plasma level may comprise the average plasma level over a dosing interval at steady state, Cave, a trough plasma level, Ctrough, a maximum plasma level, Cmax, an area under the blood curve (Cauc) of a plasma level time profile or any other suitable plasma level metric.

A fourth step 1230 comprises comparing the predicted plasma level to the target plasma level. The target plasma level may comprise the same metric (trough level, Cmax, Caverage, Cauc, etc) as the predicted plasma level.

A fifth decision step 1232 comprises determining if a difference in the values of the predicted plasma level and the target plasma level is within a difference threshold. If not the method proceeds to a sixth step 1234 and refines the initial dosage estimate, before returning to the third step 1228.

If the difference in the two values is within the difference threshold, the method proceeds to a seventh step 1236 and outputs or indicates the initial dosage estimate as the initial dosage for administering to a patient.

In some examples, the loop around the third to sixth steps 1228-1234 may be performed in an iterative fashion until the values are within the difference threshold. In some examples, the loop may be performed at least two times and a dosage value corresponding to the target plasma level may be interpolated. In some examples, the loop may correspond to an optimisation routine.

If using a two-compartment model (e.g. for oral administration), the first dosage calculator example can require a lot of processing power for the third step 1228 of calculating the predicted plasma level using the piecewise time-step differential equations of the PK model (equations 1 to 4). Therefore, the first dosage calculator example can be particularly suited to single-compartment PK models which require less processing power (e.g. equations 6 or 8). However, the first dosage calculator can also be used with (more accurate) two-compartment PK models to generate relationship data between the various patient data parameters, dosage and predicted plasma level/weight loss/glycemic control. Such a relational mapping may take the form of a look-up table, a nomogram, an analogue computer or the like. For example, a detailed relational mapping can be determined over a long time frame (hours, days, months) by performing the method of FIG. 12 for a population set of different patient data. The resulting output can provide a detailed mapping between target plasma level and starting dose for a range of the key patient data variables (e.g. weight, age, ethnicity, kidney function etc). The relational mapping (e.g. look-up tables) can provide one or more of: (i) a more efficient dosage calculator (see Dosage Calculator Example 3) for deploying at scale to patients and clinicians (i.e. quick dosage calculation for patient/HCP); (ii) a training data set for a ML dosage calculator (see Dosage Calculator Example 4); (iii) the foundations of a clinical guidelines reference; and (iv) standard dosing regimens for incretin pathway drug products such as semaglutide products, regulatory labelling, packaging etc.

Figure 12:
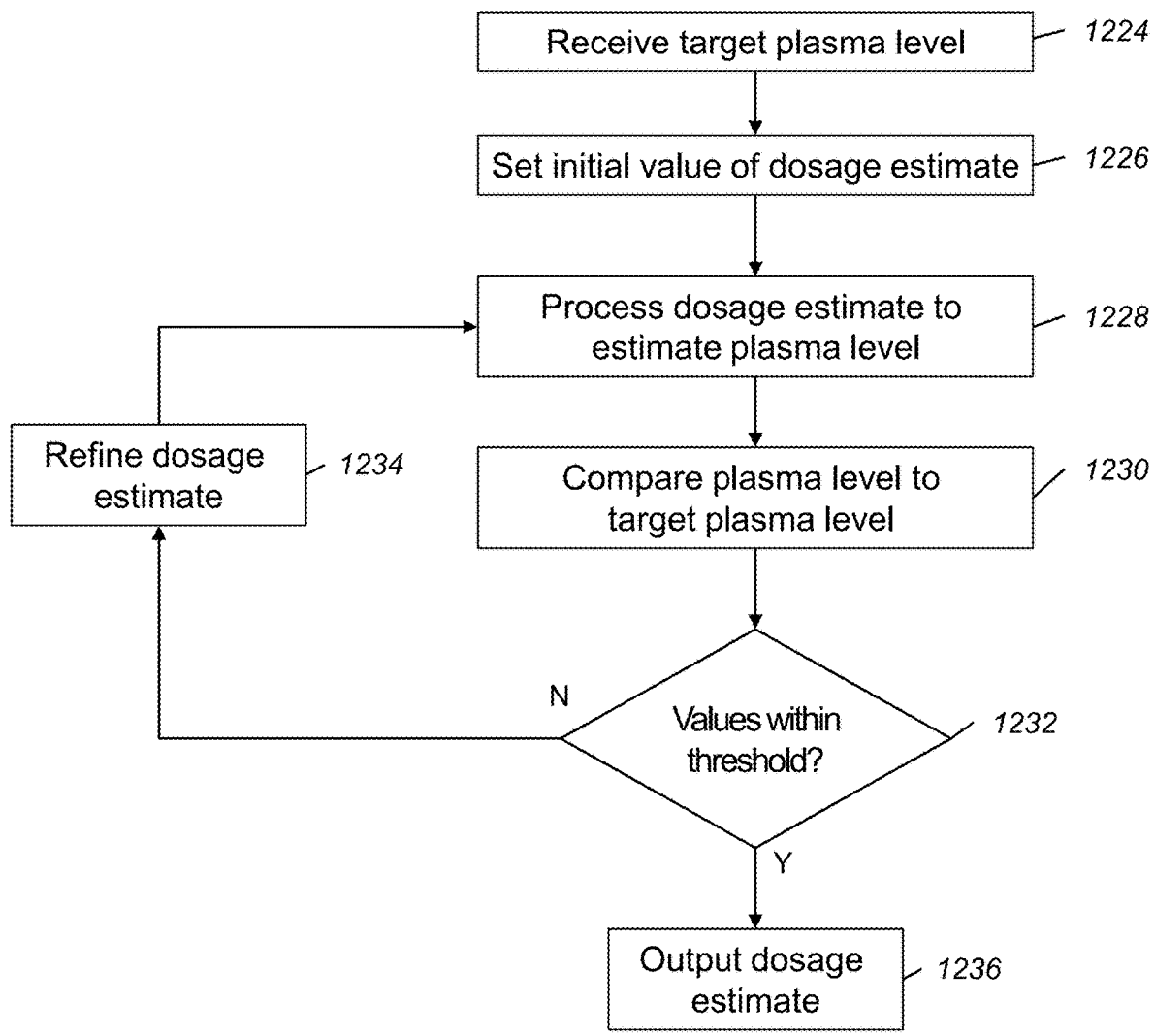
FIG. 12 illustrates a method of determining a dosage for administering to a patient according to an embodiment of the present disclosure.

In some examples, the first dosage calculator may operate without the iterative loop of FIG. 12. For example, the target plasma level may comprise the average plasma concentration (over the dosing interval), Cave, during the maintenance treatment phase. The target plasma level may be set in the same way as described above, for example based on a predetermined relationship. The initial (maintenance) dosage can then be estimated according to relationship between dose and average plasma concentration defined by equation 8 above and rearranged as:

$$D = \frac{C_{average} \cdot CL \cdot \tau}{F}$$

A personalised clearance can be determined based on the patient data, using equation 9 or 11, for example. F is the bioavailability and in some examples may be modified by one or more patient data parameters and/or the dosage. $\tau$ is the dosing interval. Therefore, a method may comprise: (i) setting a target plasma level as a target average plasma concentration; (ii) determining a personalised clearance value based on the patient data; (ii) determining or receiving a bioavailability optionally comprising determining a personalised bioavailability; (iv) receiving a dosing interval; and (iv) determining an initial (maintenance) dosage based on the target average plasma concentration, the personalised clearance value, the bioavailability and the dosing interval. In some examples, the target plasma level may be set as a target area under the curve ($C_{AUC}$). In such examples, the method may comprise determining a target average plasma concentration, Cave, from the $C_{AUC}$ by dividing $C_{AUC}$ by the time period (e.g. the number of hours) over which it is recorded (e.g the dosing interval). This method avoids the need for the iterative loop of FIG. 12 providing a faster processing solution.

Dosage Calculator Example 2

When the target end point includes a target weight loss (i.e. the semaglutide is administered for obesity), a further level of sophistication for calculating a drug dose for a target weight loss may utilise a second example dosage calculator derived from a PKPD model that incorporates the effect of drug dosage on daily energy intake (EI) and total daily energy expenditure (TDEE). In particular, the dosage calculator may use a EI/TDEE model in place of the fixed relationship of FIG. 2A enabling a personalised dosage calculator that includes a personalised metabolism model.

Figure 17:
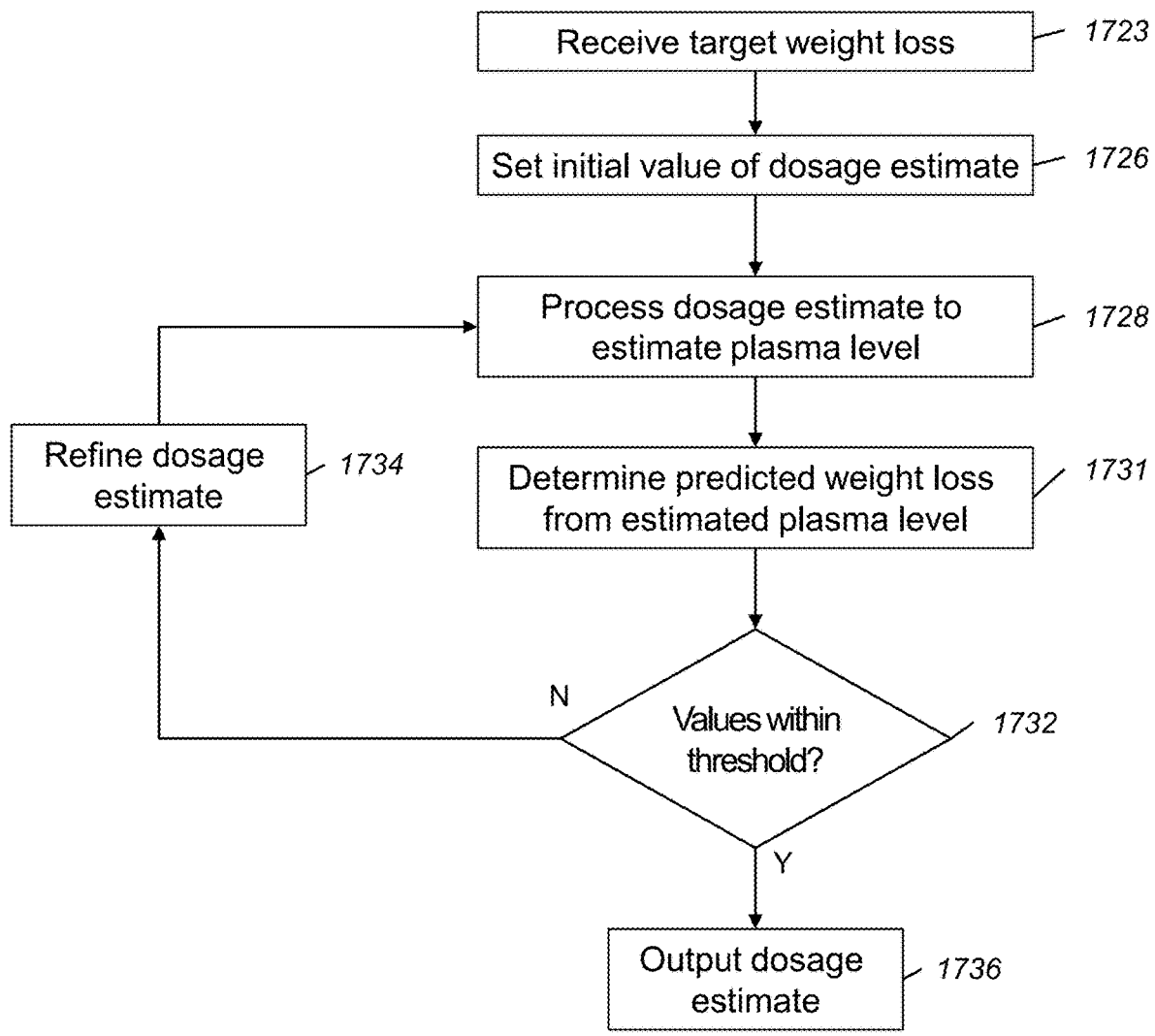
FIG. 17 illustrates a method of determining a dosage for administering to a patient according to an embodiment of the present disclosure.
Figure 18A:
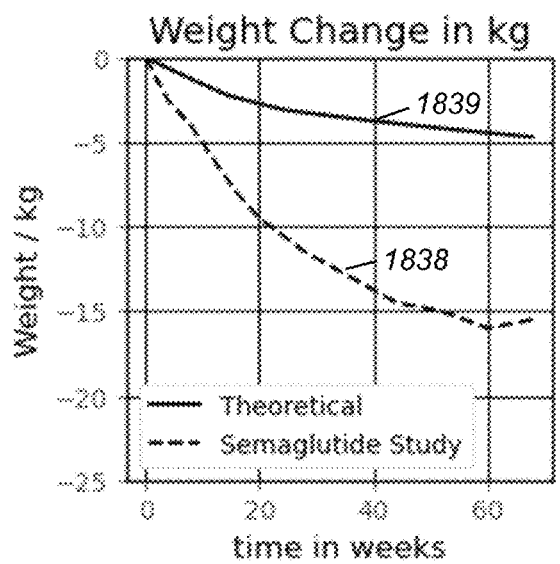
FIGS. 18A to 18D illustrate the predicted weight loss profiles for different doses of semaglutide using an example PKPD model according to an embodiment of the present disclosure.
Figure 18B:
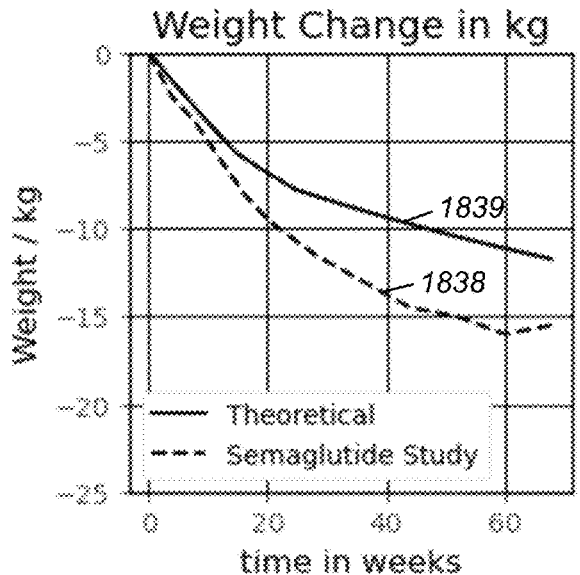
Figure 18C:
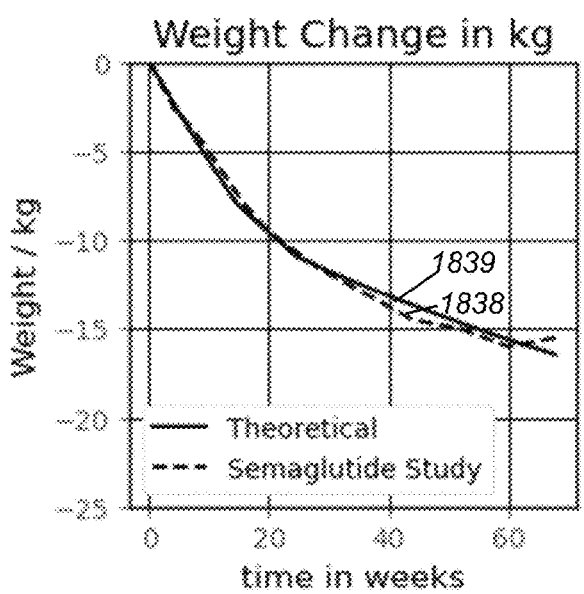
Figure 18D:
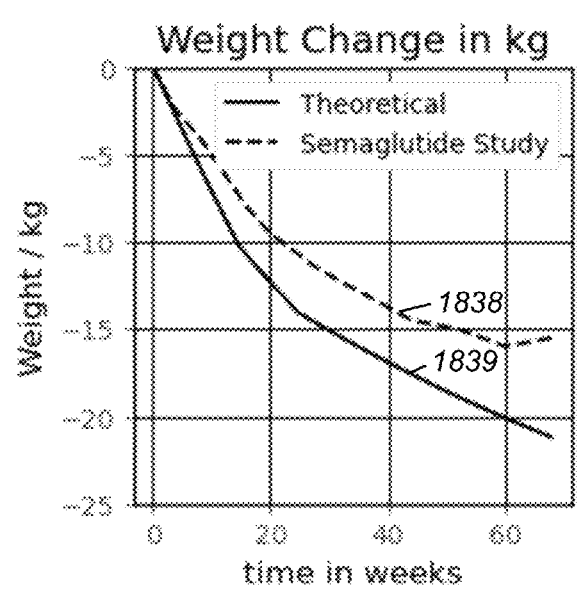
Figure 18E:
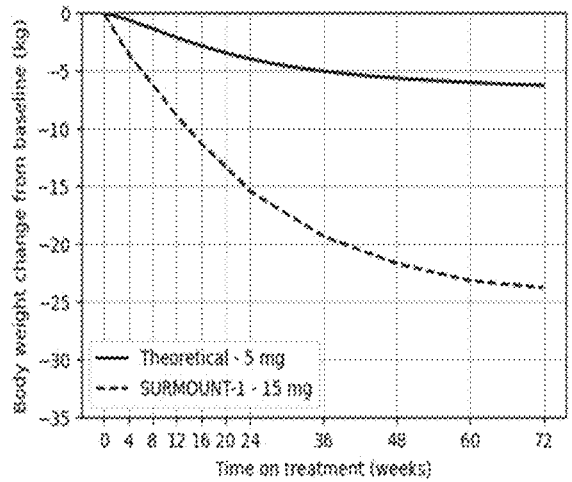
FIGS. 18E to 18H illustrate the predicted weight loss profiles for different doses of tirzepatide using an example PKPD model according to an embodiment of the present disclosure.
Figure 18F:
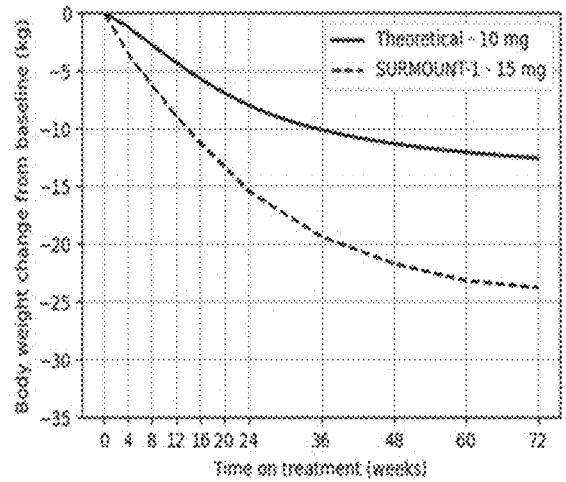
Figure 18G:
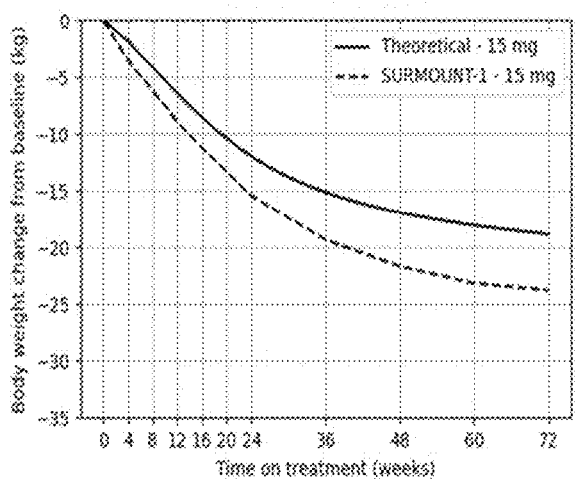
Figure 18H:
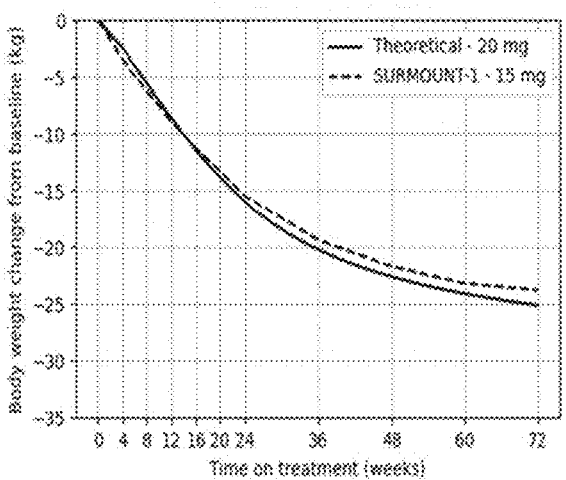

The dosage calculator may proceed according to the method of FIG. 17, which is similar to that of FIG. 12 and illustrates a method of determining a dosage for administering to a patient according to an embodiment of the present disclosure.

A first step 1723 comprises receiving the target weight loss.

A second step 1726 comprises setting an initial value of an initial dosage estimate. The initial value may comprise an average dosage for the patient population.

A third step 1728 comprises processing the initial dosage estimate and the patient data with the dosage calculator (e.g. the single compartment PK model described above) to determine a predicted plasma level. The predicted plasma level may comprise the average plasma level over a dosing interval at steady state, Cave, a trough plasma level, Ctrough, a maximum plasma level, Cmax, or any other suitable plasma level metric.

A fourth step 1731 comprises determining a predicted weight loss based on the estimated plasma level. The fourth step may comprise determining the predicted weight loss using an EI or EI/TDEE model, an example of which is described below.

A fifth decision step 1732 comprises determining if a difference in the values of the predicted weight loss and the target weight loss is within a difference threshold. If not the method proceeds to a sixth step 1734 and refines the initial dosage estimate, before returning to the third step 1728.

If the difference in the two values is within the difference threshold, the method proceeds to a seventh step 1736 and outputs or indicates the initial dosage estimate as the initial dosage for administering to a patient.

In some examples, the loop around the third to sixth steps 1728-1734 may be performed in an iterative fashion until the values are within the difference threshold. In some examples, the loop may be performed at least two times and a dosage value corresponding to the target weight loss may be interpolated. In some examples, the loop may correspond to an optimisation routine.

In relation to the fourth step 1731, the dosage calculator may: determine an EI deficit profile based on the estimated plasma level; and determine a weight loss based on the EI deficit profile using an EI or EI/TDEE model.

In some examples, the dosage calculator may determine the EI deficit profile for any individual patient, $EI_{def}(t)$, based on their estimated plasma level by scaling a predetermined population-average EI deficit profile, $EI_{def0}(t)$ based on a ratio of the estimated plasma level, Cave, to a predetermined population-average plasma level, $Cave_0$:

$$EI_{def}(t) = \frac{Cave}{Cave_0} \cdot EI_{def0}(t) \quad \text{(Eq 10)}$$

Figure 14:
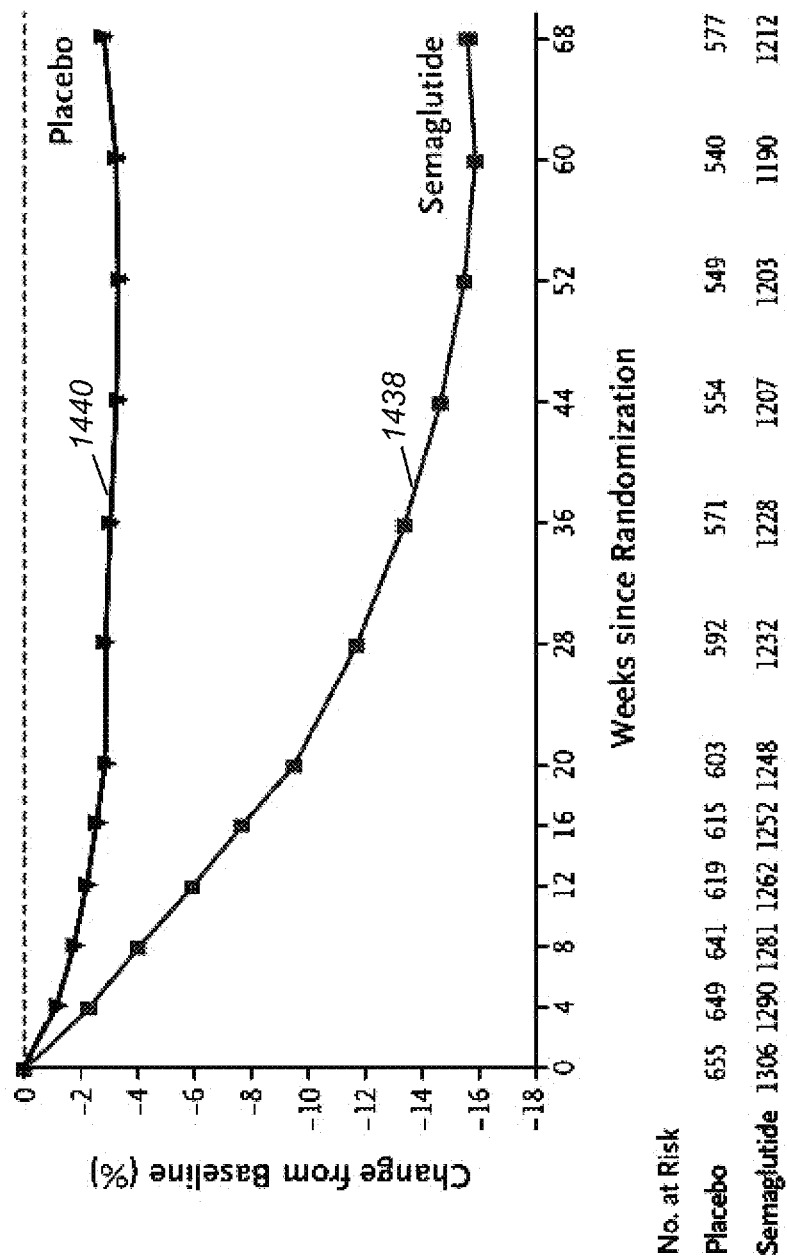
FIG. 14 illustrates weight loss trajectory for an average participant in a semaglutide study.

In some examples, the predetermined population-average EI deficit profile, $EI_{def0}(t)$ and the predetermined population-average plasma level, $Cave_0$, may be determined from patient study data. FIG. 14 illustrates publicly available patient study data from the STEP trial for subcutaneous semaglutide administration. The Figure illustrates the weight loss trajectory for patients with a maximum dosage of 2.4 mg subcutaneous semaglutide 1438 and patients taking a placebo 1440 during the study. The general exponential decay like profile illustrated in the Figure has also been reported for different dosages with the different dosage resulting in a different equilibrium weight (higher dosages result in lower equilibrium weight/greater weight loss). The published trajectory of weight loss is the weight loss trajectory for an average participant in the study with average circulating drug concentrations. The average participant had a mean body weight of 106 kg, body mass index (BMI) 38.5, age 47.3, (predominantly) female and was white. Similar patient study data to that of FIG. 14 was obtained in the SURMOUNT-1 trial for subcutaneous tirzepatide administration [5] and the study [8] for Cagrisema.

The average weight loss trajectory can be converted to an estimated population-average energy intake deficit profile, $EI_{def0}(t)$, using an EI/TDEE model such as that outlined below. In some examples, a population-average EI deficit profile for a specific dosing regimen may be determined using the equation:

$$EI_{def0}(t) = \left(\frac{E_{max} \cdot \text{dose}}{EC50 + \text{dose}}\right) \cdot e^{-kt} + \text{MinEffect} \quad [\text{Eq 17}]$$

Values of Emax, EC50, k, and MinEffect may be estimated from the observed population-average weight loss trajectory (FIG. 15A) on a specific dosing regimen. The time since the start of treatment (not just the start of the current dose) is denoted by t. Different combinations of values of Emax, EC50, k, and MinEffect can be trialed in Equation 27 to calculate a proposed population-average EI deficit profile when following the specific dosing regimen. The proposed population-average EI deficit profile can be used in the EI/TDEE model to calculate a proposed weight loss trajectory. The patient data used in the EI/TDEE model can be the average values associated with the patients used to generate the observed population-average weight loss trajectory. The proposed population-average weight loss trajectory (as predicted by the EI/TDEE model using the trialled values of Emax, EC50, k, and MinEffect) can then be compared with the observed population-average weight loss trajectory (e.g. for the 15 mg maintenance dose group in SURMOUNT-1), and a metric can be calculated to represent how well the proposed trajectory fits the observed trajectory (e.g. mean squared error (MSE) at designated time points). In this way, many combinations of values of Emax, EC50, k, and MinEffect can be trialed and the combination of values that produces the proposed population-average weight loss trajectory that best fits (e.g. has the smallest MSE) the observed population-average weight loss trajectory can be selected. In this way, equation 17 can be used to predict the energy deficit profile at any time point for the "average" individual when following a specific dosing regimen, once values of Emax, EC50, k, and MinEffect have been established.

Figure 15A:
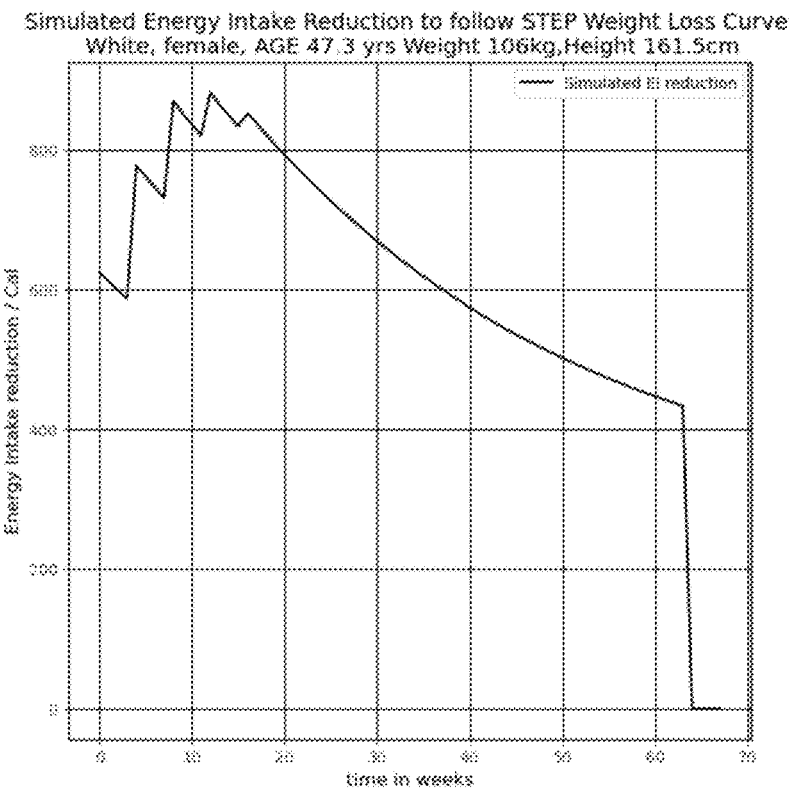
FIG. 15A illustrates the equivalent calorie reduction calculated to produce the weight loss profile of FIG. 14.
Figure 15B:
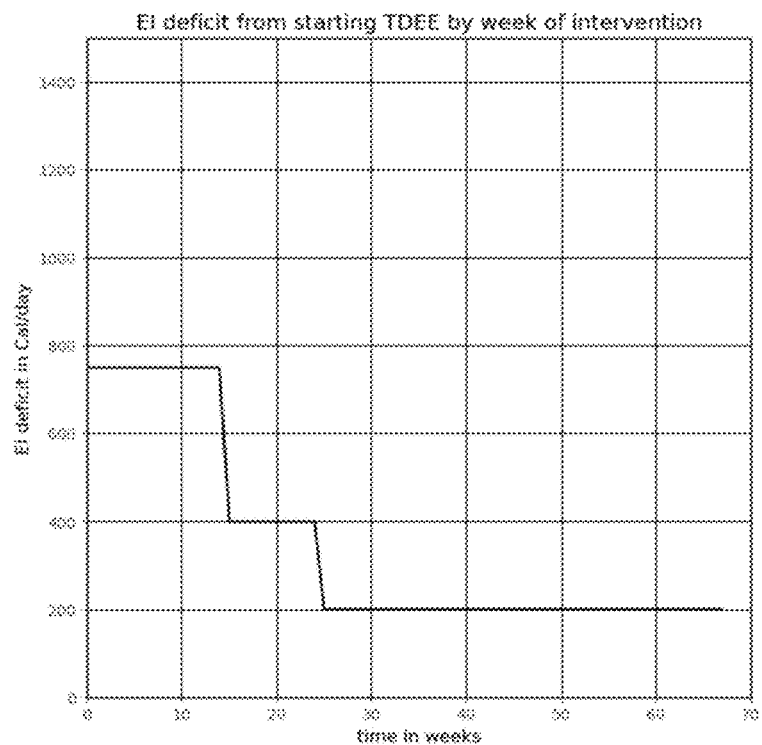
FIG. 15B illustrates a step-wise simplification of FIG. 15A.

FIG. 15A illustrates the population-average energy intake deficit profile, $EI_{def0}(t)$, (i.e. calorie restriction) calculated to produce the average weight loss profile of the average participant of FIG. 14. Energy intake values were found that provided a predicted weight loss with the best fit to the plot of FIG. 14 using the average participant data in the EI-TDEE model outlined below (see pseudo code). In some examples, the population-average energy intake deficit profile, $EI_{def0}(t)$, may be simplified into a step wise profile as illustrated in FIG. 15B, enabling simpler onward calculation.

The predetermined population-average plasma level, $Cave_0$, may be taken straight from the study data for the average participant or can be calculated using the PK model and the patient data parameters of the average participant (e.g. using equations 8 and 9 above).

Although equation 10 uses a linear scaling based on $Cave/Cave_0$, other examples may use a non-linear scaling e.g. to represent the logarithmic relationship of FIG. 2A or a sigmoidal relationship.

Following determination of EI deficit profile for any individual patient, $EI_{def}(t)$, the dosage calculator can determine a predicted weight loss for the individual by processing the EI deficit profile with the EI/TDEE model. The EI/TDEE model may output a weight loss trajectory based on the EI deficit profile. In some examples, the EI/TDEE model may output a weight loss trajectory based on the EI deficit profile and parameters of the patient data. As an example, the following is pseudo code (based on [6]) for estimating a time dependent weight profile as a function of TDEE, initial weight, height, age, sex and a time dependent energy intake profile:

def weight_prediction(TDEE_0, Weight_0, Height, AGE, SEX, $t$, $EI$):

$m = (0.9 * \text{TDEE\_0} - 10 * \text{Weight\_0} -$ $6.25 * \text{Height} + 5 * \text{AGE} - 166 * \text{SEX} + 161)/\text{Weight\_0}$ $y = -6.25 * \text{Height} + 5 * \text{AGE} - 166 * \text{SEX} + 161$ $\text{Alpha} = -(m + 10)/7700$ $\text{Beta} = (0.9 * EI + y)/7700$ $C = \text{Weight\_0} + \text{Beta}/\text{Alpha}$ $\text{Weight\_t} = -(\text{Beta}/\text{Alpha}) + C * np.\exp(\text{Alpha} * t)$ return(Weight_t, $EI$)

The above code calculates a weight at a particular time, t, based on the value of EI at that time t. A time dependent weight profile can be obtained by determining the weight for a range of values of t. TDEE may be calculated using the pseudo code for determining the resting metabolic rate (RMR) which may be calculated as:

```
def RMR_calc(Weight, Age, TDEE_ratio):
  if SEX == 0:
    RMR = (248 * (Weight ** 0.4356)) - (5.09 * Age)
  else:
    RMR = (293 * (Weight ** 0.4330)) - (5.92 * AGE)
  TDEE = TDEE_ratio*RMR #kcal/day baseline energy requirements per day
  return(RMR, TDEE)
``` where TDEE_ratio is fractional ratio of physical activity to resting metabolic rate. TDEE may also be calculated by additionally accommodating additional thermogenesis which may be stimulated by the incretin pathway drug/semaglutide. The thermogenesis may be a small amount of energy but contributes to the satiation effect of the drug. Additionally exposure to cold environments and other factors can increase energy spent in thermogenesis. TDEE accounting for thermogenesis may be calculated using:

```
def RMR_calc(Weight, Age, PA_fraction, THERM_fraction ):
  if SEX == 0:
```

```
    RMR = (248 * (Weight ** 0.4356)) - (5.09 * Age)
  else:
    RMR = (293 * (Weight ** 0.4330)) - (5.92 * AGE)
  TDEE = (1 + THERM_fraction + PA_fraction)*RMR #kcal/day baseline energy
  requirements per day
  return(RMR, TDEE)
``` where PA_fraction represents an additional fraction of the RMR burnt through physical activity and THERM_fraction is an additional fraction of RMR burnt through further elevation of thermogenesis (e.g. keeping warm on cold day or stimulated by GLP-1). The above equations for RMR are illustrative and other known approaches for determining RMR may be used.

FIGS. 18A to 18D illustrate the predicted weight loss profiles for a male, white patient, with a BMI of 40, weight of 130 kg, and 60 years of age using an example PKPD model corresponding to the second dosage calculator. For simplicity, the variation effects of injection site, race/ethnicity and kidney function were not included in the modelling. The FIGS. 18A to 18D show predicted weight loss profiles for respective maximum drug dosages of 1.0 mg, 2.5 mg, 3.5 mg and 4.5 mg of semaglutide administered subcutaneously. Each plot shows the predicted weight loss profile 1839 and the population-average profile 1838 from the STEP study data (same as profile of FIG. 14). The data illustrates that for a heavier patient (130 kg), a higher maximum dosage of 3.5 mg is required to achieve the same weight loss as the average participant of the step study (106 kg). The higher dosage may increase the probability of side effects.

Similarly FIGS. 18E to 18H illustrate the predicted weight loss profiles of a 166 cm, 44-yr female weighing 140 kg at baseline (mean/mode values from the 15 mg treatment arm of SURMOUNT-1, except for baseline weight, which was 105.6 kg in SURMOUNT-1) using an example PK-PD model corresponding to the second dosage calculator. FIGS. 18E, 18F, 18G and 18H show predicted weight loss profiles for maximum doses of 5 mg, 10 mg, 15 mg, and 20 mg, respectively. Each plot shows the predicted weight loss profile and the population-average profile from the 15 mg treatment arm of SURMOUNT-1. The data illustrates that for a heavier patient (140 kg), a higher maximum dosage of 20 mg is required to achieve the same weight loss as the average participant of the 15 mg treatment arm of SURMOUNT-1 (105.6 kg). As similar plot (not illustrated) to FIG. 15A was also generated for the tirzepatide model to confirm that the predicted weight loss profile matched the measured weight loss profile for the average participant of the SURMOUNT-1 study.

Dosage Calculator Example 3

A third example dosage calculator may comprise a look-up table derived from the first or second dosage calculator examples. As a result, the third step 1228, 1728 of FIGS. 12, 17 can advantageously be performed rapidly using a look-up table approach. In some examples, the look-up tables may be defined to output the initial dosage for administering to the patient based on received inputs of the patient data and the target end point (target plasma level, target weight loss or target glycemic control), negating the requirement for the process of FIG. 12 or 17 and resulting in more rapid dosage calculations.

Dosage Calculator Example 4

In some examples, the dosage calculator may comprise a machine learning (ML) model (also referred to as a ML algorithm) trained using data output from the PK or PKPD model. The data output from the PK model may comprise simulated population data. The simulated population data may comprise data output from the PK model following processing of a population set of patient data that represents a population variation in the patient data. For example, a Monte Carlo type approach may be used to generate the population set of patient data using known distributions of each parameter type of the patient data (see below). In some examples, the simulated population data may comprise predicted plasma levels output by the PK model. In some examples, the simulated population data may comprise predicted weight loss output by the PKPD model of the second example dosage calculator. In some examples, the simulated population data may comprise initial dosages for administering to each patient of the population set to achieve a target plasma level, a target weight loss, a target glycemic control or other target end point (e.g. target side effect level). The ML model can be trained using the simulated population data to provide a ML dosage calculator.

The ML dosage calculator may comprise any known ML architecture such as an artificial neural network or a generative model. In some examples, real patient data, e.g. from a clinical study or an ongoing dosage and monitoring program, may be added to the simulated population data to form the ML training data. The real patient data may comprise patient dosage, patient input data and measured drug plasma levels, measured diabetes metrics/glycemic control or measured weight loss. The ML training data may comprise weightings for each patient data set, with a higher weighting assigned to real patient data than to simulated patient data.

In some examples, the ML dosage calculator may replicate the PK or PKPD model and predict plasma levels, glycemic control weight loss for a particular dose and then revise the dosage estimate to obtain an initial dosage for administering to a patient (in the same way as FIG. 12 or FIG. 17).

Figure 19A:
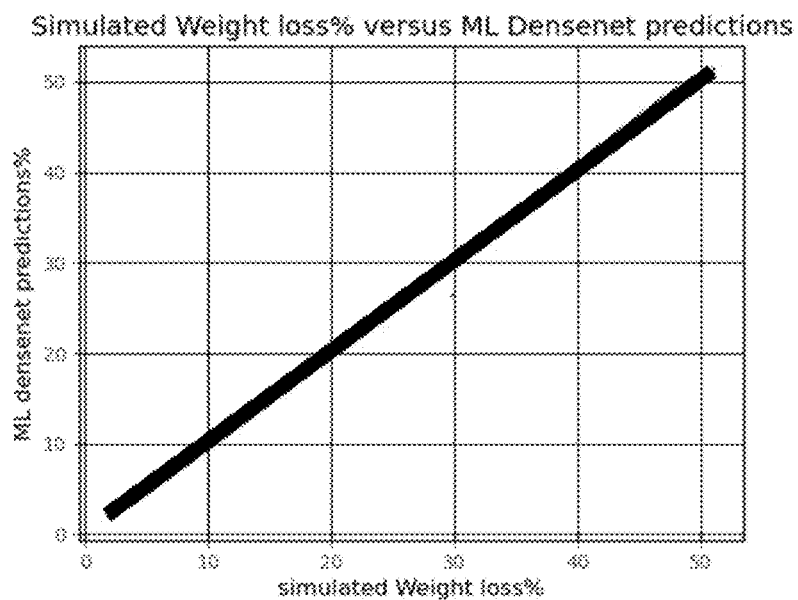
FIG. 19A illustrates the relationship between predicted weight loss for semaglutide administration using a PKPD model and a predicted weight loss using a ML dosage calculator according to an embodiment of the present disclosure.

In some examples, the ML dosage calculator may receive patient data and a target endpoint (target plasma level, target weight loss, target glycemic control or target side effect level), and directly determine a dosage for administering to the patient. As an example, the simplified semaglutide PKPD model described above in relation to the second example dosage calculator was used to create simulated population data comprising 100800 simulated obese patients. Such simulated population data could simply be used as a look-up table (e.g. the third example dosage calculator). An excerpt of the simulated population data is shown in table 2 below. The simulated population data was used to train a ML dosage calculator to output (maintenance/maximum) dose as a function of target weight loss and patient data (weight, age, sex, TDEE_ratio) without requiring the iterative approach of FIG. 17. A tensorflow densenet defined in python using the open source keras library comprising 1024 densely connected layers and a single output was trained over 100 epochs on the training data (simulated population data) with 20% of the training data reserved for validation. FIG. 19A illustrates the relationship between predicted weight loss using the PKPD model and the predicted weight loss using the ML dosage calculator. A perfect correlation is shown demonstrating that the ML dosage calculator can be used to rapidly replicate the second dosage calculator and provide a dosage as a function of target weight loss and patient data.

Figure 19B:
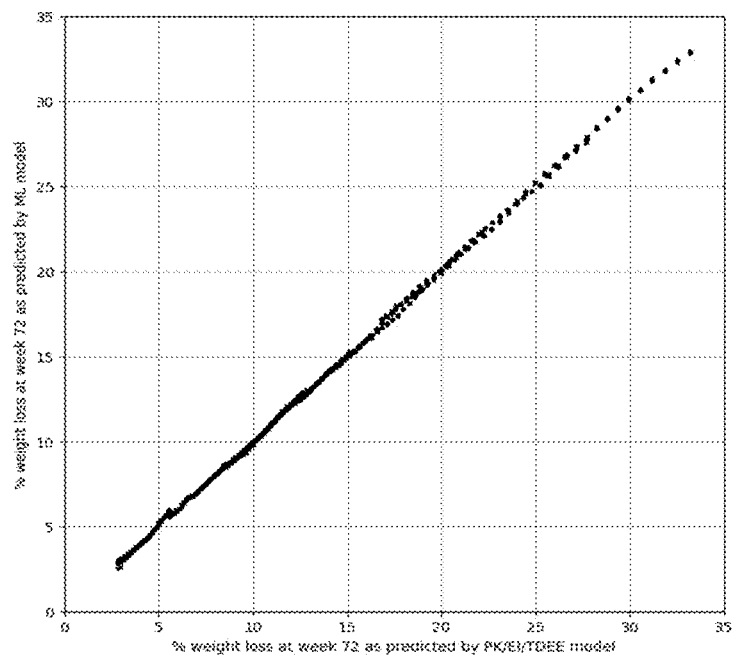
FIG. 19B illustrates the relationship between predicted weight loss for tirzepatide administration using a PKPD model and a predicted weight loss using a ML dosage calculator according to an embodiment of the present disclosure.

FIG. 19B illustrates a similar relationship for a second ML dosage calculator trained using simulated population data from the tirzepatide PKPD model described above. The figure illustrates the relationship between the predicted percentage weight loss at week 72 using the PK/EI/TDEE tirzepatide model and the predicted percentage weight loss at week 72 using a ML regression model. The ML regression model was trained and tested on a dataset with sex, baseline weight, height, age, maintenance dose, and TDEE_ratio as predictor variables and percentage weight loss at week 72 as predicted by the PK/EI/TDEE tirzepatide model as the label. The entire dataset contained 10,000 data points, and was split in a 70:30 ratio for training and testing.

Figure 19C:
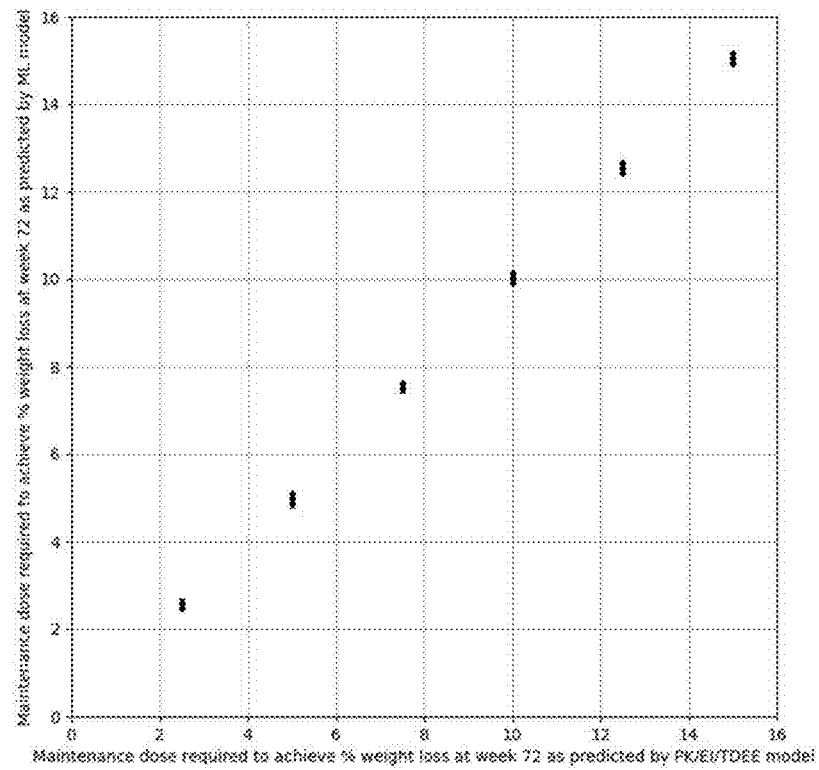
FIG. 19C illustrates the relationship between the maintenance dose that is required to achieve a given percentage weight loss at week 72, as predicted by the PK/EI/TDEE tirzepatide model, and the maintenance dose that is required to achieve a given percentage weight loss at week 72, as predicted by a third ML dosage calculator (regression model)

FIG. 19C illustrates the relationship between the maintenance dose that is required to achieve a given percentage weight loss at week 72, as predicted by the PK/EI/TDEE tirzepatide model, and the maintenance dose that is required to achieve a given percentage weight loss at week 72, as predicted by a third ML dosage calculator (regression model). This ML regression model was trained and tested on a dataset with sex, baseline weight, height, age, TDEE_ratio, and percentage weight loss at week 72 (as predicted by the PK/EI/TDEE model) as predictor variables and the maintenance dose that is required to achieve the given percentage weight loss at week 72 (as predicted by the PK/EI/TDEE model) as the label. The entire dataset contained 10,000 data points, and was split in a 70:30 ratio for training and testing.

Although this example utilises a maximum dose calculation, other example calculators may account for a stepped titration in dosage amount such as that outlined in table 1. The step profile may be defined as one of a number of variants, e.g. double dose every four weeks to maximum dosage, increment in 20% steps of maximum dosage every four weeks etc. These variants may be incorporated into the second (or first) example dosage calculator and may be provided as an additional column in the training data of table 2. The ML dosage calculator may then output a dosage regimen including a maximum dosage and a ramp or step profile as a function of target weight loss and patient data. The dosage calculator may select a particular step profile based on a side effect tolerance of the patient (see below).

A major advantage of the ML dosage calculator is that it can operate at significant speed relative to the first or second dosage calculators that directly and iteratively implement the PK compartment model. The efficient processing means the ML dosage calculator requires much less processing power than the model of equations 1 to 9 enabling deployment of the ML dosage calculator at scale to HCPs and/or patients, e.g. via a cloud platform and/or personal computing devices. Other advantages of the ML dosage calculator include: (i) a wealth of data available at speed including optimised dosages; and (ii) precise, personalised and accurate dosages. Furthermore, the model allows for continuous learning, including incorporation of new adjustment parameters as data accrues. Such adjustment may be performed in regulated phases or stages to ensure ongoing regulatory compliance and safety.

In some examples, a ML dosage calculator may be locked following training and validation, in that the ML dosage calculator will not "learn" from any future data. Such an approach can improve safety and enable easier regulatory approval by ensuring that the ML dosage calculator does not evolve into an unsafe regime based on an error in further training data. Alternatively, in some examples, such as applications where safety requirements may be more relaxed, for example where the drug is used in terminal illnesses, a highly monitored environment, or a clinical situation in which the HCP has no alternative, the ML dosage calculator may be free to evolve and use live data as further training data to provide a more accurate dosage calculator.

A further advantage of training a ML dosage calculator is that it can provide outputs for combinations of co-variants that are not well represented in original patient data set. In this way, the ML dosage calculator can artificially enrich specific cases of interest and improve the weighting and consideration of less common combinations of characteristics thereby reducing bias and inferior predictions.

Furthermore, deploying the safe, predictable, efficient ML dosage algorithm at scale for patients and HCPs can enable the collection of real patient data (including measured PK metrics, e.g. updated weight data, HbA1c, blood glucose level). Such deployment would be infeasible with a two-compartment differential equation based PK model due to the processing constraints. The collected real patient data can then be used to evolve the ML dosage calculator and/or the PK model to further improve the accuracy and precision of the dosage calculator.

Although the above description describes the calculation or determination of a target plasma level based on the weight

TABLE 2

| Simulated population data | | | | | | | | |
|---|---|---|---|---|---|---|---|---|
| pid | GLP_1 | BMI | Height | Weight_0 | AGE | SEX | TDEE_ratio | Weight_final | WT_loss_PC |
| 6754 | 0.5 | 30 | 166 | 83.0 | 58 | 0 | 1.6 | 79.539698 | 4.0 |
| 11536 | 0.5 | 34 | 174 | 103.0 | 64 | 0 | 1.7 | 100.205176 | 3.0 |
| 21583 | 1.0 | 28 | 168 | 79.0 | 56 | 0 | 1.2 | 71.260568 | 10.0 |
| 51340 | 2.0 | 24 | 172 | 71.0 | 78 | 0 | 1.2 | 53.558485 | 25.0 |
| 42433 | 1.5 | 32 | 166 | 88.0 | 52 | 0 | 1.6 | 78.181011 | 11.0 |

Although dosage calculators based on a semaglutide ML model and a tirzepatide ML model have been described, a similar ML based dosage calculator for Cagrisema or another incretin pathway drug could be developed following the same method described and starting from an appropriate PK model (such as that described in [8] for Cagrisema).

loss data, diabetes metric data or an ideal therapeutic level, in some examples the method may comprise determining the target plasma level based on a patient side effect tolerance either in addition to, or alternatively to, determining the target plasma level as an ITL or based on patient data (weight data or diabetes metric data). In this way, predicted side effects can be used as the target end point of the PK plasma level model.

Figure 13:
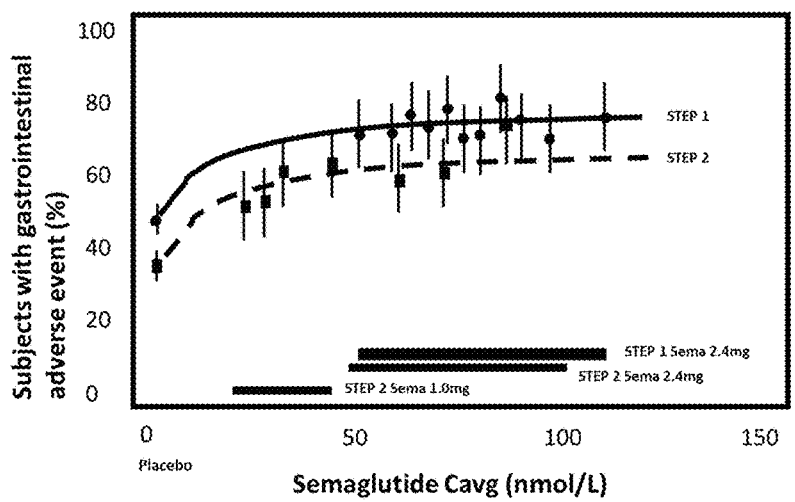
FIG. 13 illustrates the dependency of side effect probability on drug dosage.
Figure 13:
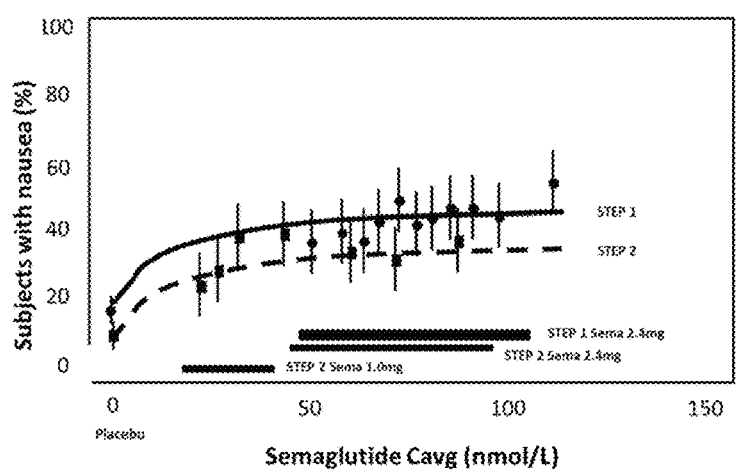
Figure 13:
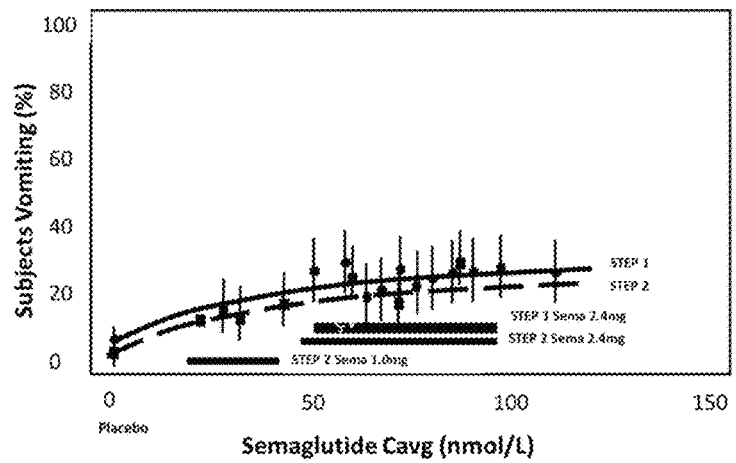

FIG. 13 illustrates the relationship between adverse side effects and semaglutide plasma level as reported by [1]. A first plot, A, illustrates the variation of all adverse effects with plasma level. A second plot, B, illustrates the variation for nausea specifically and a third plot, C, illustrates the variation for vomiting. The most troublesome side effect is nausea which exhibits a dose response relationship with more nausea at higher doses. The plots illustrate that side effects reduce at plasma levels less than 50 nmol/L.

Therefore, the method may comprise setting a target plasma level based on the side effect tolerance of the patient. The side effect tolerance may comprise a personal indication by the patient of their willingness to tolerate adverse side effects associated with semaglutide. The side effect tolerance may also comprise patient history data such as a history of gastrointestinal problems (the main adverse effect of semaglutide). The side effect tolerance may be a linear scale, for example a score from 1 to 10. The side effect tolerance may include a general side effect tolerance or one or more specific side effect tolerances such as a nausea tolerance, a vomiting tolerance etc.

In some examples, the method may set the target plasma level based on a predetermined mapping between side effect probability and drug plasma level. For example, for obesity, based on the plots of FIGS. 2A and 13 for semaglutide, the method may set the target plasma level to less than or equal to 50 nmol/L, for example to a target plasma level from 25 nmol/L to 50 nmol/L, if the side effect data tolerance represents a patient sensitivity to side effects. For diabetes, based on the plots of FIGS. 2B and 13 for semaglutide, the method may set the target plasma level to be less than or equal to 40 nmol/L for examples from 15 to 40 nmol/L. In other examples, the method may set a nominal target plasma level based on the patient data as described above and then adjust the nominal target plasma level based on the side effect tolerance (e.g. reduce target plasma level by 10% or 25%). If the side effect tolerance is high, the method may increase the nominal target plasma level and vice versa.

The predetermined mapping between side effect probability and drug plasma level may comprise a sigmoidal Emax model or other side effect model that models drug effect as a function of plasma level and/or dose. The sigmoidal Emax or other side effect model may comprise a personalised sigmoidal Emax model (e.g. based on the patient data parameters (e.g. age, ethnicity, diabetes history, sex etc.)). The side effect model may predict a number of side effect metrics including: the proportion of the overall treatment period spent experiencing side effects, the probability of experiencing at least one side effect, and the number of side effects experienced. The side effect model may predict the side effect metrics for a specific patient following a specific dosing regimen.

For example, a side effect model may comprise a discrete-time Markov model, such as the model for predicting nausea, vomiting, and diarrhoea from the Center for Drug Evaluation and Research's Clinical Pharmacology Review for Mounjaro [5]. In some examples, a side effect model may comprise an Emax exposure-GI side effect model such as that described in [1].

Figure 20A:
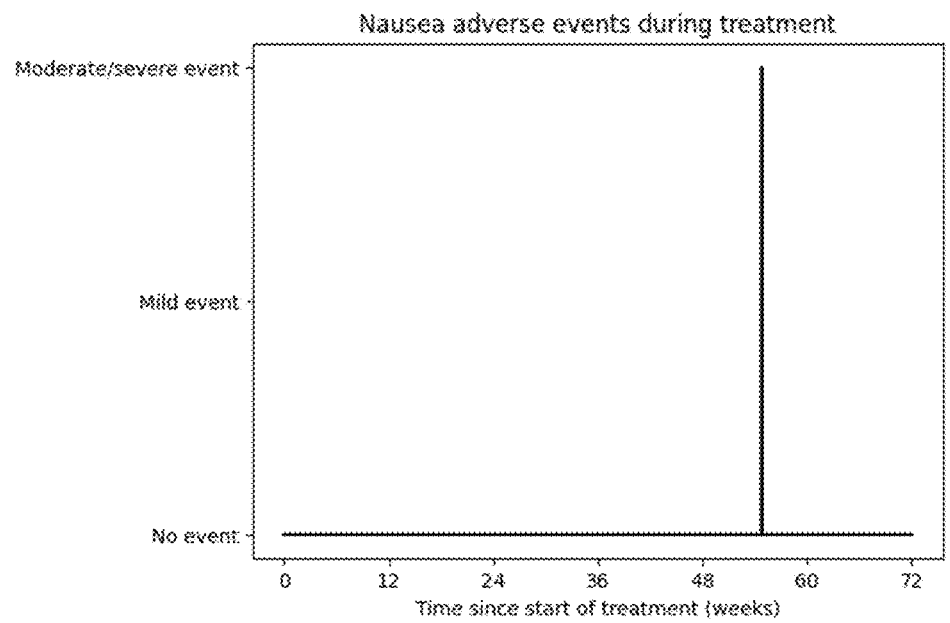
FIGS. 20A to 20C illustrate results from a discrete-time Markov side-effect model for predicting nausea, vomiting and diarrhoea according to an embodiment of the present disclosure.
Figure 20B:
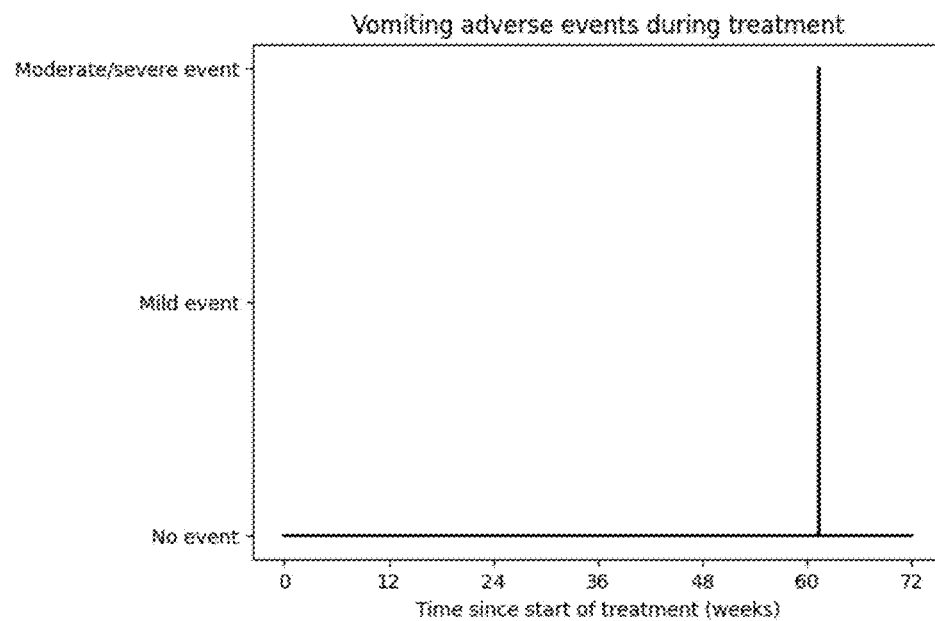
Figure 20C:
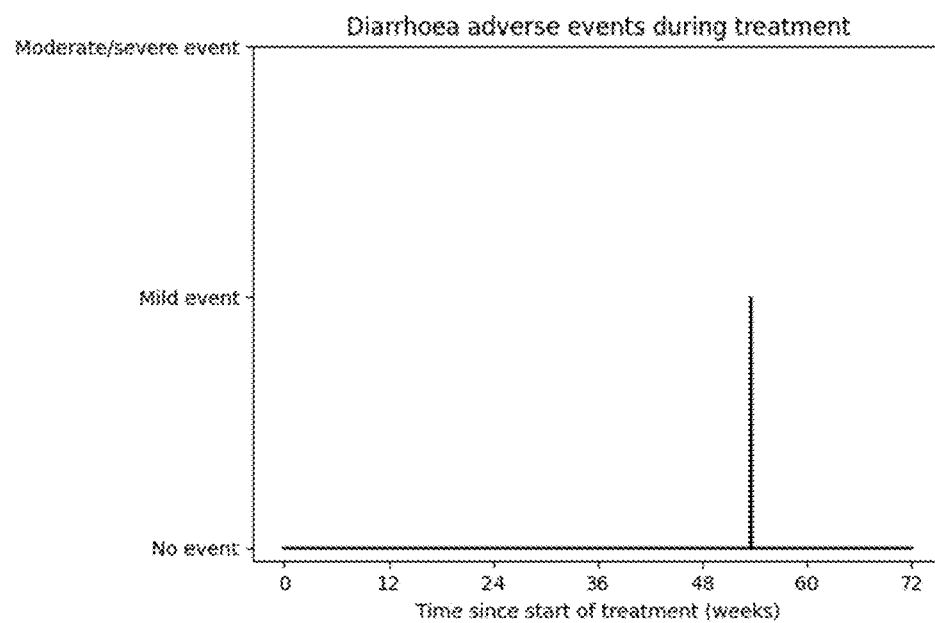

FIGS. 20A-20C illustrate the results from a discrete-time Markov side-effect model for predicting nausea, vomiting and diarrhoea. The model was developed based on the model from [5]. The model is based on data on plasma tirzepatide concentration and adverse events. Adverse events are separated into three categories/states, each denoted by a number: no event (0), mild event (1), and moderate/severe event (2). Transition probabilities specify the probability of remaining in the current state or moving from one state to another—e.g. from no event to a mild event—at any given time. The side-effect model was incorporated into the PK model using an additional tolerance compartment, with a rate of accumulation from the central compartment and decay of drug in this tolerance compartment determined by a first-order rate constant, $K_{TOL}$. This rate constant was found to depend on a number of patient data parameters including Hispanic ethnicity, Japanese subrace and gender. At each timepoint, an individual is modelled as being in three states (one for nausea, one for vomiting, and one for diarrhoea). Values of $K_{TOL}$ and transition probabilities are modified according to the concentration of the drug in the peripheral and tolerance compartments, $C_P$, $C_T$, the presence/absence of the prior occurrence of a first adverse event, the presence/absence of nausea currently, the study GPGL effect (if applicable), and various covariate effects. The model then stochastically predicts the next state according to the modified transition probabilities associated with remaining in or transitioning from the current state. This process continues until a complete sequence of states has been generated, thus simulating a patient's journey through drug treatment.

FIGS. 20A, 20B, and 20C show the simulated occurrences of nausea, vomiting, and diarrhoea adverse events for a non-Japanese, female participant with a BMI of 38.0 $kg/m^2$ and a body weight of 104.8 kg at baseline (average values from SURMOUNT-1) taking tirzepatide for 72 weeks, as predicted by the discrete-time Markov model.

FIGS. 20A, 20B, and 20C were created by running the model to predict the incidence of nausea, vomiting, and diarrhoea one time. Each time the model is run, the model is likely to return a different result in terms of the presence/absence of each adverse event, the severity of each adverse event occasion, the number of adverse event occasions, the duration of each adverse event occasion, and the timing of each adverse event occasion. To gain utility from the model, in some examples, the model may be run many times for a patient with specific characteristics, and summary metrics calculated, such as the mean number of adverse event occasions, the mean duration of each adverse event occasion, the mean time spent experiencing each adverse event, the mean time spent experiencing an adverse event of a given severity, the mean proportion of the entire treatment period spent experiencing each adverse event, and the mean proportion of the entire treatment period spent experiencing an adverse event of a given severity. These summary metrics can be calculated across the entire treatment period or within shorter time periods into which the entire treatment period is segmented.

In some examples, instead of running the model many times for each patient on demand, the model may initially be run many times for a virtual patient population to output the summary metrics for each virtual patient. The virtual patient population may comprise patients with data spanning a range of each relevant characteristic, such as ethnicity, sex, body weight, and BMI. A side effect ML model may be trained on the dataset containing the virtual patient characteristics and the summary metrics to predict the summary metrics. The ML model may then be used to predict a summary metric—for example, the time spent experiencing an adverse event of a given severity—for a new patient with specific characteristics. Implementing a ML approach can save computational time at the point at which summary metrics for a patient with specific characteristics are required.

Similarly, the dataset containing the virtual patient characteristics and the summary metrics could be used to build a look-up table with values of summary metrics given for many patients with data spanning a range of each relevant characteristic. Again, this approach can save computational time at the point at which summary metrics for a patient with specific characteristics are required.

The summary metrics could be used to inform treatment decisions for an individual patient. Although the side effect model described is specific to tirzepatide, similar models may be provided for other weight loss or T2DM drugs, such as semaglutide or Cagrisema.

Therefore, in some examples, the dosage calculator may comprise a side-effect model. The dosage calculator may receive a patient side-effect tolerance or side-effect target. The dosage calculator may process the patient side-effect tolerance and patient data to determine a dosage for administration. The dosage calculator may: (i) process the patient side effect tolerance and patient data to determine a target drug concentration that will satisfy the patient side effect tolerance; and (ii) process the target drug concentration and the patient data to determine the initial dosage. The side effect model may comprise a discrete-time Markov model or an Emax exposure side effect model. The side effect model may comprise a machine learning model trained using simulated population data generated using a discrete-time Markov model or an Emax exposure side effect model. The simulated population data may be generated by processing simulated patient data with the discrete-time Markov model or the Emax exposure side effect model.

In some examples, the method may apply the side effect tolerance at the end of the process of determining the initial dosage. For example, the method may comprise determining a nominal initial dosage based on the patient data and then adjusting the nominal initial dosage based on the side effect tolerance. If the side effect tolerance is high, the method may increase the nominal initial dosage and vice versa. As described herein, increasing/decreasing the initial dosage may comprise increasing/decreasing one or more dosage amounts (e.g. reduce dosage by 10% or 25%) and/or increasing/decreasing the ramp rate of the dosage increases during the initial titration phase as the drug amount is increased to the maximum dose (e.g. reduce increment steps from weekly to two-weekly).

By including the side effect tolerance in the dosage calculation, the disclosed methods can determine a dosage regimen based on both target weight loss/glycemic control and side effect profile.

Although GI side effects have been used as the example above, the side effect model and side effect tolerance/target may relate to any side effect of the incretin pathway drug. For example, the side effect may comprise a general side-effect including one or more of: appetite decreased (in patients with type 2 diabetes); burping; cholelithiasis; constipation; diarrhoea; fatigue; gastrointestinal discomfort; gastrointestinal disorders; hypoglycaemia (in combination with other antidiabetic drugs, in patients with type 2 diabetes); nausea; vomiting; weight decreased (in patients with type 2 diabetes); pancreatitis acute; and taste altered. The side effect may include a specific side effect including: (for subcutaneous use) alopecia; diabetic retinopathy (in patients with type 2 diabetes); dizziness; headache; angioedema.

Additional side effects may become apparent through further trials and real world usage of incretin pathway drugs. The presently disclosed systems and methods can advantageously account for such additional side effects by developing a specific side effect model based on appropriate patient data.

Although PK studies do not show a significant dependence of semaglutide plasma concentration on other co-medications, the presence or effect of semaglutide may affect the efficacy other such co-medications. For example, semaglutide can slow gastric emptying which may affect the absorption of other drugs. Furthermore, if the dosage of semaglutide is ramped too high or too quickly, diabetic patients taking insulin may be vulnerable to hypoglycaemia. Similar considerations apply to tirzepatide, Cagrisema and incretin pathway drugs more generally. Therefore, the method may comprise adjusting (reducing) a nominal target plasma level or a nominal initial dosage based on the patient medication list.

In some examples, the method may address additional individual complexities. For example, some patients with obesity may have already had gastric bypass surgery. Such surgery leads to elevated GLP-1 levels. The method may comprise adjusting (decreasing) a nominal target plasma level or a nominal initial dosage based on a patient bariatric surgery history. As described below, the method may comprise calibrating the dosage calculator or underlying PK model based on patient data. The adjustment required for post-bariatric surgery patients may be determined based on future patient data.

Although, the intermediate step of setting or determining a target plasma level has been described above for understanding and in relation to the first and second example dosage calculators, such a step is optional and many dosage calculators can process the patient data and a target endpoint (e.g., a target weight loss, target glycemic control and/or a target side effect level) and directly determine the initial dosage. This is particularly the case for look-up table or machine learning based dosage calculators (third and fourth example dosage calculators) in which the relationships between the initial dosage, the patient data parameter space (weight, age, ethnicity etc) and the target endpoint (weight loss, glycemic control and/or side effects) have been mapped out and predetermined using the PK model.

Calculating Dosage amount and/or Dosage Frequency

As noted above, the dosage calculators may process the patient data and the target endpoint to determine the initial dosage. This initial dosage may comprise a dosage amount and a dosage frequency (or dosage interval). In some examples, the dosage calculator may determine: (i) a personalised dosage amount for a fixed dosage frequency; (ii) a personalised dosage frequency for a fixed dosage amount; or (iii) a personalised dosage amount and a personalised dosage frequency, that achieves the target endpoint. In (ii) a fixed dosage amount may comprise a ramp profile of a plurality of fixed dosage amounts.

Figure 4H:
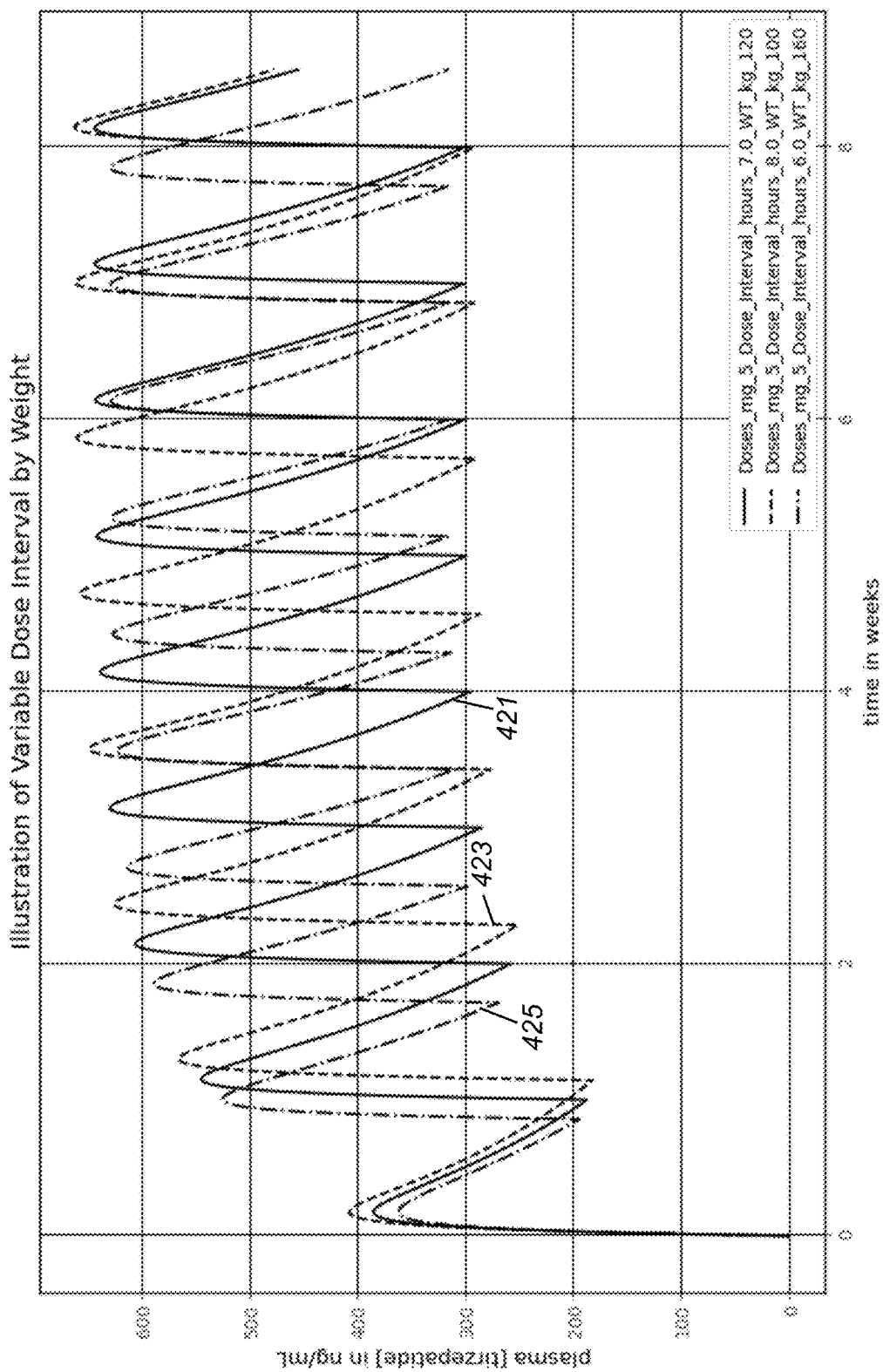
FIG. 4H illustrates personalised dosing intervals for three different patients with differing patient weight each taking a fixed dosage amount of 5 mg of subcutaneous tirzepatide.

FIG. 4H illustrates personalised dosing intervals for three different patients with differing patient weight each taking a fixed dosage amount of 5 mg of subcutaneous tirzepatide, that achieve the same target trough plasma level, as determined by the first example dosage calculator.

A first plot 421 illustrates the evolution of the plasma concentration over 8 weeks for a first patient with a patient weight of 120 kg administered 5 mg subcutaneous tirzepatide with a dosing frequency of 7 days. A second plot 423 illustrates the evolution of the plasma concentration over 8 weeks for a second patient with a patient weight of 100 kg administered 5 mg subcutaneous tirzepatide with a dosing frequency of 8 days. A third plot 425 illustrates the evolution of the plasma concentration over 8 weeks for a third patient with a patient weight of 160 kg administered 5 mg subcutaneous tirzepatide with a dosing frequency of 6 days. All three plots evolve to a steady state plasma profile with a trough plasma level of ~300 ng/mL and similar Cmax values between 620-650 ng/mL.

Figure 4I:
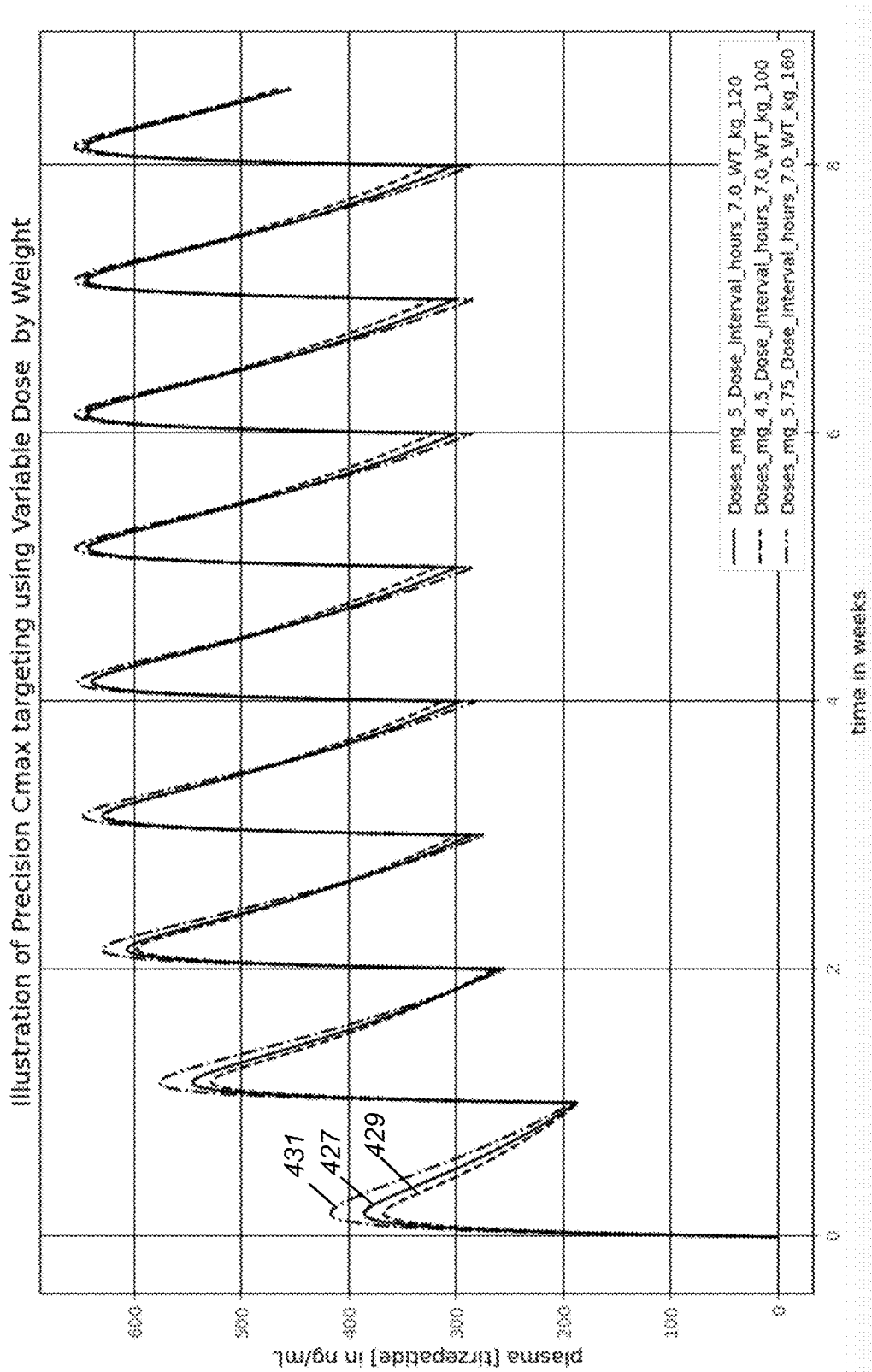
FIG. 4I illustrates personalised dosing amounts of subcutaneous tirzepatide for three different patients with differing patient weight for a fixed dosing interval of 7 days.

FIG. 4I illustrates personalised dosing amounts of subcutaneous tirzepatide for three different patients with differing patient weight for a fixed dosing interval of 7 days, that achieve the same target trough plasma level, as determined by the first example dosage calculator.

A first plot 427 illustrates the evolution of the plasma concentration over 8 weeks for a first patient with a patient weight of 120 kg administered 5 mg subcutaneous tirzepatide with a dosing frequency of 7 days. A second plot 429 illustrates the evolution of the plasma concentration over 8 weeks for a second patient with a patient weight of 100 kg administered 4.5 mg subcutaneous tirzepatide with a dosing frequency of 7 days. A third plot 431 illustrates the evolution of the plasma concentration over 8 weeks for a third patient with a patient weight of 160 kg administered 5.75 mg subcutaneous tirzepatide with a dosing frequency of 7 days. All three plots evolve to a steady state plasma profile with a trough plasma level of ~300 ng/mL and similar Cmax values between 620-650 ng/mL.

Mapping Expectation Trajectories

Once the initial dosage is set, the method may determine one or more expectation trajectories. The one or more expectation trajectories may include: a dosage trajectory; a weight loss trajectory; an expected calorie intake trajectory (for obesity patients); an expected glycemic control (e.g. HbA1c or CGM) trajectory; and a side effect trajectory. An expectation trajectory may comprise an expectation range comprising an upper expectation trajectory and a lower expectation trajectory.

The dosage trajectory may comprise the initial dosage regimen (i.e. the stepped increase to the maximum dose). Following the increase to the maximum/maintenance dose, the dosage trajectory may also include a stepped reduction in dosage amount corresponding to their predicted weight loss to maintain a stable plasma level. As the patient approaches an equilibrium or target weight or a target glycemic control, the dose trajectory may include a further stepped decrease for a planned drug withdrawal.

For incretin pathway drug/semaglutide dosing for obesity, the method may comprise estimating an equilibrium weight based on the initial dosage. The equilibrium weight may be the same as the target weight (e.g. due to the relationship of FIG. 2A) if there was no adjustment to the initial dosage arising from the side effect tolerance or the patient medication list. Alternatively, the equilibrium weight may be higher than the target weight if the nominal target plasma level or nominal initial dosage was reduced due to the side effect tolerance or the patient medication list.

The method may comprise determining the equilibrium weight by modelling a percentage weight loss, $WT_\%$, as a sigmoidal function as follows:

$$WT_\% = \left(E_{MAX}(WT) * \left(\frac{C_{c,ss}}{EC_{50}(WT) + C_{c,ss}}\right)\right) + E_0(WT) \quad \text{(Eq 18)}$$

where $E_0(WT)$ is expected weight loss in absence of drug (placebo effect), $E_{max}(WT)$ is maximal percent contribution, $EC_{50}(WT)$ is average plasma concentration for half maximal effect, $C_{c,ss}$ is the mean plasma drug concentration at steady state over the time between successive doses. The values of the parameters can be derived from direct modelling of observed clinical data from patient studies. In some examples, the model may be further refined to account for individual patient data characteristics (e.g. age, sex, ethnicity etc).

Patient studies have shown a typical weight loss trend over a period of ~70 weeks for patients taking semaglutide, as illustrated and described above in relation to FIG. 14. In some examples, the method may comprise defining the weight loss trajectory according to this typical exponential decay profile from the initial weight to the estimated equilibrium weight. In some examples, the method may comprise defining the expected weight loss trajectory using the second example dosage calculator described above. The weight loss trajectory may define a plurality of weight loss milestones at periodic time points from the onset of therapy and during a treatment period of the prescribed semaglutide.

The expected weight loss trajectory can be converted to an expected calorie intake trajectory, that will achieve the expected weight loss, using a EI/TDEE model, such as the one described above in relation to the second example dosage calculator. The expected calorie intake trajectory may comprise the predicted energy intake deficit profile of FIG. 15A or 15B.

As noted earlier and explained in detail below, the present disclosure includes the provision of a digital therapeutic program that can indicate a behavioural therapy for administering in conjunction with the incretin pathway drug. The method may use the weight loss trajectory and/or the expected calorie intake trajectory to determine a calorie intake regimen of the behavioural therapy.

For incretin pathway drug/semaglutide dosing for diabetes, the method may also provide a predicted weight loss trajectory (for example based on a (personalised) sigmoidal Emax model, the second example dosage calculator or the relationship of FIG. 2A) whether overweight or not. For the latter group, it may still be desirable to decrease weight, whilst remaining in the normal range (e.g. a decrease in BMI from 24 to 19), and for those that have reached their lowest desired weight, to adjust behaviours (or drug dosage) such that there is no further weight loss.

The expected glycemic control trajectory may include an expected reduction in HbA1c levels and/or average blood glucose. The method may calculate the expected glycemic control based on a predetermined relationship between plasma level and glycemic control (such as a (personalised) sigmoidal Emax model or the data of FIG. 2B). Providing an expected blood glucose trajectory can be advantageous because HbA1c is slow varying. The method may provide an expected trajectory of both HbA1c and average blood glucose, as both parameters are important. Patients can compare CGM data comprising a time-averaged blood glucose level against the expected trajectory.

The side effect trajectory may map closely to the dosage trajectory (with a time lag to account for accumulation) because the probability of side effects is dependent on plasma level (see FIG. 13). Some side effects, such as nausea, ease with increased duration at a particular dose and the side effect trajectory may predict such easing.

The method may comprise determining the side effect trajectory by modelling a percentage chance of experiencing a GI related adverse event, $GI_\%$, as a sigmoidal function as follows:

$$GI_\% = \left(E_{MAX}(GI) * \left(\frac{C_{c,ss}}{EC_{50}(GI) + C_{c,ss}}\right)\right) + E_0(GI) \qquad \text{(Eq 19)}$$

where $E_0(GI)$ is percentage probability of GI effect in absence of drug (placebo effect), $E_{max}(GI)$ is maximal percent contribution, $EC_{50}(GI)$ is average plasma concentration for half maximal effect and $C_{c,ss}$ is the mean plasma drug concentration at steady state over the time between successive doses. The values of the parameters can be derived from direct modelling of observed clinical data from patient studies. Any of the side effect models described above may also be used to generate the side effect trajectory.

The method may comprise outputting the one or more expectation trajectories and/or the calorie intake regimen to the patient or clinician. Such information can be useful for the patient and/or clinician to track the patient's progress, understand the requirements for calorie restriction and probability of adverse side effects. The one or more expectation trajectories and/or the calorie intake regimen may be output via a digital app on an electronic device.

Once treatment begins, the method may comprise receiving updated patient data, updating the incretin pathway drug/semaglutide dosage based on the updated patient data and indicating the updated dosage (e.g. via the digital app). The method may also comprise updating the one or more expectation trajectories based on the updated patient data and/or the updated dosage, and outputting the one or more updated expectation trajectories (e.g. via the digital app).

Updating the Drug Dosage During Treatment

Following commencement of therapy, the patient data will start to change both as a result of the therapy and from external factors. The method may comprise receiving updated patient data, updating the incretin pathway drug/semaglutide dosage based on the updated patient data and indicating the updated dosage (e.g. via the digital app).

The method may comprise updating the drug dosage intermittently or periodically (although the updated patient data may be received more frequently or even continuously). The method may comprise updating the drug dosage only after an elapsed time corresponding to a drug effect time (e.g. 20 days) for the blood plasma level to reach substantially steady state after the most recent drug dose. For obesity, the method may comprise updating the drug dosage at times corresponding to the weight loss milestones of the weight loss trajectory. These may provide suitable times to review whether the current dosage is optimal and having the desired effect. In some examples, the method may comprise updating the drug dosage "on demand" in response to particular updated patient data. For example, if the updated patient data indicates severe adverse side effects, the method may comprise reducing the drug dosage immediately.

The dosage updates may be divided into two categories: (i) Updates to the nominal dosage regimen designed to maintain a fixed target plasma level (e.g. as the patient weight reduces the dosage should be decreased to maintain the same plasma concentration (see FIG. 4B)); and (ii) Adjustments to the nominal dosage regimen based on patient progress with the treatment (e.g. if the patient experiences intolerable side effects or the weight loss is behind the expected weight loss trajectory). These two categories are discussed in turn.

Updating Nominal Dosage Regimen

As the patient loses weight, circulating plasma levels will increase at a constant dose. Given that the desired effect of the drug is to decrease weight, this means that with increasing duration of action of drug, an increase in plasma concentration will result if dose is maintained. Therefore, to achieve a constant concentration, the dosage requires downward titration. Similarly, any variation in secondary patient data parameters such as age, kidney function, diabetes history, injection site, may affect the drug plasma level.

The method may comprise processing the updated patient data with the dosage calculator to determine an updated nominal dosage regimen for maintaining the target plasma level and/or the target end point (target weight loss and/or target side effect level) at a previously set level (e.g. the initial value set during determination of the initial dosage regimen). The dosage calculator may determine the updated nominal dosage regimen based on the updated patient data in the same way as described above for determining the initial dosage regimen. The method may comprise indicating an updated dosage regimen based on the updated nominal dosage regimen (e.g. following adjustments for other parameters such as side effects, or patient progress data as discussed below). The method may comprise indicating an updated dosage regimen based on the updated nominal dosage regimen only if the updated dosage regimen differs from a previous dosage regimen by a threshold amount. This can advantageously avoid frequent minimal changes in dosage regimen. In some examples, the method may comprise processing the updated patient data to determine an updated predicted plasma level. The method may comprise processing the patient data to determine and an updated nominal dosage and indicate an updated dosage, if the updated predicted plasma level differs from the previously set level by a threshold amount.

As a specific example, the method may comprise receiving an updated patient weight indicating a 5% weight loss. The method may comprise processing the 5% weight loss with the dosage calculator to determine a nominal updated dosage that maintains the same target plasma level that was calculated for the initial dosage. The nominal updated dosage may comprise a corresponding reduction of the initial dosage. The reduction may comprise a reduction to a lower dosage amount for future doses and/or a change in timings between doses (dose frequency) and/or dose changes. As the reduction in dosage is greater than a threshold amount, the method continues to indicate the updated dosage to the patient.

Updating Dosage Regimen Based on Patient Progress

Following initiation of the semaglutide dosage regimen (or incretin pathway drug dosage more generally), the method may comprise receiving and monitoring updated patient data in the form of patient progress data. The patient progress data may include one or more variables indicating the progress of their response to the drug, weight loss, dietary restriction (obesity) and glycemic control (diabetes). The patient progress data may include one or more of:

Patient side effect data. The method may comprise receiving reported side effect data via patient input. The method may comprise prompting the patient with a list of potential side effects. The acquired data may include all GI disturbances such as nausea and vomiting. Potential side effects may include one or more of: nausea, diarrhoea, vomiting, constipation, abdominal (stomach) pain, headache, fatigue, dyspepsia (indigestion), dizziness, abdominal distension, eructation (belching), hypoglycaemia (low blood sugar) in patients with type 2 diabetes, flatulence (gas build-up), gastroenteritis (an intestinal infection) and gastroesophageal reflux disease (a type of digestive disorder). The patient may input side effects experienced and a severity level. The severity level may comprise a qualitative (low, medium, high) and/or quantifiable score (e.g. pain, nausea etc. on a scale of 1-10) which may be received via patient entry using a visual analogue scale or slider on the electronic device. The timing of nausea in relation to meals, duration and effect on function is also recorded. Furthermore, the effect of a side effect such as nausea on function may be recorded. A patient may have relatively mild nausea that they find markedly interferes with function, whereas another patient may note nausea as being quite severe, but are able to continue with function.

Patient weight loss data, for example regular (e.g. daily) patient weight measurements. The method may comprise receiving the patient weight loss data via manual user input from the patient on the electronic device or as a signal from electronic scales communicatively coupled with the electronic device. The method may comprise calculating a moving average of patient weight due to the inherent fluctuation in weight, particularly when measured on scales owing to differences in food and fluid intakes and timing of bowel motions. The method may also incorporate a time lag before recommending a decision based on the patient weight data to avoid erroneous oscillation.

Patient calorie intake data. The patient may record their food intake. For example, the method may comprise providing a database of foodstuffs and food types that the patient can select on the electronic device to indicate consumption. The calorie intake data may comprise a moving average calorie intake, for example an average daily calorie intake data over a period of 3 days or 7 days.

Patient satiety/hunger score. The method may comprise receiving a quantifiable input from the user to indicate a degree of satiety they are experiencing. The method may comprise receiving the input via patient entry using a visual analogue scale or visual slider that the patient can manipulate on the patient electronic device. The method may comprise receiving the satiety score regularly, for example via daily prompts or more regularly, and/or on demand. The method may comprise monitoring the patient satiety as a moving average to determine whether the patient is consistently experiencing hunger suppression. The patient satiety score may also encompass a patient fullness score and/or a patient hunger score.

Patient activity data. The patient activity data may represent a level of physical activity undertaken by the patient and may include manual user entry or automated sensor entry using an activity sensor such as an accelerometer or motion sensor. Such sensors may be provided as part of the patient electronic device.

Patient motivation score. The method may comprise receiving a quantifiable input from the user to indicate their motivation to continue with the program and the calorie intake regimen. The method may comprise receiving the input via patient input using a visual analogue scale or visual slider that the patient can manipulate on the patient electronic device. The method may comprise receiving the motivation score regularly, for example via daily prompts, and/or on demand. For example, the patient may activate a low motivation alert button when they are experiencing intense cravings or low mood. Diabetes Metric Data. The method may comprise receiving updated diabetes metric data. The updated diabetes metric data may include updated HbA1c measurements from a physiological test. The updated HbA1c measurements may be provided periodically, e.g. monthly. The updated diabetes metric data may include continuous glucose monitoring (CGM) data. The CHM data may be received from a CGM device of the patient. The CGM data may be time-averaged CGM data e.g. over one or more days or weeks thereby smoothing out troughs and peaks. The CGM data may comprise other metrics such as trough levels, peak levels etc. Recent advances in continuous glucose monitoring (CGM), have reported a reduction in HbA1c levels of T2D patients using CGM. Drivers of the reduction may include an improved understanding of how diet, lifestyle and exercise impact diabetes via CGM readings.

The method may comprise adjusting the drug dosage based on the patient progress data. Adjusting the drug dosage may comprise increasing or decreasing a dosage amount of one or more scheduled dosages, adjusting one or more dosage timings of scheduled dosages (e.g. dose frequency), increasing or decreasing a ramp rate of a planned dosage increase or decrease etc. Updates to drug dosage for the treatment of diabetes (optionally in combination with obesity) may be subject to HCP approval in view of the added risks (e.g. hypoglycaemia).

Dose Adjustment in Response to Reported Side Effects

The titration regimen in the label for subcutaneous semaglutide for obesity allows for dosing flexibility, allowing a drop in dose from the highest approved dose of 2.4 mg back down to 1.7 mg if the patient would otherwise discontinue treatment completely due to adverse side effects. The label recommends at least one attempt to put the dose back up to 2.4 mg. The disclosed systems and methods may indicate a longer duration at each dose before increasing to the next step for patients indicating side effects that are limiting function. For example, titration to an intermediary dose such as from 1.7 to 2 mg and then 2.2 mg and then 2.4 mg is also envisaged. The disclosed systems and methods may accommodate additionally doses higher than 2.4 mg, were they to become licensed, or selected for off-label use by a clinician.

Therefore, the method may comprise reducing a dosage if the reported side effect data satisfies one or more side effect intolerance thresholds. Reducing the dosage may comprise a reduction in one or more dosage amounts and/or a delay or change in one or more dose timings. Reducing the dosage may comprise determining an adjusted dosage by reducing the nominal dosage determined using the PK derived dosage calculator. Reducing the dosage may comprise reducing the target plasma level and calculating a new nominal dosage with the dosage calculator that will provide the reduced target plasma level. For example, for semaglutide for obesity, the target plasma level may be reduced to be less than or equal to 50 nmol/L, for example to a target plasma level from 25 nmol/L to 50 nmol/L (FIGS. 2A and 13). For semaglutide for diabetes, the target plasma level may be reduced to be less than or equal to 40 nmol/L, for example to a target plasma level from 15 nmol/L to 40 nmol/L (FIGS. 2B and 13). The side effect intolerance threshold may comprise a timeframe, for example a level of nausea has been unacceptable for a number of consecutive days. The intolerance threshold may simply comprise the patient reporting that they cannot tolerate one or more side effects. Conversely, the patient may indicate a willingness to proceed despite reporting severe side effects. In such examples, the method may comprise maintaining the dosage if the reported side effect data indicates a patient willingness to proceed.

Patient studies indicate that reported nausea drops with increased duration of any particular dose when maintained at that level. This adaptation may result from changes in patient physiology, but may also result from behavioural adaptations that the patient may undertake, such as eating smaller meals with, if necessary, increased frequency. The method may include educating the patient on such tolerance build up and/or providing advice to reduce the effects of nausea, prior to indicating a dosage reduction.

Following a reduction in dosage in response to the reported side effect data not satisfying the side effect intolerance threshold, the method may continue to periodically monitor the reported side effects data. If the reported side effect data indicates a reduction in severity to a tolerable level or a patient willingness to proceed, the method may comprise reversing the previous reduction in dosage, optionally via one or more intermediate steps.

If the reported side effect data indicates persistent severe side effects that do not respond to a dosage reduction, the method may comprise alerting a HCP for input. For example, the HCP may recommend alternative treatment. In this way, patients who experience persistent unacceptable side effects, despite a reduction of dosage to provide a plasma level well below 50 nmol/L, can be rapidly identified as unsuitable for semaglutide therapy and the therapy can be withdrawn. Such identification can happen much faster than the recommended approach of withdrawing treatment after six months. This can advantageously save cost for the patient and/or medical authority as such therapy can be expensive.

It is recognised that a clinical problem can arise in determining whether reported side effect symptoms are a consequence of the drug, or are due to some other pathology which has arisen. For example, reflux and vomiting may be due to development of an ulcer or a malignancy. Diarrhoea could be due to a gut infection such as *Clostridium difficile* or development of inflammatory bowel disease. Constipation may be due to a tumour. Therefore, the method may comprise comparing the reported side effect data to the side effect trajectory and reporting, to the patient or HCP, side effects that have a severity rating that significantly exceeds the side effect trajectory. In this way the method can advantageously track the predicted envelope of drug symptoms for any particular patient based on both the underlying models and also patient progress data, and identify an unexpected deviation that can be flagged to highlight the need for alternative diagnoses to be considered.

The method may also comprise monitoring the reported side effects data for signs of toxicity arising from the drug. The drug label for semaglutide includes warnings regarding the potential for thyroid cancer and endocrine neoplasia. The method may comprise alerting a HCP if the reported side effect data includes symptoms of toxicity.

The method may adjust the dosage of semaglutide in response to side effects in the same way for the treatment of obesity and/or diabetes (other than the actual values of dose and plasma level may be different). One variation may relate when semaglutide is administered for the treatment of diabetes in combination with obesity. In such examples, the method may respond to reported side effects by reducing the dosage to a low level (e.g. 15 nmol/L) that is sufficient to provide glycemic control to treat the diabetes while only providing a limited hunger suppression effect. In this way, the method can maintain glycemic control while and prioritize side effect reduction over maintaining weight loss progress.

Dose Adjustment in Response to Weight Loss Progress

Dose adjustment in response to patient weight loss may differ depending on whether the incretin pathway drug such as semaglutide is administered: (i) solely for the treatment of obesity/weight loss; (ii) for the treatment of type 2 diabetes and obesity/weight loss; or (iii) solely for the treatment of diabetes. Each of these treatment purposes is discussed in turn.

Obesity/Weight Loss

The method may comprise comparing the patient weight loss data to the patient weight loss trajectory to review whether weight loss is on track. The method may perform such comparisons periodically, for example at the times corresponding to the weight loss milestones of the weight loss trajectory.

If the comparison indicates that the patient weight loss is less than a prediction range of the weight loss trajectory, the method may comprise increasing the drug dosage and indicating the increased dosage. Increasing the drug dosage may comprise increasing dosage amounts or a rate of increase in dosage amounts as defined above. The method may increase the drug dosage by increasing the nominal drug dosage regimen, e.g. by bringing forward a planned dose increase or by increasing one or more dosage amounts, within a regulatory approved dosage range. The method may comprise increasing the drug dosage by increasing the target plasma level and processing the increased target plasma level and the updated patient data to determine an updated nominal dosage regimen. The method may comprise increasing the drug dosage only if an elapsed time since a previous dosage increase exceeds a drug effect time threshold (in other words the plasma level has had sufficient time to reach steady state since the latest drug dose increase). The method may also optionally comprise increasing the drug dosage only if the patient progress data indicates that the patient is satisfying an adherence to a co-therapy behavioural regimen, e.g. calorie intake data complies with a calorie intake regimen. However, for some patients dietary concordance may only be possible by increased drug dosage.

If the comparison indicates the patient weight loss is on track, the method may maintain and indicate the drug dosage regimen.

If the comparison indicates the patient weight loss is greater than expected, the method may comprise reducing the drug dosage and indicating the reduced dosage.

The method may comprise reducing the drug dosage via an empirical/incremental decrease to the nominal dosage regimen or a decrease to the target plasma level (in the same way as described above for increasing dosage adjustments). The method may comprise decreasing the drug dosage only if an elapsed time since a previous dosage decrease exceeds a drug effect time threshold (in other words the plasma level has had sufficient time to reach steady state since the latest drug dose decrease). In this way, the dosage may correspond to the minimum dosage that can sufficiently manage weight loss/hunger. As a result, the cost of the recommended dosages can be minimised.

Diabetes and Weight Loss/Obesity

When the incretin pathway drug such as semaglutide is administered for the treatment of diabetes in combination with weight loss/obesity (e.g. when obesity is the primary driver of T2D), the method may adjust the dosage in response to weight loss progress in the same way as described above for obesity only. However, as noted above, the method may prioritize side effect control over weight loss progress by reducing the dosage to a level sufficient for glycemic control but having limited support for weight loss. In such examples, the method may not adjust the dosage even if the patient weight loss is less than a prediction range of the weight loss trajectory.

Diabetes Only

As noted above, type 2 diabetes can occur from factors other than obesity. In such examples, weight loss may be undesirable or even lead to adverse consequences.

Therefore, when the incretin pathway drug such as semaglutide is administered for the treatment of diabetes, the method may compare the weight loss data to a weight loss limit. If the weight loss data indicates a patient weight loss exceeding the patient weight loss limit, the method may reduce a dosage of the incretin pathway drug/semaglutide and indicate the updated dosage. The weight loss limit may relate to an absolute weight loss, a percentage weight loss, or a rate of weight loss. The weight loss limit may be determined based on the patient weight or BMI.

Dose Adjustment in Response to Satiety Data & Calorie Intake Data

For incretin pathway drugs such as semaglutide administered for obesity, similar to the dose adjustment in response to weight loss monitoring described above, the method may comprise monitoring the related parameters of patient satiety/hunger score and calorie intake and adjusting the dosage in response. Actual weight loss, satiety/hunger and calorie intake are all subtly different measures and the method may monitor one or more. For example, actual weight loss may be on track despite the patient experiencing a high level of hunger because of a strong patient motivation to succeed. Relying on motivation alone can risk relapse and therefore the method may advantageously ensure all of satiety/hunger, weight loss and calorie intake are well controlled.

The method may comprise receiving the patient satiety score and optimally titrating the drug dosage to sufficiently control satiety to result in a downward trajectory of weight. The method may comprise selecting the smallest dose and the shortest treatment duration to achieve the weight loss.

The method may comprise determining an incretin pathway drug/semaglutide drug dosage that controls hunger sufficiently to achieve consistent weight loss towards the target weight. The method may comprise iteratively adjusting the dosage up or down in order to maintain a level of satiety that continues to promote weight loss. There may be a number of ways of monitoring whether satiety is sufficient to promote weight loss. For example, simply ensuring that satiety remains higher than a threshold and increasing the drug dosage amount if not. The method may also comprise checking if satiety is sufficiently high to suggest that the drug dosage may be reduced. It may be advantageous to maintain as low a drug dosage as possible to reduce cost, improve the prospects for successful drug withdrawal and to minimise side effects.

A detailed description of monitoring satiety data and adjusting the dosage in response is described below in relation to FIG. 6. In brief, a method that adjusts drug dosage in response to satiety may comprise: increasing a drug dosage if the patient satiety score is less than a lower satiety threshold. The lower satiety threshold may be set at a level that indicates that the patient is at risk of not complying with the calorie intake regimen or not losing weight. The method may also comprise decreasing the drug dosage if the patient satiety score is greater than an upper satiety threshold. The upper satiety threshold may be set at a level that indicates that a dosage reduction could be implemented and maintain a satiety level sufficient for weight loss. The lower and upper thresholds may be calibrated and set for each individual patient, for example based on their response to a series of questions.

The method may comprise receiving the calorie intake data and updating the drug dosage in response. The method may comprise increasing the drug dosage if the calorie intake data exceeds a calorie intake allowance. The calorie intake allowance may be set according to the patient weight loss trajectory and/or the expected calorie intake trajectory. For example, the calorie intake allowance may be set according to an upper trajectory of the expected calorie intake trajectory.

In examples involving a co-therapy with a behavioural regimen, the method may comprise recommending an improved dietary concordance via patient education prior to increasing the drug dosage. For example, the method may comprise recommending alternative dietary plans or recommending different calorie types etc.

In the same way as described for adjusting the dosage in response to patient weight loss data, the method may only adjust the dosage in response to the patient satiety score or calorie intake data if an elapsed time since a previous dosage change exceeds a drug effect time threshold (in other words the plasma level has had sufficient time to reach steady state since the latest drug dose change).

Dose Adjustment in Response to Diabetes Metric Data

For incretin pathway drugs such as semaglutide administered for diabetes (optionally in combination with obesity/weight loss) the method may adjust the dosage based on the diabetes metric data of the patient progress data.

For example, the method may comprise reducing the dosage if the diabetes metric data is representative of a risk of hypoglycaemia and indicating the updated dosage. As noted above, diabetic patients who administer insulin may be at a particular risk of hypoglycaemia when taking GLP1. The diabetes metric may comprise CGM data and the method may determine a risk of hypoglycaemia as a rate of change/trajectory of blood glucose levels towards hypoglycemic levels exceeding an acceptable rate threshold. The method may determine the risk in other ways, such as counting the number of instances that glucose level drops below a lower glucose threshold (e.g. 3.5 mmol/L) over a time window, e.g. a day, a week etc.

The method may comprise reducing the dosage if the diabetes metric data indicates glycemic control within normal range (e.g. CGM data indicates blood glucose contained in range 3.3-5.5 mmol/L) and indicating the updated dosage. As illustrated in FIG. 2B, the effect on glycemic control varies slowly with changing plasma level between 15 nmol/L and 40 nmol/L. Therefore, the method may reduce the dosage to identify a minimum dosage sufficient for glycemic control. Such an approach can minimise side effects and reduced cost. Furthermore, if the patient is undertaking a behavioural co-therapy to improve their lifestyle, the improvement in glycemic control from the lifestyle changes may allow for a reduction and eventual withdrawal of the incretin pathway drug/semaglutide.

The method may comprise increasing the dosage if the diabetes metric data indicates an improvement in glycemic control that is less than a threshold improvement (e.g. reduction in average blood glucose is less than a threshold reduction or reduction in number of peaks above a blood glucose level is less than a threshold number).

Withdrawal of Treatment in Response to Satiety Data & Calorie Intake Data

Incretin pathway drugs such as semaglutide can be expensive. Therefore the method may rapidly identify patients who are unsuitable for treatment and recommend their withdrawal to save costs.

For example, for semaglutide for obesity, the method may comprise recommending patient withdrawal if: the reported side effect data indicates persistent intolerable side effects (e.g. despite a target plasma level reduction to 25-50 nmol/L), the patient weight loss data indicates persistent less than expected weight loss and/or the calorie intake data indicates a persistent lack of compliance with a calorie intake regimen co-therapy. In this way, the method can rapidly identify patients unsuitable for GLP1 therapy and in a faster way than the approved approach of withdrawing patients who have lost<5% body weight after six months.

For semaglutide for diabetes, the method may comprise recommending patient withdrawal if: the reported side effect data indicates persistent intolerable side effects (e.g. despite a target plasma level reduction to 25-50 nmol/L) or the diabetes metric data indicates a persistent lack of improvement in glycemic control.

Updating Expected Trajectories, Dosage Calculator & PK Model

The method may comprise updating the one or more expectation trajectories based on the updated dosage and the patient progress data. Updating the one or more expectation trajectories may comprise processing the updated dosage and the patient progress data with the dosage calculator and optionally any energy intake and expenditure model.

The method may also comprise updating or personally calibrating the dosage calculator, the PK model and/or the EI/TDEE model based on the patient progress data. For example, for obesity, the method may comprise calibrating the dosage calculator by applying a personalised scaling factor based on the patient weight loss data. The method may also comprise receiving a patient metabolism metric from a physiological test. The patient metabolism metric may comprise, a drug plasma level, another drug blood level (e.g. whole blood, serum), an incretin hormone level (e.g. a GLP1 level), a HbA1c level, or a glucose level from a blood test. The patient metabolism metric may also comprise a ketone breath test, a urine ketostix test, a $CO_2$ breath measurement or some other physiological marker of catabolic state. The patient metabolism metric may be used as a measurement of glycemic control and/or as a proxy of drug plasma level (or other physiological drug concentration). Therefore, the method may calibrate the dosage calculator or underlying PK model based on the patient metabolism metric. The method may also comprise updating an EI/TDEE model of a dosage calculator (e.g. the second example dosage calculator) based on the physical activity data and the calorie intake data of the patient progress data. The method may further comprise updating the drug dosage and/or the one or more expectation trajectories, such as the weight loss trajectory, based on the updated EI/TDEE model or dosage calculator.

The method may also comprise calibrating the dosage calculator and/or underlying PK model at a population level based on patient data received from a population of patients. The patient data may include patient metabolism metrics as described above. In this way the dosage calculator/PK model can be revised and improved, either to include or better accommodate determinants of weight loss and glycemic control, and/or calibrate the drug dosage required for glycemic control or weight loss (intermediate or equilibrium time points). The revised model may include relationships between drug dosage and weight loss/glycemic control directly or via the calculated predicted plasma concentration. As an example, the method can analyse population data and determine a dependence of bariatric surgery history on weight loss in a revised PK model. As a further example, the method may determine improved values for the population-average EI deficit profile and the population-average plasma level of the second example dosage calculator. The method may also collate data to improve the predetermined relationship data underpinning the plasma level—drug effect relationships of FIGS. 2A and 2B. The method may determine the effect of patient data parameters on such relationships to provide a more accurate PKPD model and dosage calculator.

Indicating the Dosage

As disclosed herein "indicating the dosage" refers to indicating a dosage recommendation (or updated dosage recommendation) for consideration by a patient or HCP. The term does not encompass an instruction for the patient or clinician to administer a dosage.

In some examples, the disclosed methods may further comprise instructing a patient or clinician to administer the indicated dosage (or indicated updated dosage).

In some examples, the method may comprise processing the (updated) patient data to determine an ideal dosage and selecting the dosage for administering to the patient from a selection of available doses based on the ideal regime.

The selection of available doses may depend upon the dosage route. For subcutaneous semaglutide the selection of available doses may comprise approved dosages including one or more of 0.25, 0.5, 1.0, 1.7 and 2.4 mg administered once weekly (for obesity) and 0.5 and 1.0 mg and 2.0 mg (for diabetes).

The selection of available dosage regimens may comprise the currently available dosage amounts of subcutaneous tirzepatide, which are 2.5, 5, 7.5, 10, 12.5, and 15 mg administered once weekly. The selection of available dosage regimens may also comprise any dosage amount not currently available administered at any frequency by any route of administration.

The disclosure envisages further approved dosages (for diabetes and/or obesity) and in particular personalised dosing enabling individual patients to be provided with any dosage between a minimum dosage and a maximum dosage. Therefore, the selection of available dose amounts for subcutaneous semaglutide may comprise: any multiple of 0.05 mg; or any multiple of 0.1 mg, administered once weekly, twice weekly or pro-re nata (prn). The selection of available dose amounts for oral semaglutide may comprise: any multiple of 0.25 mg; or any multiple of 0.5 mg, administered once daily, twice daily or prn.

In some examples, the selection of available doses for subcutaneous semaglutide may include one or more of: 0.1, 0.2, 0.4, 0.6, 1.0, 1.4, 1.8, 2.2, 2.6, 3.0, 3.6 or 4.2 mg administered once weekly; or half these doses if administered twice week; or quarter these doses if taken prn. The selection of available doses for oral semaglutide may include one or more of: 1.0, 2.0, 5.0, 10, 15, 20 or 30 mg administered daily; or half these doses if administered twice daily or prn.

The selection of available dosage regimens may comprise dosage amounts of subcutaneous tirzepatide comprising any integer multiple of 0.5 mg from 0.5 mg up to 60 mg once weekly.

The selection of available dosage regimes may comprise dosage amounts comprising: 0.25, 0.5, 1.0, 1.7, 2.0, 2.4, 3.4 and 4.8 mg subcutaneous Cagrisema once weekly.

The selection of available dosage regimes may comprise dosage amounts comprising dosage amounts of subcutaneous Cagrisema comprising any integer multiple of 0.05 mg from 0.05 mg up to 10.00 mg.

In some examples, the dosage calculator may determine the dosage as a dosage amount in combination with a dosing frequency. The dosing frequency may comprise an approved dosing frequency such as once weekly for subcutaneous semaglutide, subcutaneous tirzepatide and subcutaneous Cagrisema. In some examples, the dosing frequency may comprise a different frequency such as every 5 days, or every 10 days, or weekly for 3 months and then a holiday etc.

As noted earlier, the indicated dosage may comprise a dosage regimen based on the selection of available doses. For example, an indicated dosage for subcutaneous semaglutide may comprise a weekly dosing schedule comprising a recommendation to:

Start Wegovy® (subcutaneous semaglutide) at a dose of 0.25 mg once a week for your first month For your second month, you can increase your weekly dose to 0.5 mg For your third month, you can increase your weekly dose to 1 mg For your fourth month, you can increase your weekly dose to 1.7 mg For the fifth month onward, you can increase your weekly dose to the full dose of 2.4 mg In some examples, the disclosed systems and dosage calculators may indicate a separate agent to be administered in addition to or alternatively to the incretin pathway drug. For example, the system/dosage calculator may indicate that a drug with a different mechanism of appetite suppression such as metformin, oxytocin or phentermine and/or topiramate should be administered. The system/dosage calculator may indicate the separate agent for administering based on the pharmacogenomic profile, for example if the phenotype of the patient is "hungry brain."

Weight loss arising from the incretin pathway drug may result in a loss of muscle mass. In some examples, the system/dosage calculator may indicate a separate agent for administering that counteracts the muscle loss such as a myostatin inhibitor.

As noted below, the system may include a behavioural therapy aspect to address non-compliant weight loss, muscle loss and other factors. In this way, the system, can include both behavioural therapy mitigations, delivered with personalised posology, and/or additional pharmacological therapies (either a separate drug or a drug with an additional mode of action), when below target weight loss is achieved with the incretin pathway drug alone.

Co-Therapy

Semaglutide may be administered as part of a co-therapy including a behavioural co-therapy. When semaglutide is administered for obesity, the behavioural therapy may include a calorie intake regimen and/or a physical activity regimen. When semaglutide is administered for type 2 diabetes, the behavioural therapy may include a calorie intake regimen, a physical activity regimen and/or a sleep regimen.

Obesity—Dietary Co-Therapy

It is well recognised that to achieve optimal effect, additional behavioural measures need to be enacted, in particular altered food intake and also exercise. Embodiments of the disclosure relate to methods of optimising the behavioural measures in relation to the incretin pathway drug. This may include optimising the timing of introduction of the measure in relation to the drug prescription and changes in drug dose, as well as variations in the intensity of the behavioural action.

In relation to dietary modification, the hardest element is the initial change, for example to smaller portion sizes or a change in food composition, such as removal of highly processed foods or a decrease in carbohydrate intake, particularly non-complex carbohydrates such as simple sugars.

Once such change has been established, then it is easier to maintain. The optimal time to establish such change may be immediately following each dosage increase, before any downstream receptor adaptation has occurred and corresponding to when nausea is more likely to occur.

In contrast, an increase in an exercise regimen can be easier to achieve when side effects are at their minimum, and some weight loss has already been established, corresponding to the longest time after a dose change and prior to a dose escalation, or if on the maximal dose, once side effects have plateaued. The disclosed embodiments may therefore indicate the introduction or adjustment of a calorie intake regimen immediately following a dose change or after a drug effect time enabling the drug plasma level to reach steady state and indicate the introduction or adjustment of an exercise regimen prior to a dose change or at a time when side effects have plateaued.

Figure 5:
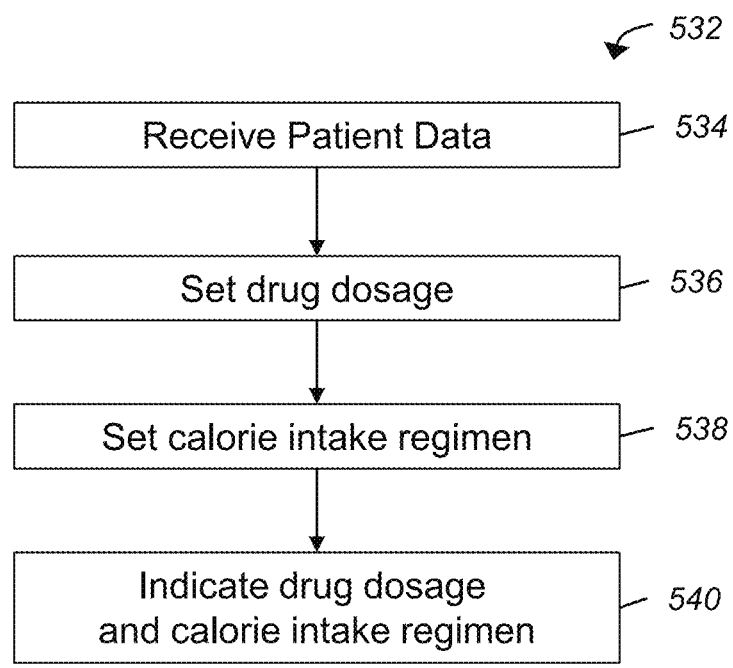
FIG. 5 illustrates a method for treating obesity in a patient according to an embodiment of the present disclosure.

FIG. 5 illustrates a method 532 for generating a co-therapy for a patient for the treatment of obesity according to an embodiment of the present disclosure. The co-therapy comprises an incretin pathway drug for administering to the patient according to a dosage regimen and a digital therapeutic program comprising a behavioural regimen for administering using an electronic device.

A first step 534 comprises receiving personalised patient data. The first step 534 may correspond to step 102 of FIG. 1 of receiving patient data described in detail above.

A second step 536 comprises setting an incretin drug dosage of the dosage regimen based on the personalised patient data. The second step 536 may correspond to step 104 of FIG. 1 described in detail above. For example, step 536 may comprise processing the personalised patient data with any of the above described dosage calculator to determine the incretin drug dosage.

A third step 538 comprises setting a calorie intake regimen of the behavioural regimen based on the personalised patient data.

A fourth step 540 comprises indicating the incretin drug dosage and the calorie intake regimen. The method may comprise indicating the incretin drug dosage and the calorie intake regimen to a patient and/or a healthcare provider (HCP) (which refers to practitioners generally (carers, nurses, pharmacists, doctors) but may also be referred to herein as a clinician). As described herein "indicating the incretin drug dosage and the calorie intake regimen" refers to indicating a recommended incretin drug dosage and a recommended calorie intake regimen to a patient or clinician. It does not encompass an instruction to administer an incretin drug dosage or undertake a calorie intake regimen. The method may comprise indicating the incretin drug dosage and the calorie intake regimen simultaneously or at separate times.

The method of FIG. 5 may be seen as an extension of the embodiments described above or may be performed independently. The incretin drug may comprise semaglutide tirzepatide, or Cagrisema and may utilise any of the specific examples described above. The incretin drug may comprise other GLP1 agonists, GIP agonists or any other incretin pathway drugs.

In some examples, the digital therapeutic program (which may simply be referred to herein as the digital program) may indicate the behavioural regimen to the patient. The behavioural regimen may comprise the calorie intake regimen and/or a physical activity regimen. The behavioural regimen may be delivered to the patient via an electronic device, for example the patient device, described below in relation to FIG. 16. The digital program may be configured to synchronise a timing of the behavioural regimen with a timing of the administration of the GLP1 dosage.

As well as indicating the recommended drug dosage and calorie intake regimen, the digital program may also output instructions for delivering the treatment regimen. For example, the digital program may instruct the patient (or a clinician) to administer the indicated incretin drug dosage according to the dosage regimen. The digital program may provide the instruction via the electronic device. The digital program may indicate, and optionally instruct administration of, the dosage regimen as one or more dosage amounts and/or one or more corresponding dose timings to the patient.

The digital program may manage the patient weight loss and the treatment regimen in a four stage treatment protocol. The four stages may comprise: (i) an initial treatment titration phase; (ii) a progressive weight loss phase; (iii) a weight maintenance phase; and (iv) a drug withdrawal phase. In some examples, two or more of the stages may be combined. In some examples, stages (i) and (ii) may be grouped together and referred to as the weight loss phase. In some examples, stages (iii) and (iv) may be combined and referred to as the weight maintenance phase. In some examples, one or more stages may be separated into sub-stages.

By providing a staged approach, the digital program can recommend a co-therapy approach that can advantageously initiate and embed a behavioural change in the patient's lifestyle during the initial phases that is coordinated with the incretin drug treatment which suppresses their hunger. As the lifestyle changes become embedded, the patient can continue with a healthy diet and physical activity regimen as the incretin drug dosage is reduced or withdrawn during the drug withdrawal phase. In this way, the method can avoid chronic incretin drug dosing and patients can be weaned off the drug. This is particularly advantageous in jurisdictions where some drug treatments are only authorised for fixed durations (e.g. semaglutide is approved in the UK for 2 year treatment periods).

Initial Treatment Titration Phase

At the start of the treatment, the digital program may set or determine an initial incretin drug dosage. As described herein, "setting, determining or adjusting an incretin drug dosage" may refer to setting one or more dosage amounts or dosage timings of a dosage regimen of the incretin pathway drug. Setting, determining or adjusting the incretin drug dosage may refer to setting, determining or adjusting a dosage titration trajectory or ramp profile in which a dosage amount is gradually increased and/or decreased in discrete steps over a period of time (e.g. as the drug is first introduced at the start of treatment or withdrawn at the end of treatment). The ramp up in the initial incretin drug dosage regimen may be scheduled as a series of stepwise escalations, for example increments in dosage every four weeks over a period of 12-24 weeks (see table 1 above).

The digital program may set the initial incretin drug dosage based on a manufacturer's recommendation for the particular dosage form of the incretin pathway drug. In some examples, the digital program may set a personalised initial incretin drug dosage based on one or more of: patient data including patient genotype, patient phenotype, patient demographic data such as gender, ethnicity and/or age; patient physiological data such as patient weight, kidney function, basal metabolic rate, lean body mass and/or fat levels; and/or patient behavioural data such as calorie intake (including type of food consumed, water intake and timing (e.g. time since last meal), satiety, motivation to calorie restrict, and physical activity levels. The digital program may set the initial incretin drug dosage by processing the personalised patient data using a dosage calculator as described above. The digital program may set the initial incretin drug dosage based on patient weight which can be a key driver of incretin drug plasma level. The digital program may set the initial incretin dosage using a dosage calculator derived from a pharmacokinetic (PK) model and optionally a EI/TDEE model (e.g. any of the first to fourth example dosage calculators). The digital program may set the initial drug dosage based on a target weight loss. For example, as described above, the digital program may determine a target plasma level to achieve the target weight loss based on a predetermined plasma level to weight loss relationship. The digital program may then determine the initial drug dosage based on the target plasma level and the patient initial weight. In some examples, the digital program may skip the intermediate calculation of the target plasma level and determine the initial drug dosage based on the target weight loss and the initial weight using a predetermined relationship such as a look up table. The predetermined relationship may be derived from patient study data and/or the PK model.

The digital program may set the initial calorie intake regimen based on an initial weight of the patient and a target weight of the patient. The target weight may be agreed between the patient and a clinician when the treatment is prescribed. The clinician may also prescribe a treatment period over which the co-therapy will be administered to the patient and by which the target weight should be achieved. In some examples, the treatment period may be between 12 and 36 months, for example 24 months. In some examples, the treatment period may be indefinite. In some examples, the treatment period may only apply to the incretin drug regimen and the calorie intake regimen may be indefinite. The digital program may receive the initial weight and the target weight, for example via user input on a user interface of an electronic device. The digital program may set a weight loss trajectory based on the initial incretin drug dosage and/or the initial calorie intake regimen. As described above, the weight loss trajectory may be based on a typical weight loss versus dosage trend from patient studies or from a PK model (e.g. the decay profile of FIG. 14). As also described above, the weight loss trajectory may also be based on a EI/TDEE model which may be part of the dosage calculator. The weight loss trajectory may define a series of weight loss milestones between the initial weight and the target weight at periodic time points within the treatment period. The weight loss trajectory may include a prediction range, or expectation range, surrounding the nominal weight loss trajectory comprising an upper weight loss trajectory and a lower weight loss trajectory. The expectation range may define an acceptable weight loss trajectory.

The calorie intake regimen may include a calorie intake allowance, such as a calorie intake allowance for specific meals, a daily calorie intake allowance, a weekly calorie intake allowance etc. The calorie intake allowance may equate to a calorie restriction relative to the patient's calorie intake prior to the treatment. The digital program may determine a minimum degree of calorie restriction required to reach the target weight.

The digital program may receive dietary options data to indicate the range of dietary restrictions available to the patient, for example, whether or not a substitution diet is available. The initial calorie intake regimen may provide the calorie intake regimen based on the dietary options data. For example, the calorie intake regimen may recommend a substitution diet, if the dietary options data indicates one is available. While some patients may perform well with prescriptive meal substitution, others may only be able to access, or require, a more modest calorie restriction. For example, the initial calorie intake regimen may include recommendations to remove a single item from daily consumption, corresponding to the required calorie reduction as calculated to reach the desired weight. More generally, the calorie intake regimen may also recommend consumption or avoidance of certain food types, e.g. whether protein, carbohydrate or fat, then subtype of food type, for example complex carbohydrate or simple sugar. The calorie intake regimen may also include recommendations for a frequency of calorie consumption. For example, the calorie intake regimen may recommend whether food should be eaten at regular time points during the day, whether meals should be skewed with a larger meal at one particular time, whether there are liquid calories and whether any snacks are permitted between meals.

The digital program may set a timing of the initial calorie intake regimen based on a start time of the incretin drug dosage regimen. For example, the digital program may indicate a delay to the onset of the calorie intake regimen by a drug effect time relating to the time for the incretin pathway drug to have an effect on the patient satiety (or a time for a drug plasma level to reach steady state). In this way, the digital program can recommend a timing for the start of calorie restriction that is synchronised or coordinated with the onset of the satiety effect of the incretin pathway drug. Delaying the initial calorie intake regimen can advantageously improve patient adherence (also referred to herein as concordance) to the calorie intake regimen as the patient perceives the new calorie regime as easier to achieve due to the hunger suppressing effect of the incretin pathway drug. As explained below, the digital program may modify the timing of the delay based on a motivation score of the patient. The intrinsic motivation to alter diet and calorie restrict can be highest at initiation of therapy, even though the actual effect on satiety and hunger will be less from the incretin pathway drug as the dosage/plasma concentration has not yet increased to a steady state value and/or taken effect.

The digital program may receive other parameters for determining and setting the initial calorie intake regimen. For example, the digital program may receive a current calorie intake for the patient. The digital program may set a ramp profile of the initial calorie intake regimen to ramp from the current calorie intake to a reduced calorie intake allowance that can achieve the target weight loss. The digital program may also receive a motivation score of the patient indicating a motivation level of the patient for losing weight. The digital program may receive the motivation score as a scalar input on a user interface of the patient electronic device. The digital program may adjust the timing of the initial calorie intake regimen based on the motivation score. For example, the digital program may increase the ramp rate or reduce the drug effect delay time for patients with high motivation or vice versa.

The greater the calorie restriction, the greater the weight loss. However, a greater calorie restriction is behaviorally harder to achieve. Furthermore, as the patient loses weight, the homeostatic mechanism tending to revert weight to a particular set point becomes stronger and therefore it's harder to continue with the calorie restriction. Drug labels for incretin pathway drugs such as GLP1 agonists typically prescribe a ramp up in dosage amount over a number of weeks. The increasing dosage can address the increasing difficulty in adhering to a calorie restriction resulting from the homeostatic mechanism. However, the drug labels prescribe a fixed dosage ramp/titration trajectory and do not allow for individual variation in circumstances, motivation, drug efficacy, side-effects and other personalised influences on the treatment adherence and weight loss. The disclosed systems and methods can determine and indicate a personalised incretin drug dosage regimen in combination with a personalised behavioural regimen. As the patient progresses with the therapy, the systems and methods can advantageously adapt both elements of the co-therapy to the patient's personal treatment response, and indicate the updated co-therapy. In this way, greater patient adherence and sustained weight loss can be achieved even as the incretin pathway drug is eventually withdrawn.

Following initiation of the incretin dosage regimen, the digital program can monitor patient progress data. The patient progress data may include one or more variables indicating the progress of their dietary restriction and weight loss. The patient progress data may comprise any of the patient progress data described above.

The digital program may adjust the incretin drug dosage and/or the calorie intake regimen based on the patient progress data. Adjusting the incretin drug dosage may comprise increasing or decreasing a dosage amount of one or more doses of the dosage regime, adjusting one or more dosage timings of the one or more doses, increasing or decreasing a ramp rate of a dosage increase or decrease of the dosage regimen etc. Adjusting the calorie intake regimen may comprise: increasing or decreasing a calorie intake allowance, increasing or decreasing a rate of change of the calorie intake allowance or adjusting one or more timings of calorie intake or types of food consumed. The digital program may indicate the adjusted incretin drug dosage and may indicate the adjusted calorie intake allowance.

Figure 6:
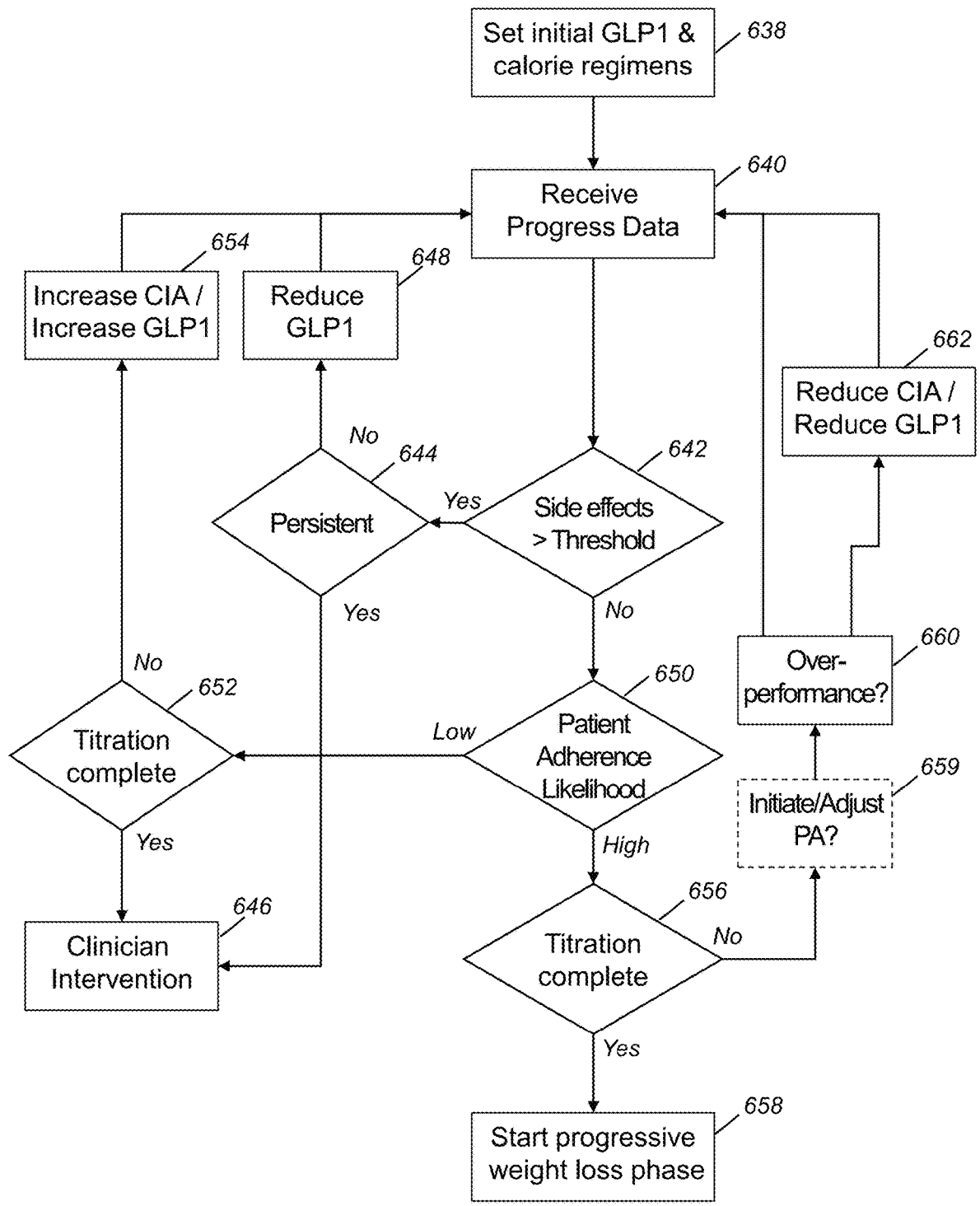
FIG. 6 illustrates a method of adjusting the treatment during the initial treatment titration phase according to an embodiment of the present disclosure.

FIG. 6 illustrates a method of adjusting the incretin drug dosage regimen and the behavioural regimen during the initial treatment titration phase according to an embodiment of the present disclosure. The method may be performed by the digital program. The method of FIG. 6 relates to monitoring patient progress and adjusting the co-therapy in response. The method may further comprise indicating (or recommending) the adjusted co-therapy e.g. to a patient or HCP.

A first step 638 comprises setting and indicating the initial incretin drug dosage and the initial calorie intake regimen as described above.

A second step 640 comprises receiving the patient progress data.

A third step 642 comprises determining if the patient side effect data is representative of a level of side effects greater than a side effect intolerance threshold. The side effect intolerance threshold may comprise a timeframe, for example a level of nausea has been unacceptable for a number of consecutive days. The intolerance threshold may simply comprise the patient reporting that they cannot tolerate one or more side effects.

If the level of side effects is greater than the intolerance threshold the method proceeds to decision point 644 to determine if the level of side effects have been persistently greater than the intolerance threshold, for example the intolerance threshold is persistently exceeded (over a number of iteration loops of FIG. 6) despite a reduction in incretin drug dosage or the patient is unable to tolerate a dosage level required for sufficient hunger suppression. If the side effects have been persistently greater than the intolerance threshold, the method proceeds to termination point 646 and clinician intervention. For example, the clinician may recommend an alternative treatment (e.g. surgery, different drugs). In this way, patients who experience persistent unacceptable side effects and are unsuitable for the specific drug therapy are rapidly identified. This can advantageously save cost for the patient and/or medical authority as some incretin drug therapies can be expensive.

Returning to step 644, if the level of side effects being greater than the intolerance threshold is not persistent, the method may proceed to step 648 and reduce the incretin dosage. The drug dosage reduction may be a reduction in dosage amount, a delay in a dose timing or a reduction/increase of the rate of increasing/decreasing dosage amounts. In some examples, the reduction in incretin drug dosage may be a temporary— it has been shown that side effects such as nausea improve over time when tolerance to the adverse side effects develop. In other examples, the reduction in incretin drug dosage may be permanent because the patient achieves greater weight loss and therapy concordance without the unwanted side effects. Following reduction and indication of the incretin drug dosage the method returns to step 640 and receives further progress data to continue to monitor the side effects.

Returning to the third step 642, the step may also comprise monitoring the reported side effects data for signs of toxicity arising from the drug. The drug label for semaglutide includes warnings regarding the potential for thyroid cancer and endocrine neoplasia. The method may comprise proceeding to step 614 and alerting a HCP if the reported side effect data includes symptoms of toxicity.

Step 642 may also monitor the reported side effect data for a patient willingness to proceed despite reporting severe side effects. If the patient indicates a willingness to proceed the method may discount the severe side effects.

At step 642 If the level of side effects is less than the side effect intolerance threshold or the side effect data indicates a patient willingness to proceed, the method proceeds to step 650 and estimates the likelihood of patient adherence to the calorie intake regimen. The digital program may estimate the likelihood of patient adherence based on the patient progress data in a number of ways. For example, the digital program may predict a low likelihood of patient adherence to the calorie intake regimen if: (i) the patient weight loss data indicates that the patient weight loss is behind schedule, i.e. the patient weight loss is less than the acceptable patient weight loss trajectory; (ii) the patient calorie intake data represents a calorie intake greater than a first upper calorie intake threshold (e.g. a proportional amount, such as 25%, above the calorie intake allowance); (iii) the patient motivation score is less than a lower motivation score threshold (e.g. less than 4 on a scale of 0-10); or (iv) the patient satiety score is less than a first lower patient satiety threshold (e.g. less than 5 on a scale of 0-10). The threshold comparison conditions may include not meeting the threshold for a persistent time period e.g. a consecutive number of days or a proportion of consecutive days (e.g. exceeding the calorie intake allowance by more than 25% for three days out of four). Each of these conditions may indicate that the patient is having, or will have, difficulty adhering to the calorie intake regimen. The patient may experience such difficulty particularly during the initial stages of the drug treatment when the drug dosage has not reached a maximum dosage amount and/or has not taken full effect. Therefore, if the method determines that the patient adherence likelihood is low (e.g. by meeting one of the conditions (i)-(iv)) the method proceeds to step 652 to check if the initial incretin drug dosage titration is complete. The initial GLP1 dosage titration may be complete when the drug dosage amount has increased to a maximum dosage amount and had sufficient time (e.g. 21 days) to have full effect in the patient (steady state drug plasma level).

If the initial incretin drug dosage titration is complete, the method proceeds to termination point 646 to seek clinician intervention because the maximum dosage and drug effect have failed to result in patient adherence to the calorie intake regimen. The clinician may provide better dietary options such as a substitution diet. For example, patients unable to maintain a 500 Cal/day reduction by reduced meal size/snacking may be prescribed an initial or even extended use of meal replacement options and return the patient to step 640. Alternatively, the clinician may stop the treatment and/or prescribe additional or alternative treatment (e.g. surgery or different drugs using a different mechanism of action such as metformin or topiramate). In some examples, the method may comprise adding such additional/alternative treatments to the co-therapy (either directly in response to step 652 or clinician adjustment) and adjust and indicate the dosages of the alternative/additional treatments in response to the patient data. In this way, patients who do not respond well to the therapy are rapidly identified which can advantageously save cost.

Returning to step 652, if the initial incretin dosage titration is not complete, the method proceeds to step 654 to adjust (and indicate) the incretin drug dosage and/or the calorie intake allowance to improve the patient adherence. For example, the method may indicate a temporary increase in the calorie intake allowance to allow the incretin drug dosage regimen to take effect in the patient. For example, the temporary increase may persist while the incretin drug dosage amounts are increased according to the initial incretin drug dosage titration trajectory resulting in associated improvements in the patient weight loss data, satiety score, motivation score, and/or calorie intake data. Alternatively, or in addition, the method may increase (and indicate) the incretin dosage. For example, the method may increase the ramp rate of the increasing dosage titration trajectory, bring forward a dosage increase or otherwise accelerate the incretin dosage increase. Following adjustment and indication of the incretin dosage and/or calorie intake regimen, the method returns to step 640 and continues to monitor the patient progress data.

Returning to step 650, if the method determines that the patient adherence likelihood is high, the method proceeds to step 656 to check if the initial incretin drug dosage titration is complete, in the same way as described for step 652. The method may also check if the initial calorie intake regimen is complete (i.e. a maximum planned calorie restriction has been achieved). If the initial incretin drug dosage titration is complete, i.e. the maximum dosage has been reached and the progress data is indicating tolerable side effects and patient adherence, (and optionally the initial calorie intake regimen is complete) the method proceeds to step 658 to indicate or recommend initiation of the second phase of the protocol—the progressive weight loss phase.

Returning to step 656, if the initial incretin drug dosage titration is not yet complete, this indicates that a drug dosage ramp-up and/or a calorie intake allowance ramp down is ongoing. In other words, the patient is on track. The method can proceed to optional step 659 and determine whether a physical activity (PA) regimen should be initiated or adjusted. The method may recommend timing of, initiation of, duration and intensity of physical activity (e.g. specific exercise) to correspond with the capabilities of the patient at a particular stage of their treatment process. The timing and intensity of the physical regimen may be titrated based on measurement of motivation and achievability as indicated by the progress data. The method may introduce a physical activity regimen if the weight loss data indicates patient weight loss exceeding a first weight loss milestone. Increased physical activity such as exercise can be easier to initiate when a patient has already undergone some weight loss. A small amount of weight loss can lead to a significant change in pressure on the patient's joints and cardiovascular system, thereby allowing increased activity. Furthermore, administering the incretin pathway drug and restricting calories will lead to a loss of both fat mass and lean mass in an approximately 3 to 1 ratio. A physical activity regimen can protect against the loss of lean mass. The method may recommend an increase in a level of physical activity intensity if: the weight loss data indicates patient weight loss exceeding one or more further weight loss milestones; the patient motivation score exceeds a second motivation threshold; or the patient activity data satisfies one or more activity thresholds. It will be appreciated that the method may also recommend a decrease in the intensity of the physical activity regimen, for example at step 654 if the patient has low motivation. In some examples, the method may only recommend the introduction of a physical activity regimen in later phases, such as the progressive weight loss phase or the weight maintenance phase.

Following step 659, the method proceeds to step 660 and assesses whether the patient adherence or weight loss is exceeding expectations. The method may determine the patient adherence or weight loss to be exceeding expectations if: (i) the patient weight loss data represents a weight loss ahead of schedule, i.e. exceeding the acceptable weight loss trajectory; (ii) the patient calorie intake data represents a calorie intake less than a first lower calorie intake threshold (e.g. a proportional amount, such as 25%, below the calorie intake allowance); (iii) the patient motivation score is greater than an upper motivation score threshold (e.g. greater than 7 on a scale of 0-10); or (iv) the patient satiety score is greater than a first upper patient satiety threshold (e.g. greater than 7 on a scale of 0-10). The threshold comparison conditions may include exceeding the relevant threshold for a persistent time period e.g. a consecutive number of days or a proportion of consecutive days (e.g. consuming less than the calorie intake allowance by more than 25% for three days out of four). Each of these conditions may indicate that the patient is exceeding the weight loss and/or adherence expectations.

If the method determines that the patient adherence or weight loss is exceeding expectations, the method proceeds to step 662 and adjusts (and indicates) the incretin drug dosage and/or the calorie intake regimen accordingly. For example, the method may reverse an increase in calorie intake allowance that was applied at step 654 at an earlier stage of the treatment to address poor adherence. Alternatively, patients may be able to adopt diets with greater energy restriction, and optionally increased energy expenditure via physical activity, while remaining on relatively low doses of incretin drug. Alternatively, or in addition, the method may reduce the incretin drug dosage. For example, the method may recommend reducing, delaying or cancelling future dosage increases of the drug titration trajectory. In this way, the method may recommend completing the initial drug dosage titration ahead of schedule, such that the method may proceed to step 658 on the next iteration. In some examples, the method may recommend reducing the target weight to a more ambitious target, optionally seeking clinician input for approval of the new target weight. Such an approach may be accompanies by a further reduction in calorie intake allowance. Patients may engage strongly with the formal energy intake restriction and increased physical activity elements of the protocol. Such patients may realise sufficient personal reserve to tolerate a more rapid weight loss programme arising from greater restriction of energy intake. Following step 662, the method returns to step 640 and continues to monitor the patient progress.

If the method determines that the patient adherence or weight loss is not exceeding expectations, the method may maintain (and indicate) the current GLP1 dosage and calorie intake regimen and return to step 640 to await further patient progress data.

The method of FIG. 6 may be performed iteratively and periodically, for example daily, weekly etc. Step 640 may be performed more frequently, e.g. satiety data and calorie intake data may be received multiple times per day. Such data may be stored and assessed on a moving average basis. The assessment of such data, particularly at steps 642, 650 and 658 and any corresponding adjustments at 648, 654 and 662 may be performed with a periodicity that allows time for any incretin drug dosage adjustments to take effect. In some examples, the iterations may correspond to the periodic timing of the weight loss milestones or scheduled reviews. In this way, the digital burden can be kept to a minimum for patients who are not technologically literate.

The method of FIG. 6 can initialize and indicate a personalised incretin drug, calorie intake and physical activity co-therapy regimen optimised for side effect mitigation and achievement of satiety. The stringency of calorie restriction can be adjusted according to the moving average of satiety or a related measure. If there is a desire for greater than the calorie intake allowance, absent high levels of motivation to temporarily live with uncomfortable degrees of hunger until a new incretin drug dose is reached, then a lower level of calorie restriction is recommended until a higher incretin drug dosage is reached and the moving average of satiety improves sufficiently to enable the greater degree of calorie restriction. The method of FIG. 6 can improve adherence rates and the effectiveness of incretin drug weight loss therapy because the method advantageously coordinates the timing of the calorie intake restriction with the effects of the incretin pathway drug. In this way, the method can reduce premature drop-outs from incretin drug therapy. However, the method can also rapidly identify patients who are not suitable for incretin drug therapy due to poor response and/or intolerable side effects.

The initial treatment titration phase can initiate and indicate the co-therapy regimen in a personalised manner and adjust and indicate the co-therapy regimen in a personalised manner in response to the patient progress data. In this way, the method can help initiate each patient in a personalised way and help advance them on to the progressive weight loss phase when the patient: has reached a stable drug dosage delivering a stable satiety level; is adhering to a restricted calorie allowance to promote weight loss; and is optionally engaging in a complementary physical activity regimen.

Progressive Weight Loss Phase

The protocol may proceed to the second phase—progressive weight loss phase following completion of the initial incretin drug dosage titration trajectory and optionally completion of the initial calorie intake regimen (completion of a calorie restriction ramp). The goal of the second phase is to reach a stable incretin drug dosage that provides persistent weight loss towards the target weight over a period of several months. The method may also comprise determining, maintaining and indicating a minimum dosage of the incretin pathway drug that will provide a patient satiety sufficient for the patient to adhere to the calorie intake regimen and the acceptable weight loss trajectory. Incretin pathway drugs can be expensive, so maintaining the minimum sufficient drug dosage can advantageously save cost for the patient and/or healthcare system.

Figure 7:
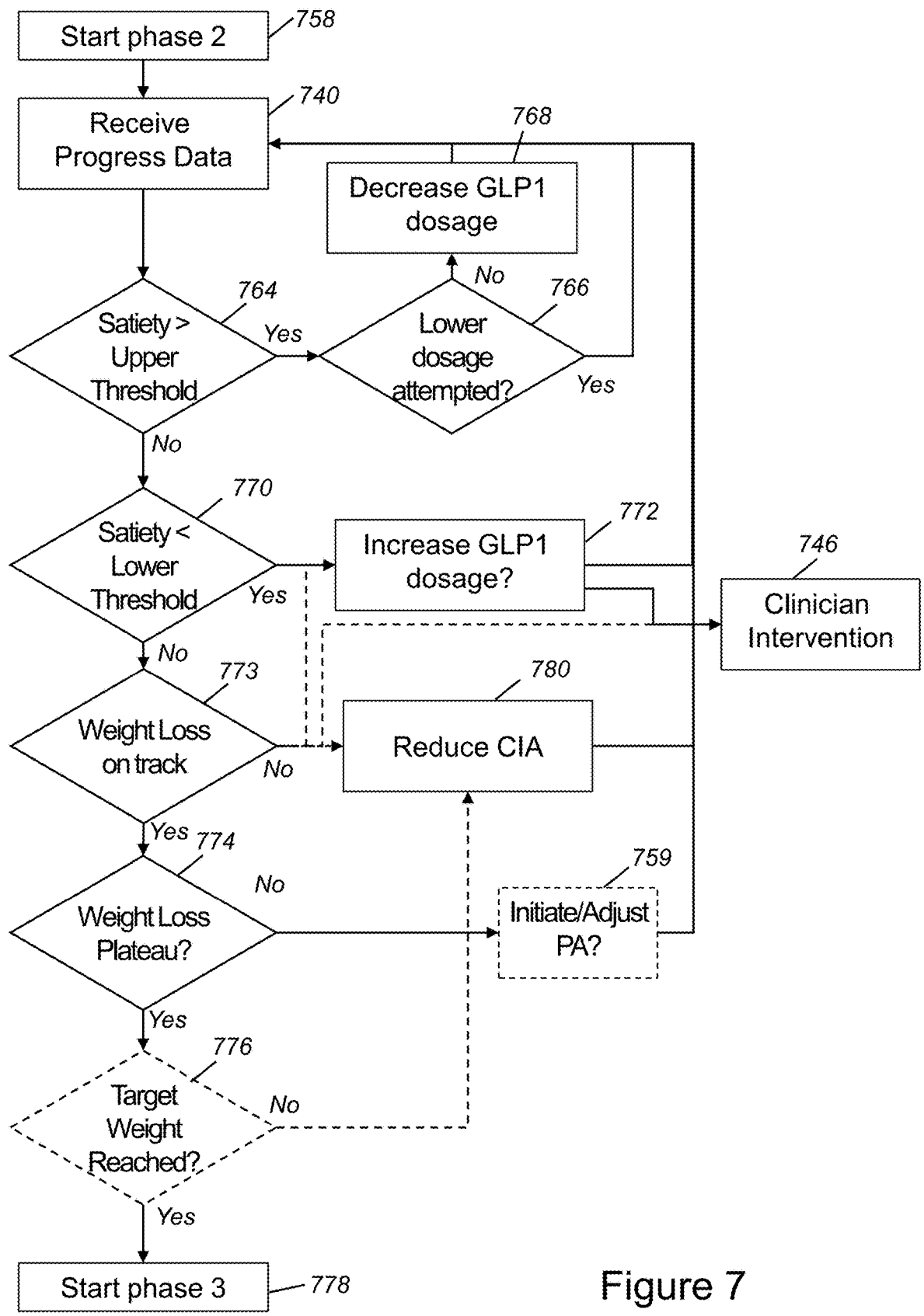
FIG. 7 illustrates a method of achieving a stable co-therapy regimen for the progressive weight loss phase according to an embodiment of the present disclosure.

FIG. 7 illustrates a method of achieving a stable co-therapy regimen for the progressive weight loss phase according to an embodiment of the present disclosure.

The method picks up where FIG. 6 left off at step 758 and commences the progressive weight loss phase. In the same way as described above for FIG. 6, the method iteratively and periodically receives 740 patient progress data. The period of the iteration may be the same as the first phase or may be longer because the incretin drug dosage and calorie intake regimens are more stable. In the progressive weight loss phase, patient weight loss data and satiety score are two of the key metrics monitored, however the other progress data parameters (e.g. motivation, side effects etc.) may be continued to be monitored, with the method responding accordingly.

As noted above, the second phase may determine an incretin drug dosage that controls hunger sufficiently to achieve consistent weight loss towards the target weight. The second phase may iteratively adjust (and indicate) the incretin dosage up or down in order to maintain a level of satiety that continues to promote weight loss. There may be a number of ways of monitoring whether satiety is sufficient to promote weight loss. For example, simply ensuring that satiety remains higher than a threshold and increasing (and indicating) the incretin drug dosage amount if not. The method of FIG. 7 also checks if satiety is sufficiently high to suggest that the incretin drug dosage may be reduced. It may be advantageous to maintain as low an incretin drug dosage as possible to reduce cost, improve the prospects for successful drug withdrawal and to minimise side effects. Although FIG. 7 focusses on satiety, other example methods may additionally or alternatively use other parameters such as calorie intake data to assess whether the patient's hunger is sufficiently controlled.

The method proceeds to step 764 to check if the patient satiety score is greater than a second upper patient satiety threshold (e.g. satiety score of 8 on a scale of 0-10). The second upper patient satiety threshold may be set at a level that indicates that an incretin drug dosage reduction could be implemented and maintain a satiety level sufficient for weight loss. The second upper patient satiety threshold may be the same as the first upper patient satiety threshold. If the patient satiety score is greater than the second upper satiety threshold, the patient may be able to tolerate a lower drug dosage and still experience a satiety score sufficient for weight loss. Therefore, the method proceeds to step 766 to check if a lower incretin drug dosage has previously been attempted (and unsuccessful). If so, the method maintains the current incretin drug dosage and returns to step 740. If the lower incretin drug dosage has not been previously attempted, the method proceeds to step 768 and reduces (and indicates) the incretin drug dosage before returning to step 740. In this way, the loop 740, 764, 766, 768 can ensure the incretin drug dosage is at a minimum level sufficient to promote weight loss towards the target weight. In some examples, an alternative to the steps of 766 and 768 may be to reduce the target weight for the patient to a more ambitious target, optionally including seeking clinician approval. Such an approach may be accompanied by a further reduction in the calorie intake allowance (which could take effect at step 780 described below).

Returning to step 764, if the satiety score is not greater than the second upper patient satiety threshold, the method proceeds to step 770 to check if the satiety score is less than a second lower patient satiety threshold. The second lower patient satiety threshold may indicate that the patient is at risk of not complying with the calorie intake regimen or not losing weight. The second lower patient satiety threshold may be the same as the first lower patient satiety threshold. Immediately following the first phase of FIG. 6, the satiety score should be greater than the first lower satiety threshold because it was a condition of exiting the first phase at step 650. However, on later iterations, patient satiety may increase following a reduction in incretin drug dosage (e.g. at step 768), a reduction in calorie intake allowance (step 780) and/or a change in personal circumstances, such as life events (stress, temporary illness, loss of a loved one etc.). If the satiety threshold is less than the second lower satiety threshold, the method proceeds to step 772 and attempts to increase (and indicate) the incretin drug dosage. The increase in incretin drug dosage may be dictated by whether the patient is currently on a maximum allowable dosage. If the patient is currently on the maximum allowable dosage, the dosage may be maintained and/or clinician intervention 746 may be sought. The clinician may stop treatment, recommend complementary treatment or adjust the target weight (see below). Following step 772 the method returns to step 740.

The combination of steps 764 and 770 provide a check that the satiety score is within an optimal range—higher than the second lower satiety threshold to promote sufficient weight loss and lower than the second upper satiety threshold which is indicative of an excessive drug dosage. Step 766 prevents yo-yoing between dosage levels either side of a sufficient satiety level by biasing the patient towards a higher dosage level. The use of two separate thresholds to define a satiety threshold range also reduces the risk of yo-yoing dosages.

Returning to step 770, if the patient satiety score is not less than the second lower satiety threshold, the method proceeds to step 773 to check if the weight loss is on track, for example if the weight loss is within the acceptable weight loss trajectory. If the weight loss is less than the acceptable weight loss trajectory, in other words the patient is not losing weight fast enough, the method may also, as part of step 773, determine if the calorie intake data represents a calorie intake less than the calorie intake allowance to ensure the patient is complying with the calorie intake regimen. The method may also comprise checking activity data to determine if the patient is adhering to a physical activity regimen. If the patient is complying with the calorie intake regimen (and optionally the physical activity regimen), the method may proceed to step 780 and reduce (and indicate) the calorie intake allowance before returning to step 740. If the patient is not complying with the calorie intake regimen (and optionally the physical activity regimen), the method may proceed to step 772 to increase (and indicate) the incretin drug dosage or to step 746 and seek clinician intervention to address the compliance issues. Returning to step 773, if the weight loss exceeds the weight loss trajectory, the method may jump to step 766 described above or continue on to step 774 described below.

If the weight loss is determined to be on track, or optionally exceeding the acceptable weight loss trajectory, the method proceeds to step 774 to check if the weight loss has plateaued, which is an indication that the third phase of the protocol should commence. The method may check if the patient weight loss data indicates that a rate of weight loss has been below a threshold weight loss rate for a period of time exceeding a stability time threshold. The stability time threshold may comprise a plurality of weeks such as 4 weeks, 8 weeks or 13 weeks.

If the weight loss has not plateaued, indicating the patient is on track and progressing through the progressive weight loss phase, the method may proceed to optional step 759 and recommend initiating or adjusting (and indicating) a physical activity regimen. This step may proceed in the same way as described above for identical step 659 of FIG. 6. As the weight loss phase progresses, the method advantageously supports the embedding of a new lifestyle of reduced calorie intake and regular exercise that will support the patient when the drug therapy is reduced or withdrawn. Following step 759 the method proceeds to step 740 for further iteration. The progressive weight loss phase may also recommend introducing, or increasing a level of, a physical activity regimen at other points in the method of FIG. 7 (not illustrated). The physical activity regimen may be utilised as an extra lever to encourage compliance and or weight loss. For example, if the method determines that the weight loss is less than the acceptable weight loss trajectory at step 773, the method may recommend introducing or increasing an intensity of the physical activity regimen in response before returning to step 740. Increasing physical activity can improve patient mood and/or increase the basal metabolic rate thereby increasing the number of calories burned.

If the weight loss has plateaued, the method may proceed to optional step 776 and check if the target weight has been reached (within an acceptance threshold). If the target weight has been achieved the method may proceed to step 778 and indicate/recommend starting the weight maintenance phase. If the target weight has not been achieved, the method may proceed to step 780 and reduce (and indicate) the calorie intake allowance before returning to step 740 for a further iteration. As weight is lost, as well as an increase in homeostatic drive to revert to the previous weight, or an intermediary weight, the basal metabolic rate may also decrease, meaning the total calorie requirement for steady state becomes lower than baseline. Therefore, if further weight loss is desired, an additional calorie restriction can be recommended at step 780 to provide sufficient hunger suppression. On subsequent iterations, the method may increase (and indicate) the incretin drug dosage at step 772 to address any drop in satiety resulting from the increased calorie restriction from step 780. In this way, the further calorie restriction may be accompanied with an increase in incretin drug dosage. However, the method may determine that the patient is unable to adhere to the new calorie intake allowance, for example by reviewing the patient progress data or because they are already on the maximum incretin dosage. In such circumstance, the method may indicate an increase to the target weight such that step 776 is satisfied and the patient can commence the weight maintenance phase. In some examples, a clinician may adjust the target weight at step 746.

Returning to step 774, in some examples, if the weight has plateaued, the method may proceed straight to step 778, regardless of whether the patient weight has fallen to the target weight. In this way, the method can support reaching a realistic sustainable weight loss for the patient before commencing the maintenance and withdrawal phases.

Although not illustrated in FIG. 7, the method may continue to monitor side effects during the progressive weight loss phase, for example in the same way as described above in relation to FIG. 6. This may be particularly important following a recommended incretin drug dosage increase at step 772.

The progressive weight loss phase of FIG. 7 focusses on monitoring: (i) patient weight loss to ensure weight loss is on track towards the target weight; and (ii) the patient satiety score to ensure that the patient adherence to the restricted calorie allowance is maintained. The method continues to help embed a healthy lifestyle/behaviour in the patient including a restricted (and healthy) calorie intake and a physical activity regimen. Once a plateaued weight is achieved, ideally at the target weight, the method may proceed to the weight maintenance phase.

Weight Maintenance Phase

As weight loss approaches plateau, typically occurring around week 44 to 46 since treatment onset, phase three is entered in which calorie levels are indicated to maintain a steady state of weight, facilitated by indication of the lowest incretin drug dosage that sufficiently controls hunger.

Figure 8:
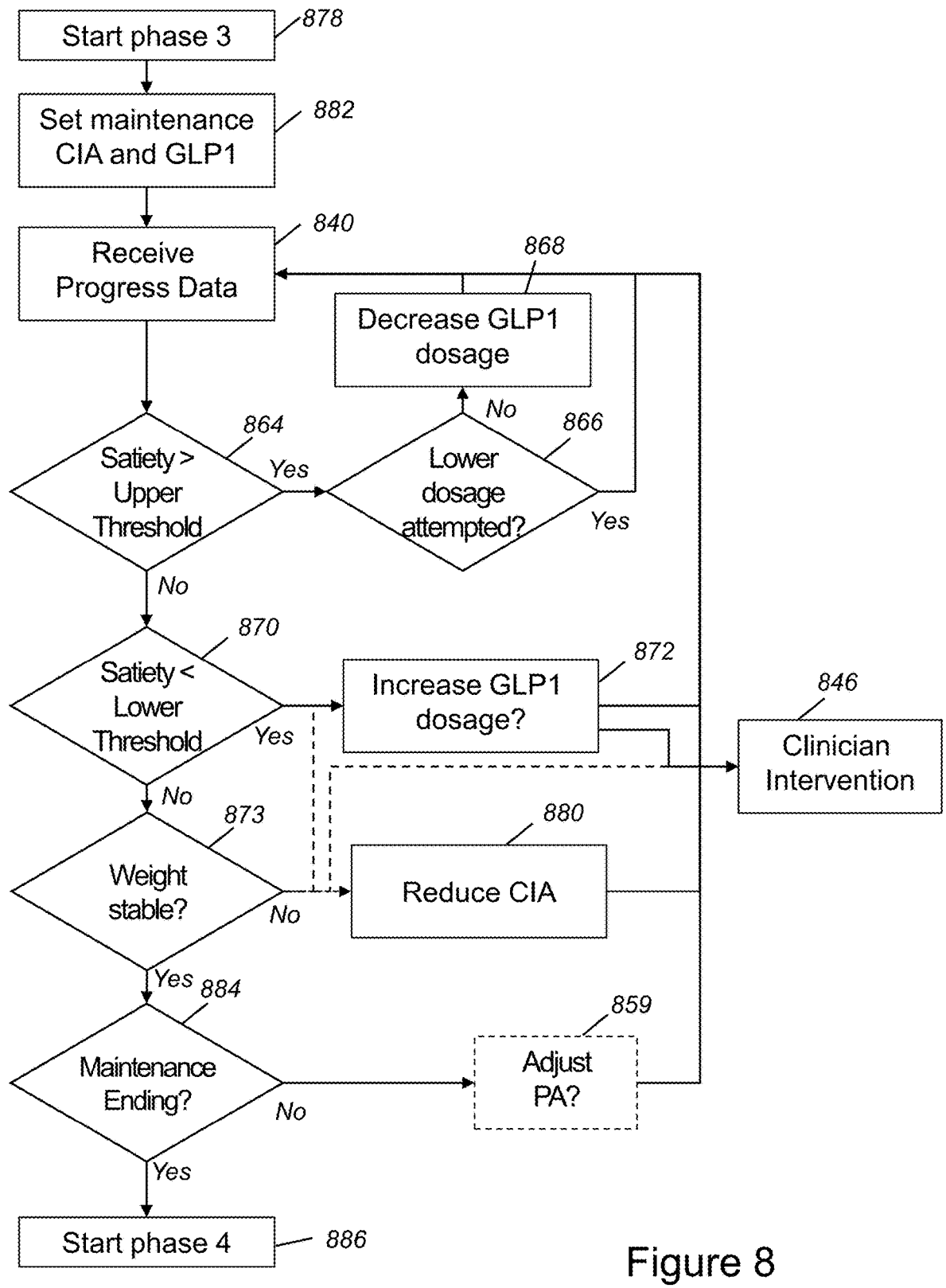
FIG. 8 illustrates a method of achieving a stable co-therapy regimen for the weight maintenance phase according to an embodiment of the present disclosure.

FIG. 8 illustrates a method of achieving a stable co-therapy regimen for the weight maintenance phase according to an embodiment of the present disclosure. The method has many identical steps to the method of the progressive weight loss phase described in relation to FIG. 7. Identical steps have been given the same numbering in the 800 series and may not be explicitly described again here.

Following the start of the weight maintenance phase at step 878, the method proceeds to step 882 to set (and indicate) a maintenance calorie intake regimen. As the patient is moving from a phase of weight loss to a phase of weight maintenance, the calorie intake allowance may be increased. The method may also set (and indicate) a reduced incretin drug dosage to accompany the increased calorie intake allowance because the increased calorie intake will naturally improve the patient satiety score.

At this stage, the method may also set a maintenance weight, which may be the same as, or a proportion higher, than the target weight or the weight achieved at plateau.

The method proceeds to step 840 to receive progress data on an iterative and periodic basis. The period of the iteration may be the same as the first phase and/or the second phase or may be longer because the incretin drug dosage and calorie intake regimens are more stable. Steps 864 to 872 operate in the same way as described above in that the patient satiety score is maintained within an optimal range at the minimum incretin drug dosage that provides hunger suppression sufficient for weight maintenance.

Picking up at step 873, if the patient satiety score is not less than the second lower satiety threshold, the method proceeds to step 873 to check if the patient weight is stable. For example, the method may check that the patient weight is within a threshold range, such a threshold range around the target weight. If the patient weight is increasing outside the threshold range, in other words the patient weight has started to increase again, the method may also, as part of step 873, determine if the calorie intake data represents a calorie intake less than or equal to the calorie intake allowance to ensure the patient is complying with the calorie intake regimen. The method may also comprise checking activity data to determine if the patient is adhering to a physical activity regimen. If the patient is complying with the calorie intake regimen (and optionally the physical activity regimen), the method may proceed to step 880 and reduce (and indicate) the calorie intake allowance before returning to step 840. If the patient is not complying with the calorie intake regimen (and optionally the physical activity regimen), the method may proceed to step 872 to increase (and indicate) the incretin drug dosage to improve patient satiety or proceed to step 846 and seek clinician intervention to address the compliance issues. Returning to step 873, if the patient weight is within the threshold range, the method may proceed to step 884.

At step 884, the method determines if the patient is at the end of the weight maintenance phase. The method may determine this in a number of ways. For example, the method may determine that the patient is at the end of the weight maintenance phase if a remaining time of the treatment period is less than a withdrawal phase minimum duration. For example, the withdrawal phase minimum duration may comprise a time between two months and 12 months that is set aside for weaning the patient off the incretin drug therapy or down to a chronic maintenance dose. The method may also determine that the patient is at the end of the weight loss maintenance period if the incretin drug dosage has decreased from the incretin drug dosage set in step 882 by a threshold amount. If the patient is at the end of the maintenance period, the method may indicate proceeding to step 886 to start the drug withdrawal phase. Otherwise the method proceeds to optional step 859 before returning to step 408 for further iterations. Optional step 427 may operate in the same way as described above for steps 227 and 327 of FIGS. 2 and 3. The physical activity regimen in the maintenance phase may include strength or muscle building routines to rebalance fat mass and lean mass to protect against the loss of lean mass during the weight loss treatment. Altering the ratio of fat mass and lean mass to favour lean mass can also raise the Basal metabolic rate (BMR), slowing weight regain and improving the prospects for successful drug withdrawal, and permanent weight loss and lifestyle change. The weight maintenance phase may also recommend introducing, or increasing an intensity level of, a physical activity regimen at other points in the method of FIG. 8 (not illustrated). The physical activity regimen may be utilised as an extra lever to encourage compliance and or weight loss. For example, if the method determines that the patient weight loss has started to creep up again at step 873, the method may recommend introducing or increasing an intensity of the physical activity regimen in response before returning to step 840. Increasing physical activity can improve patient mood and/or increase the basal metabolic rate thereby increasing the number of calories burned.

Although not illustrated in FIG. 8, the method may continue to monitor side effects during the weight maintenance phase, for example in the same way as described above in relation to FIG. 6. This may be particularly important following an incretin drug dosage increase at step 872.

The weight maintenance phase of FIG. 8 helps establish a patient stable weight while continuing to help embed a healthier lifestyle in the form of a recommended reduced calorie intake and regular physical activity. By the end of the maintenance phase, the method can help establish the healthier lifestyle as a patient habit. Eating patterns can be both environment and habit dependent. Therefore, if there is a successful period of enacting a new eating pattern, this may become easier to sustain, independent of any effect of the GLP1 or intrinsic dietary change motivation. Furthermore, the obesogenic environment may have also changed as a result, for example, with different foods now filling the cupboards, skills acquired in preparing different sorts of meals and a different structure to daily activities including the physical activity regimen. Establishing the healthier lifestyle as a patient habit can provide optimal preparation for the withdrawal or reduction in the incretin drug dosage in the drug withdrawal phase. Such habit forming can be supported by the method providing education and lifestyle modules as described below.

Drug Withdrawal Phase

During the drug withdrawal phase, the incretin pathway drug is gradually withdrawn, monitoring satiety levels and thus risk of relapse. In response to weight increase or satiety decrease and calorie rise, the method may determine and indicate either a short course of minimal dose GLP1 to re-establish desired behaviours, or a chronic maintenance dose.

Figure 9:
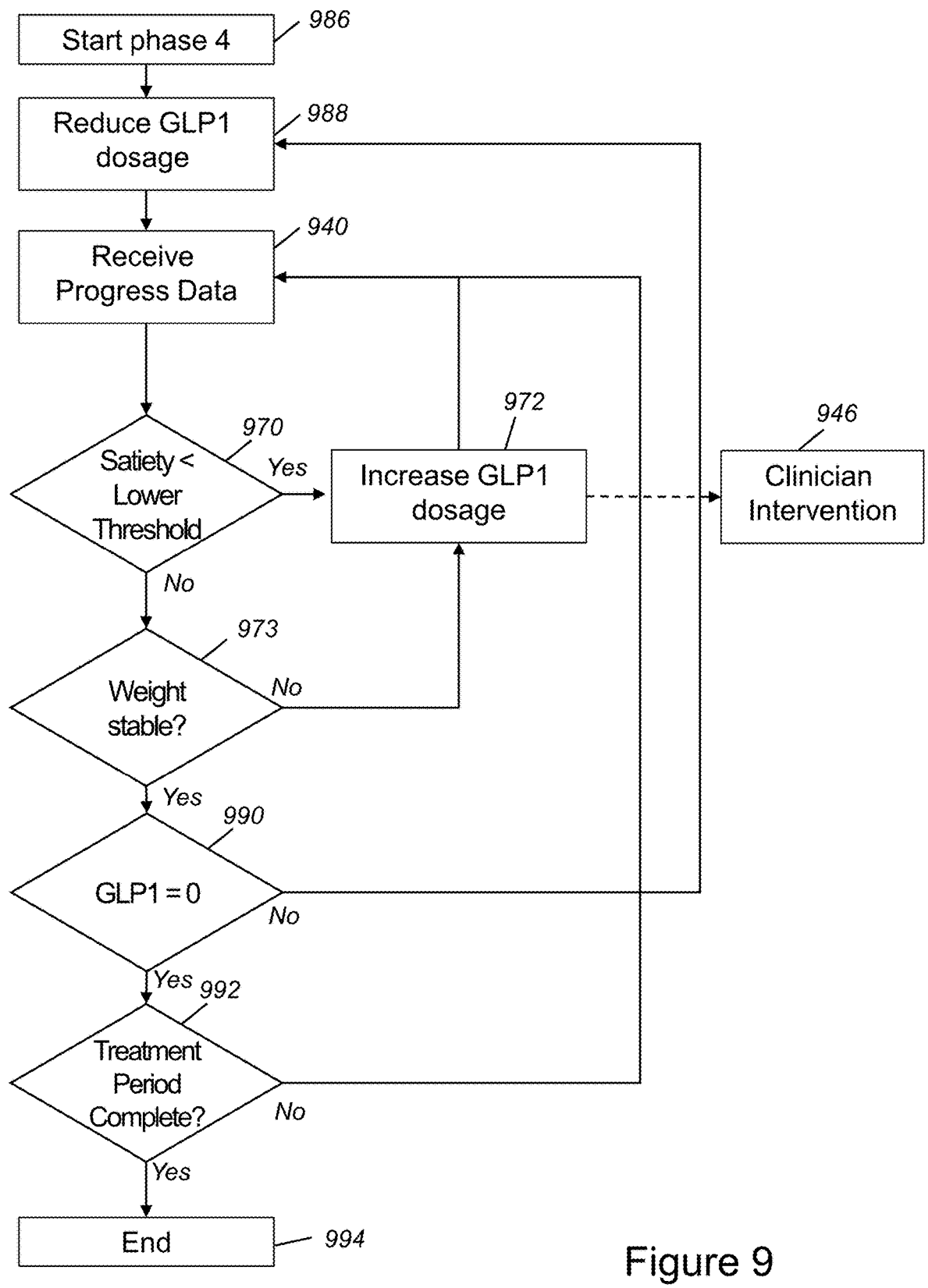
FIG. 9 illustrates a method of withdrawing GLP1 agonist from a co-therapy regimen for the drug withdrawal phase according to an embodiment of the present disclosure.

FIG. 9 illustrates a method of withdrawing the incretin pathway drug from a co-therapy regimen for the drug withdrawal phase according to an embodiment of the present disclosure.

Following the start of the drug withdrawal phase at step 986, the method proceeds to step 988 and decreases (and indicates) the incretin drug dosage. Decreasing the incretin drug dosage may comprise reducing a dosage amount or reducing a dosage frequency of the incretin pathway drug. The method proceeds to step 940 to receive patient progress data, in the same way as described above for the other phases.

At step 970, the method determines if the patient satiety score is less than a third lower satiety threshold. The third lower satiety threshold may indicate a risk of patient relapse to gaining weight and exceeding the calorie allowance. The third lower satiety threshold may be the same as the first and/or second lower satiety threshold. If the patient satiety score is less than the third lower satiety threshold the method proceeds to step 972 and increases (and indicates) the incretin drug dosage. The increase may be an increment back to the most recent higher dosage or, if the low satiety persistently returns every time the dosage is lowered towards zero, to a chronic maintenance incretin drug dosage. The method may optionally seek clinician intervention at step 946. The clinician may recommend complementary therapy such as surgery, or additional drugs using a different mechanism of action such as Phentermine/topiramate. The clinician may also recommend that the patient is transferred back to any of phases 1 to 3.

Returning to step 970, if the patient satiety score is greater than the third lower satiety threshold, the method may proceed to step 973 to check if the patient weight is stable. For example, the method may check that the patient weight is within a threshold range, such as a threshold range around the target weight. If the patient weight is increasing outside the threshold range, in other words the patient weight has started to increase again, the method may proceed to step 972 to increase (and indicate) the incretin drug dosage and improve patient satiety. Returning to step 973, if the patient weight is within the threshold range, the method may proceed to step 990.

At step 990, the method checks if the current incretin drug dosage is zero. If not, the method returns to step 988 and reduces (and indicates) the dosage further. In some examples, step 990 may also include checking if a time since the last dosage change is greater than a drug effect time. If the time is greater, the method may proceed to step 988, otherwise the method may return to step 940. In this way, the method avoids reducing the drug dosage too rapidly before the patient experiences the resulting reduction in satiety effect. If the incretin drug dosage is already zero, the method proceeds to step 992 to check if the treatment period is complete. If so, the method ends at step 994. If not the method returns to step 940 for further iteration, optionally via a physical activity regimen adjustment and indication (not shown) similar to that described at steps 659, 759 and 859.

In some jurisdictions, some incretin pathway drugs may be prescribed with a maximum treatment period, for example two years. In other jurisdictions, such as the USA, there is no restriction, however, having a finite treatment period can still save cost and end any side effects. The drug withdrawal phase can be particularly advantageous for patients who achieve weight targets within the 44-60 weeks as the remainder of the two-year approved prescription period can be used for the drug withdrawal phase. The drug withdrawal phase can flexibly assist with weight loss maintenance transition, such as a slow, step-wise reduction in dose or for relapse prevention, re-escalating the incretin drug dosage to catch and attenuate weight gain while further lifestyle support can be provided to assist the patient with the transition back to weight maintenance.

In some examples, the weight maintenance phase (FIG. 8) and the drug withdrawal phase (FIG. 9) may be combined into a single weight maintenance phase. For example, the outer loop 988 and 990 of FIG. 9 can be introduced into FIG. 8 to support controlled withdrawal of the drug. In such examples, a further phase may monitor the patient after drug withdrawal and recommend episodic bursts or a chronic prescription of incretin drug treatment and/or lifestyle education to address any relapse/weight gain above the target weight.

Lifestyle Education

Successful weight maintenance can be extremely challenging for the patient and suitable clinical service resources may often not be available or readily accessible. Research has shown that successful weight maintenance requires the individual to be equipped with knowledge, strategies, techniques and resources in advance of the weight maintenance programme. The disclosed method may incorporate education and training for patients to support their behavioural change throughout the co-therapy and the transitions between phases. In particular, the method may deliver lifestyle education via the patient electronic device, in the form of videos, slideshows, podcasts, forum and buddy support, interactive modules etc. The education modules may provide one or more of: dietary education, including food theory, cooking skills; physical activity/exercise education; mindfulness education for improving mood, improving motivation, reducing stress, reducing anxiety etc; education on improving the patients environment to promote healthy lifestyle and reduce calorie consumption triggers; and education on the treatment itself, such as an explanation of how the treatment will evolve, what to expect and how to address side effects.

The disclosed methods may introduce these education and lifestyle modules at any point during the co-therapy treatment. For example, the method may provide one or more education and lifestyle modules during the initial treatment titration phase when patient motivation for change may be high. The method may also provide one or more modules in accordance with an indicated adjustment to the co-therapy regimen, for example provide the physical activity education at or prior to any of steps 659, 759 or 859 of the respective FIGS. 6 to 8. The method may also provide one or more modules in response to the assessment of patient progress data. For example: side effect education may provided in concordance with steps 642 and 644; dietary education may be provided with steps 650, 654, 662, 770, 880, 972; and mindfulness education may be provided in response to a low motivation score indicated by the patient progress data at steps 640, 740, 840 and 940.

As one example, a side effect education module may reassure a patient about the potential for waning side effects. Patient studies indicate that reported nausea with GLP1 drugs drops with increased duration of any particular dose when maintained at that level. This adaptation may result from changes in patient physiology, but may also result from behavioural adaptations that the patient may undertake, such as eating smaller meals with, if necessary, increased frequency. The method may provide the side effect education module for educating the patient on such tolerance build up and/or providing advice to reduce the effects of nausea, prior to indicating a dosage reduction at step 648.

The method may provide a plurality of lifestyle modules prior to the drug withdrawal phase to help embed the behavioural and lifestyle change in the patient that will complement the calorie reduction and physical activity regimen and maximise the prospects for successful drug withdrawal.

The success of weight loss and weight maintenance may also be strongly influenced by behaviours of individuals close to the patient and the food environment within which they live. Although not shown, the method may engage with other individuals of importance to achieving weight loss or maintaining weight loss, such as equipping such individuals to support the patient via education, strategies, techniques, behaviours and environmental change.

Although the above examples is described in relation to a co-therapy comprising a single incretin pathway drug and a behavioural regimen, it will be appreciated that other examples may include more than one incretin pathway drug and/or one or more additional obesity treatment drugs. For example, an the co-therapy may comprise an additional obesity treatment drug such as metformin or topiramate. In some examples, the method may comprise setting, determining and/or adjusting the dosages of a plurality of obesity treatment drugs in response to the patient data. In some examples, the method may comprise setting, determining and/or adjusting the dosages of a plurality of obesity treatment drugs in response to the patient data in the absence of setting the behavioural regimen, which may be provided independently.

Approval Mechanisms

Throughout the described methods, any recommended adjustment to the co-therapy, particularly recommended changes to the GLP1 dosage may be subject to patient and/or HCP approval. For example, the method may comprise seeking patient approval for a recommended drug dosage change. For example, a prompt may be provided on the patient electronic device. If the patient does not indicate a willingness to proceed, the method may comprise maintaining the current drug dosage. If the patient indicates a willingness to proceed, the method may proceed to indicate, and/or instruct administration of, the recommended dosage change.

Other Example Implementations

Figure 10:
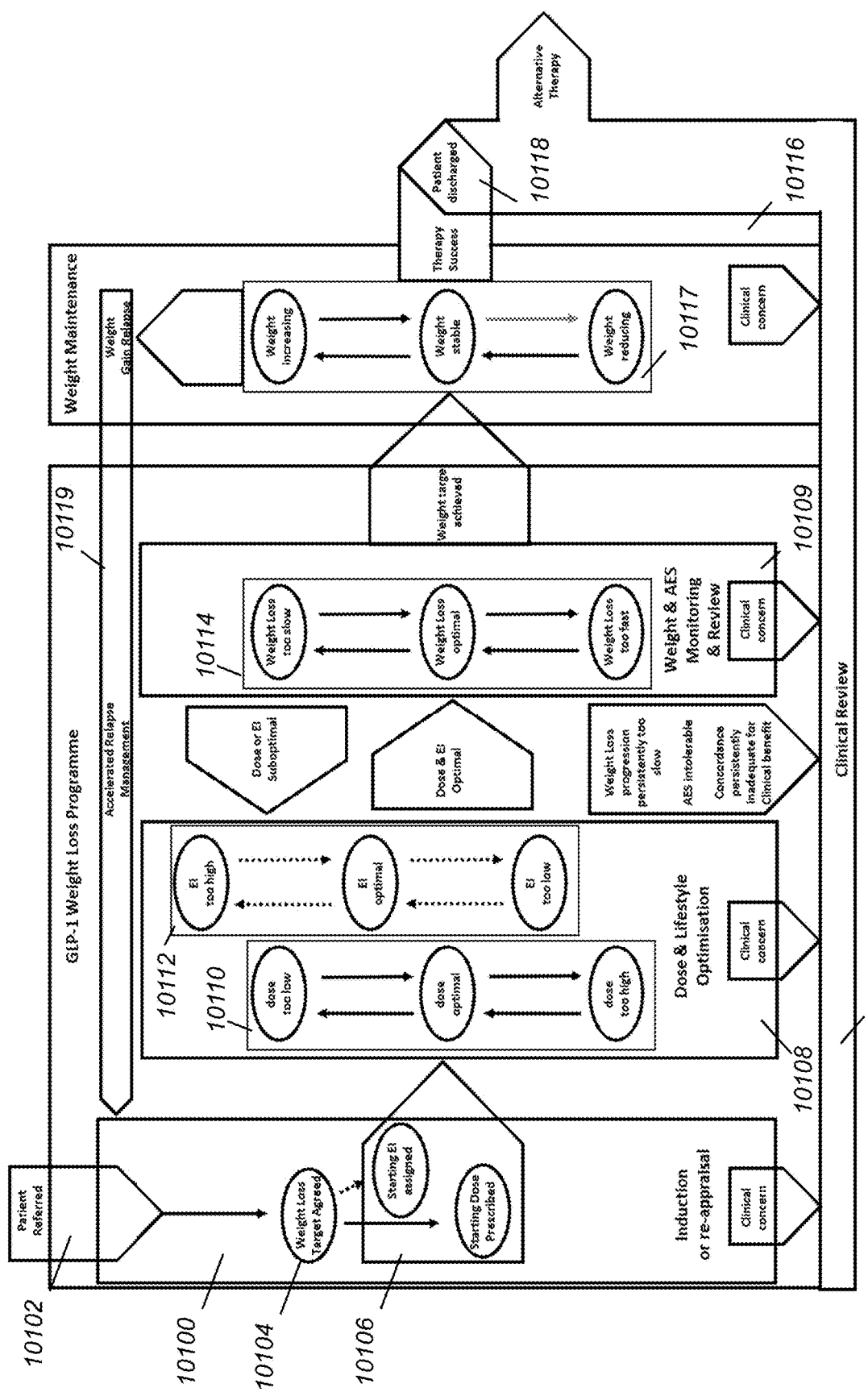
FIG. 10 illustrates a state diagram for the incretin drug co-therapy according to an embodiment of the present disclosure.

FIG. 10 illustrates a state diagram for the incretin drug co-therapy according to an embodiment of the present disclosure. In this example the incretin pathway drug is a GLP1 agonist.

In an initialisation phase 10100, after referral 10102, the patient and HCP agree a target weight 10104. The method proceeds to step 10106 and sets and indicates an initial GLP1 dosage and an initial calorie intake regimen (labelled EI—energy intake) as described above in relation to FIG. 6.

After setting the initial regimens, the method proceeds to a weight loss phase comprising a treatment titration routine 10108 and a progress monitoring routine 10109. The weight loss phase may comprise the Initial Treatment Titration Phase and the progressive weight loss phases described above. During the weight loss phase, the method reviews patient progress data including weight loss data 10114 and side effect data (not shown) in the progress monitoring routine 10109 and updates 10110 and indicates the incretin drug dosage (up, down, maintain) and updates 10112 and indicates the calorie intake regimen (up, down maintain), if the weight loss or reported side effects are suboptimal.

Following the weight loss phase, the method proceeds to a weight maintenance phase 10116 if the target weight has been achieved. The method continues to monitor 10117 patient weight during the weight maintenance phase and if the weight remains optimal, the patient is discharged 101118 after expiry of the treatment duration. If the patient weight is unstable, for example the weight increases, the method may return 10119 the patient to an earlier phase.

Throughout the process, the patient is monitored for HCP referral. For example, if weight loss progression is too slow, side effects are intolerable or patient concordance with the co-therapy (particularly the calorie intake regimen) is persistently inadequate, the method may refer the patient for clinical review 10120. HCP input may also be sought to review progress, for example at the periodic time points corresponding to the weight loss milestones, or approve recommended/indicated adjustments to the co-therapy components.

Figure 11:
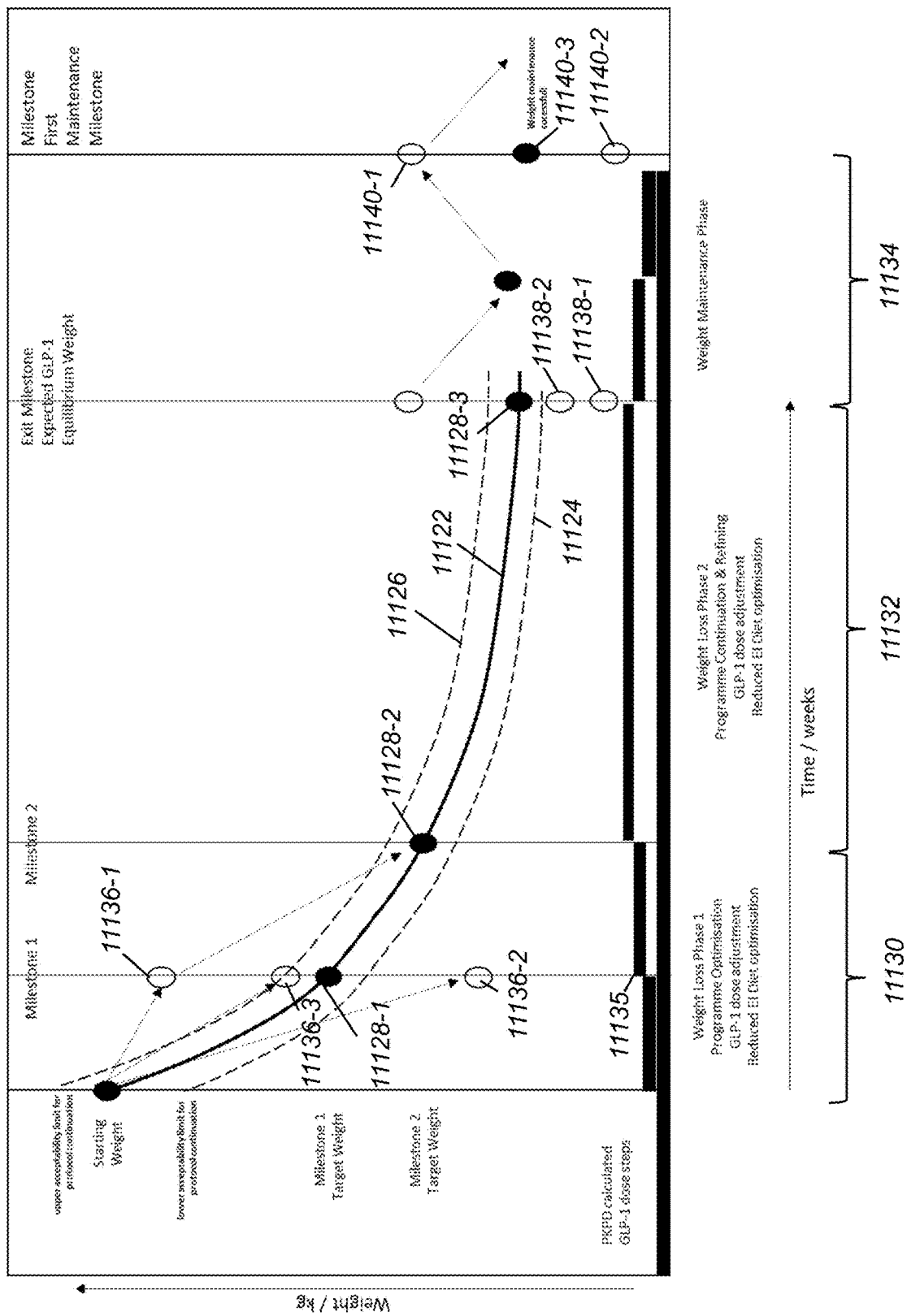
FIG. 11 illustrates the phased weight loss co-therapy in relation to an expected weight loss trajectory according to an embodiment of the present disclosure.

FIG. 11 illustrates the phased weight loss co-therapy in relation to an expected weight loss trajectory 11122 according to an embodiment of the present disclosure. The weight loss expectation range (or acceptable weight loss trajectory) including the upper weight loss trajectory 11124 and the lower weight loss trajectory 11126 is shown surrounding the weight loss trajectory 11122. A series of weight loss milestones 11128-1, 11128-2, 11128-3 can be seen on the expected weight loss trajectory 11122.

The expected weight loss trajectory 11122 is plotted against time and divided into the initial treatment titration phase 11130, the progressive weight loss phase 11132 and the treatment maintenance phase 11134. An incretin drug dosage (regimen) 11135 is shown as a stepped introduction and withdrawal across the three phases. In this example the incretin pathway drug is a GLP1 agonist.

Progress data indicating different patient response trajectories can be seen at some of the weight loss milestones to exemplify the method response. For example, at a time corresponding to the first weight loss milestone 11128-1, the method may receive first progress data 11136-1 for a first patient. The first progress data 11136-1 illustrates a weight loss that is less than the lower weight loss trajectory 11126. This may be indicative of: poor patient concordance with the drug dosage regimen (e.g. due to side effects) or the calorie intake regimen (the exact cause may be identified by specific progress data (calorie intake data etc)). The method may respond to the underperformance in weight loss by: increasing (and indicating) the drug dosage (e.g. step 654 of FIG. 6 or 772 of FIG. 7); reducing (and indicating) the drug dosage to reduce side effects (e.g. step 648 of FIG. 6); address poor calorie intake concordance (e.g. by providing an education model, recommending alternative diet plans, or seeking HCP input and potentially aborting treatment). The method can help bring the patient weight loss back within the acceptable weight loss trajectory.

As a second example, at a time corresponding to the first weight loss milestone 11128-1, the method may receive first progress data 11136-2 for a second patient. The first progress data 11136-2 illustrates a weight loss that exceeds the upper weight loss trajectory 11124. The method may assess whether the excessive weight loss is a risk to health (for example if the excessive weight loss may affect diabetes treatment). The method may respond by: maintaining the co-therapy regimen and continuing; reducing or eliminating (and indicating) the drug dosage (e.g. step 662 or 768); reducing (and indicating) the calorie intake allowance further until at target; or transitioning early to the maintenance phase 11134.

A third example at a time corresponding to the first weight loss milestone 11128-1, the method may receive first progress data 11136-3 for a third patient. The first progress data 11136-3 indicates weight loss is on track within the acceptable weight loss trajectory and the co-therapy regimen is maintained.

Patient progress data 11138-1, 11138-2 received at a time corresponding to the third milestone 11128-3 that indicates weight loss exceeding the lower weight loss trajectory indicates that target weight loss has been achieved within a target time (e.g. 44-60 weeks) and the patient can transition to the weight maintenance phase 11134.

As a further example, the method receives further patient progress data 11140-1 for a first patient at the end of the weight maintenance phase 11134 and after drug withdrawal that indicates patient relapse and weight gain above the target weight. The method may respond by recommending re-establishment of the incretin drug therapy or an episodic pulse of drug treatment. The method may also recommend a reduction of the calorie intake allowance to promote weight loss back to target weight.

Further patient progress data 11140-2, 11140-3 for a second patient and a third patient indicates successful completion of the treatment program.

Patient Examples

Two patient examples are described with continuing reference to the protocol method of FIGS. 6 to 9.

An example case is Mary, a 46 year old Caucasian of height 160 cm and weight 130 kg, leading to a BMI of 50.8 kgm2. Her target weight is 70 kg. Whilst she would still be overweight with a BMI of 27.3, this would be transformative. The current estimated calorie intake is 2600. The method calculates and suggests a target calorie reduction of 900 calories less than baseline per day in order to reach the target weight. She commences the a co-therapy comprising GLP1 administration and during the first two weeks has high levels of hunger and continues to snack between meals, failing to achieve the required calorie restriction. Her motivation score is low. The method recommends/indicates lowering the calorie restriction to 100 calories drop from baseline (step 654) while the GLP1 dose is titrated upwards according to the initial GLP1 dosage regimen. As the GLP1 takes effect, satiety levels become consistently high on moving average, at which stage the method adjusts (and indicates) the calorie restriction to a more stringent calorie level of 500 calories less than baseline (Step 662). Satiety levels are maintained as GLP1 levels continue to increase according to the initial GLP1 dosage regimen and the method further adjusts (and indicates) the calorie intake regimen to a full 900 calorie restriction (step 662). The patient enters the progressive weight loss therapy with the maximum GLP1 dosage and the 900 calorie restriction. The weight gradually drops to 73 kg with no variation in GLP1 dosage or calorie restriction. As the weight loss plateaus out, the method titrates and indicates the GLP1 dosage downwards (step 988) until satiety levels begin to slip (step 970). The method then increases and indicates an increased GLP1 dosage to the most recent controlling dosage amount (step 962). This is maintained for a further three months before complete withdrawal. However, after six months, a major life event leads to food binging and previous bad habits returning. Step 973 recommends a reintroduction of GLP1 which is titrated up to a maintenance dose and continued for a further three months before withdrawing once more. At follow up one year later, weight remains steady.

Harold is a 50 year old male of height 1.86 m and weight 149 kg, giving him a BMI of 43.1. His desired weight is 86 kg, giving a BMI of 24.9, just within the normal range. He does not have access to any intense calorie restriction techniques such as food substitution and instead the method sets and indicates an initial 200 calorie per day restriction based on assessment of low motivation. However, satiety is high on the second scheduled step-up of the GLP1 dosage regimen and the method increases (and indicates) the calorie intake restriction to 400 calories per day deficit (step 662). A single further step up in GLP1 dose maintains the level of satiety. As his weight reaches 110 kg, his energy levels and body pains have altered, such that the method recommends introduction of an exercise (physical activity) regimen (step 759) which is gradually titrated up in proportion to the continuing decrease in his pains as a result of his weight loss and his increasing energy levels. The patient continues in the progressive weight loss phase with no change in GLP1 dosage or calorie restriction and weight continues to drop until a plateau of 94 kg. The method then recommends a further dose titration to allow a further calorie restriction by an extra 50 calories and then three months later a target weight of 86 kg is reached (combination of steps 776, 780, 770 and 772). The GLP1 is then withdrawn, but his calorie restriction slips to 200 calories as a result of lower levels of satiety. The method recommends reintroduction of the GLP1 (step 972) at the starting dose of 0.25, which allows re-establishment of the greater calorie restriction. Funding ultimately means this cannot be maintained and he ultimately has a long term calorie restriction delivering a weight of 94 kg.

FIGS. 5 to 11 and their associated description are merely exemplary and do not limit the scope of the invention which is defined by the appended claims. One or more steps may be optional. Furthermore, the instructions and/or flowchart steps can be executed in any order. Also, those skilled in the art will recognize that while one example set of instructions/method has been discussed, the material in this specification can be combined in a variety of ways to yield other examples as well, and are to be understood within a context provided by this detailed description.

In some example embodiments the set of instructions/method steps described above are implemented as functional and software instructions embodied as a set of executable instructions which are effected on a computer or machine which is programmed with and controlled by said executable instructions. Such instructions are loaded for execution on a processor (such as one or more CPUs). The term processor includes microprocessors, microcontrollers, processor modules or subsystems (including one or more microprocessors or microcontrollers), or other control or computing devices. A processor can refer to a single component or to plural components.

Diabetes Co-Therapy

A behavioural co-therapy including dietary, physical exercise or sleep intervention can support improvement in glycemic control. The use of CGM data and/or HbA1c for monitoring the progress of the GLP1 therapy can reinforce the behavioural regimen helping the patient to further improve glycemic control and potentially leading to remission of the type 2 diabetes.

The method may generate and indicate a behavioural regimen comprising dietary and/or physical activity intervention based on personalised patient data in the same way as described above for the obesity co-therapy.

Insufficient sleep duration and quality has been linked to the risk of obesity, insulin resistance and type 2 diabetes. The method may comprise generating a sleep regimen if the personalised patient data indicates a lack of sufficient duration or quality sleep. Such sleep data may be received by manual patient entry or from electronic devices such as smart watches that can monitor sleep quality.

Implementation

Figure 16:
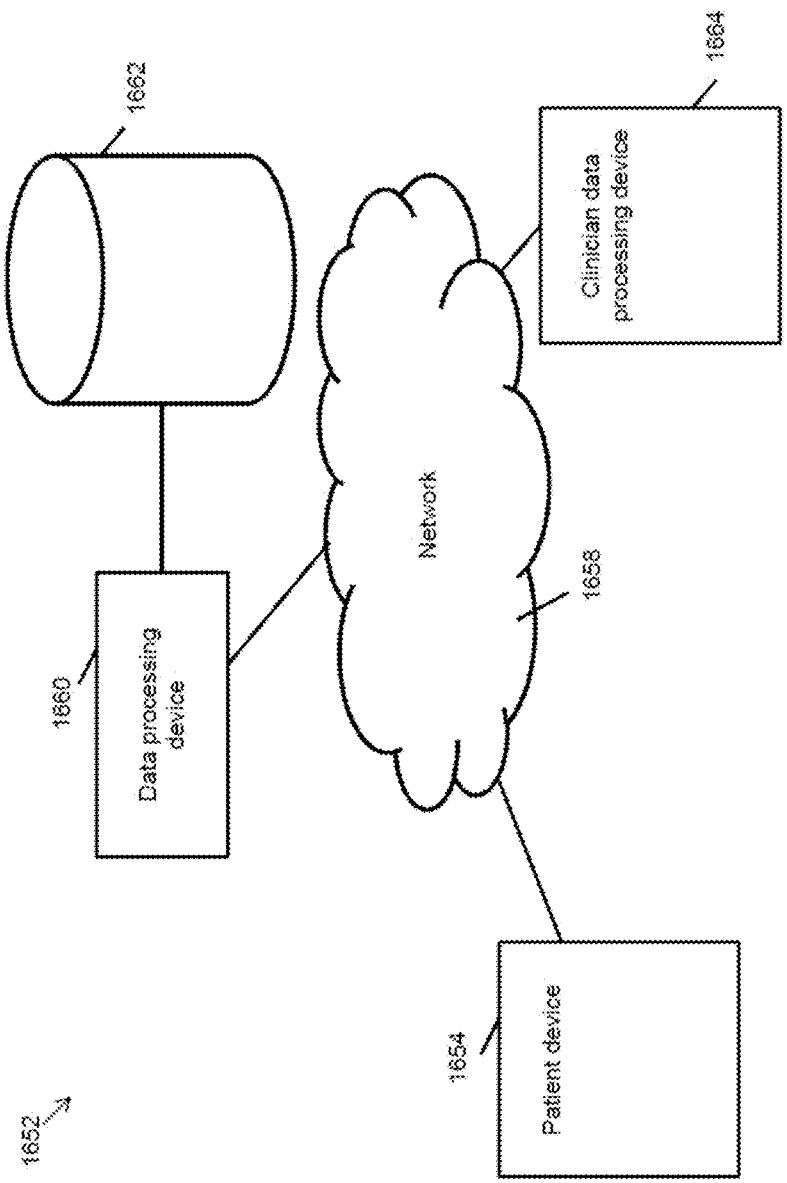
FIG. 16 illustrates a system suitable for carrying out any of the computer implemented methods described herein.

FIG. 16 illustrates a system suitable for carrying out an implementation of the digital therapy (also referred to herein as the digital app) and any of the computer implemented methods described herein. System 1652 includes a patient device 1654. The patient device 1654 may comprise one or more processors. The one or more processors may be configured to: receive the patient data; process the patient data with a dosage calculator to determine the dosage of an incretin pathway drug for administering to the patient; and indicate the dosage. The one or more processors may further be configured to: receive personalised patient data; set a calorie intake regimen based on the personalised patient data; and indicate the incretin pathway drug dosage and the calorie intake regimen.

In the illustrated embodiment, patient device 1654 is a smartphone. However, the invention is not limited in this respect and the patient device 1654 can take many other forms, including but not limited to a mobile telephone, a tablet computer, a desktop computer, a voice-activated computing system, a laptop, a gaming system, a vehicular computing system, a wearable device, a smart watch, a smart television, an internet of things device and a medicament-dispensing device.

The patient device 1654 may be configured to gather one or more parameters of the patient data. The patient data can be obtained via manual data entry using a human interface device of patient device 1654 and/or from a remote source via the network 1658.

The patient device 1654 may comprise a memory (not illustrated) for storing the patient data and/or outputs of the dosage calculator. Such data may also be stored on a database 1662 as networked or cloud-based data storage.

The patient device 1654 may have one or more applications (or apps) installed on a storage medium associated with the patient device (not shown). The one or more apps may be configured to perform any of the computer implemented methods disclosed herein. The one or more applications may be configured to assist the patient in providing the patient data and/or may include the dosage calculator for processing the patient data. The one or more applications may be downloaded from a network, for example from a website or an online application store.

In this example, the system 1654 further comprises a data processing device 1660 that is communicatively coupled to the patient device 1654 via the network 1658. In the illustrated embodiment network 1658 is the internet, but the invention is not limited in this respect and network 1658 could be any network that enables communication between patient device 1654 and data processing device 1660, such as a cellular network or a combination of the internet and a cellular network.

The data processing device 1660 may supplement the patient device 1654 and perform one or more steps of any of the computer implemented methods disclosed herein. For example, in some embodiments, the patient device 1654 may receive the patient data and provide the patient data to the data processing device 1660. The data processing device 1660 may then process the patient data with the dosage calculator to determine the dosage for administering to the patient. The data processing device 1660 may then provide the dosage to the patient device 1654 or a HCP device 1664 (also referred to as clinician device 1664) either or both of which may indicate the dosage. In this way, the data processing device 1660 provides networked, server based or cloud based, processing capability to the system for performing the computer implemented methods.

The data processing device 1660 may be coupled to the database 1662 that can store the patient data and/or the outputs of the dosage calculator.

In this example, the system 1652 includes a clinician data processing device 1664 that is communicatively coupled via network 1658 to the patient device 1654 and the data processing device 1660. The clinician data processing device 1664 may be broadly similar to patient device 1654, offering a similar set of functionality. Specifically, the clinician data processing device 1664 enables patient data to be collated or received. Clinician data processing device 1664 is contemplated as being physically located at a HCP's premises during its use, such as a clinic, a doctor's surgery, a pharmacy or any other healthcare institution, e.g. a hospital. Clinician data processing device 1664 may include one or more sensors, and/or be configured to control one or more separate sensors, which sensors are capable of gathering information about the patient, e.g. a blood pressure sensor.

It is also contemplated that clinician data processing device 1664 is typically used by a medically trained person with appropriate data security clearance, such that more advanced functionality may be available than via the patient device 1654. For example, the clinician data processing device 1664 may be able to access a medical history of the patient, generate a drug prescription for the patient, place an order for medication, etc. Access to functionality may be controlled by a security policy implemented by a local processor or data processing device 1660.

The data processing device 1660 and/or the clinician device 1664 may have an application installed that is compatible with or the same as the application installed on the patient device 1654.

It will be appreciated that the various steps of the computer implemented methods disclosed herein may be performed in any combination by any of the one or more processors in the patient device 1654, the data processing device 1660 and the clinician device 1664. For example, all steps may be performed by the clinician device 1664 which receives one or more parameters of the patient data locally, from the patient device 1654 or another remote device via the network 1658 and optionally via the data processing device 1660. In a further example, all steps may be performed in a networked back-end on data processing device 1660, with patient device 1654 and clinician device 1664 acting as human interfaces for gathering and indicating data. In a yet further example, all steps may be performed on patient device 1654 with clinician device 1664 merely gathering relevant data from the patient device 1654 for informing or directing the HCP.

It will also be appreciated that one or more of the components of the system 1652 could be omitted depending upon the application. For example, at a clinic setting, the disclosed computer implemented methods could be performed solely on the clinician device 1664. Alternatively, the methods could be performed solely on the patient device 1654 in a domestic setting.

The dosage calculator may be deployed to any of patient device 1654, data processing device 1660, and clinician device 1664 as a digital app. The digital app may indicate to the HCP a dose (starting dose, continuing dose or revised dose, timing of dose) for administering to a particular patient based on computed changes in drug levels to achieve a target end point.

It will be appreciated that any reference to "close to", "before", "shortly before", "after" "shortly after", "higher than", or "lower than", etc, can refer to the parameter in question being less than or greater than a threshold value, or between two threshold values, depending upon the context.

Annex

Individual characteristics modulate the plasma drug level. Overgaard et al [3] found effects from weight, sex, age, kidney function (described via GFR), race/ethnicity (Overgaard separates US spanish and 'english' heritage within 'ethnicity'), presence or absence of type 2 disabetes, water intake, as well as drug dosage and injection site. Contributions were modelled via the Cl parameter used to calculate 'ke'. All of the parameter values can be obtained from the Overgaard paper:

$$k_{ai} = \left[(k_{a,ref} - \theta_{ka,long,fast}) \cdot e^{-\theta_{T,fasting} \cdot (T_{fasting} - 30)} + \theta_{ka,long,fast}\right] \cdot \exp(\eta_{ka,i}) \quad (1)$$

$$CL_i = CL_{ref} \cdot E_{weight,CL} \cdot E_{T2D} \cdot \exp(\eta_{CL,i}) \quad (2)$$

$$Q_i = Q_{ref} \cdot E_{weight,CL} \cdot \exp(\eta_{CL,i}) \quad (3)$$

$$V_{c,i} = V_{c,ref} \cdot E_{weight,V} \cdot \exp(\eta_{V_c,i}) \quad (4)$$

$$V_{p,i} = V_{p,ref} \cdot E_{weight,V} \cdot \exp(\eta_{V_c,i}) \quad (5)$$

$$F_{ij} = F_{ref} \cdot E_{weight,F} \cdot E_{water,F} \cdot E_{fasting,F} \cdot \exp(\eta_{F,i} + \eta_{F,j}) \quad (6)$$

where $$E_{weight,CL} = \left(\frac{weight_i}{85\ kg}\right)^{\theta_{weight,CL}} \quad (7)$$

$$E_{weight,V} = \left(\frac{weight_i}{85\ kg}\right)^{\theta_{weight,V}} \quad (8)$$

$$E_{T2D} = (\theta_{T2D,CL})^{T2D} \quad (9)$$

$$E_{weight,F} = \left(\frac{weight_i}{85\ kg}\right)^{\theta_{weight,F}} \quad (10)$$

$$E_{water,F} = (\theta_{240\ mL})^{240\ mL} \quad (11)$$

$$E_{fasting,F} = \frac{1 - e^{-\theta_{T,fasting,F} \cdot T_{fasting}}}{1 - e^{-\theta_{T,fasting,F} \cdot 30}} \quad (12)$$

For the model used for FIGS. 4A to 4C, the following implementation was used:

$$E\_dose = (theta\_dose05\ mg) ** dose05\ mg$$

$$E\_weight = (WT/85.0) ** theta\_wt$$

$$E\_sex = (theta\_male) ** male$$

$$E\_age = ((theta\_age\_65\_75y) ** age\_65\_74y) *$$
$$((theta\_age\_GTE75y) ** ageGTE75y)$$

$$E\_GFR = ((theta\_GFR\_mild) ** GFR\_mild) *$$
$$((theta\_GFR\_moerate) ** GFR\_moderate) *$$
$$((theta\_GFR\_severe) ** GFR\_severe)$$

$$E\_race = ((theta\_BlackAfrAm) ** BlackAfrAm) *$$
$$((theta\_Asian) ** Asian) * ((theta\_Other) ** Other)$$

$$E\_ethnicity = ((theta\_Hispanic) ** Hispanic)$$

$$E\_inj\_site = ((theta\_Thigh) ** Thigh) * ((theta\_Upperarm) ** Upperarm)$$

with $$Cl = Cl\_type * E\_dose * E\_weight * E\_sex *$$
$$E\_age * E\_GFR * E\_race * E\_ethnicity * E\_inj\_site$$

$$V = V\_typ.$$

Compartment volume is held constant for population. Adjustments arising from age, race, weight, dose, sex etc are made via Cl.

REFERENCES

[1]: Wegovy FDA 215256ClinPharmR
[2]: Ozempic sc FDA 209637 Clin Pharm Review 2016
[3]: Overgaard R V, Delff P H, Petri K C C, Anderson T W, Flint A, Ingwersen S H. Population pharmacokinetics of semaglutide for type 2 diabetes. Diabetes Ther. 2019; 10:649-62
[4]: Semaglutide s.c. Once-Weekly in Type 2 Diabetes: A Population Pharmacokinetic Analysis. Carlsson Petri K C, Ingwersen S H, Flint A, Zacho J, Overgaard RV. Diabetes Ther. 2018 August; 9(4):1533-1547. doi: 10.1007/s13300-018-0458-5
[5]: Mounjaro FDA 215866ClinPharmR
[6]: Gerving, C., Lasater, R., Starling, J. et al. Predicting energy intake in adults who are dieting and exercising. *Int J Obes* 46, 2095-2101 (2022). https://doi.org/10.1038/s41366-022-01205-0
[7]: JANMAHASATIAN, S., DUFFULL, S. B., ASH, S., WARD, L. C., BYRNE, N. M. & GREEN, B. 2005. Quantification of lean bodyweight. Clin Pharmacokinet, 44, 1051-65.
[8]: Enebo L B, Berthelsen K K, Kankam M, Lund M T, Rubino D M, Satylganova A, Lau D C W. Safety, tolerability, pharmacokinetics, and pharmacodynamics of concomitant administration of multiple doses of cagrilintide with semaglutide 2.4 mg for weight management: a randomised, controlled, phase 1b trial. Lancet. 2021 May 8; 397(10286):1736-1748. doi: 10.1016/S0140-6736(21)00845-X. Epub 2021 Apr. 22. PMID: 33894838.

The invention claimed is:

1. A method for administering a dosage of Cagrisema to a patient for the treatment of obesity, the method comprising:
administering a dosage of Cagrisema to the patient, wherein the dosage of Cagrisema is determined by:
receiving patient data relating to a patient, wherein the patient data includes patient weight data; and
processing a target end point and the patient data including the patient weight data with a dosage calculator to calculate the dosage of Cagrisema for administering to the patient wherein the dosage calculator is derived from a pharmacokinetic, PK, model comprising a time-based differential equation model for modelling a dependence of a Cagrisema concentration in the patient as a function of patient data and dosage of Cagrisema,
wherein the target end point comprises one or more of:
a target weight loss; or
a target side effect level.

2. The method of claim 1, wherein the PK model comprises a personalised energy intake—total daily energy expenditure model.

3. The method of claim 1 comprising processing the patient weight data with the dosage calculator to determine an initial dosage for administering to the patient.

4. The method of claim 3, wherein the patient weight data includes an initial weight and a target weight and the method comprises processing the initial weight and the target weight with the dosage calculator to determine the initial dosage.

5. The method of claim 4, wherein processing the initial weight and the target weight with the dosage calculator to determine the dosage comprises:
setting a target drug concentration based on the initial weight and the target weight; and
determining the initial dosage based on the target drug concentration and the initial weight.

6. The method of claim 5, wherein the patient data further comprises one or more of: a patient age; a patient ethnicity; a patient gender; a patient diabetes history; a kidney function metric; a treatment purpose; a dosage route; a pharmacogenomic profile and a patient medication list, and wherein the method comprises determining the initial dosage based on the target drug concentration and the patient data.

7. The method of claim 1, wherein the method comprises:
setting a target drug concentration comprising an ideal therapeutic level; and
determining an initial dosage based on the target drug concentration and an initial weight.

8. The method of claim 1, wherein the patient data further comprises a patient side effect tolerance and the method comprises processing the patient side effect tolerance with the dosage calculator to determine an initial dosage.

9. The method of claim 8, wherein the method comprises:
processing the patient side effect tolerance and the patient data with the dosage calculator to obtain a target drug concentration that satisfies the patient side effect tolerance; and
processing the target drug concentration with the dosage calculator to determine the initial dosage.

10. The method of claim 9, wherein the dosage calculator comprises a side-effect calculator derived from a side effect model comprising a discrete-time Markov side effect model or an Emax exposure response side effect model.

11. The method of claim 1 further comprising:
receiving updated patient data including updated patient weight data; and
processing the updated patient data with the dosage calculator to determine an updated dosage; and
administering the updated dosage.

12. The method of claim 11, wherein processing the updated patient data with the dosage calculator to determine an updated dosage comprises one or more of:
   increasing the dosage if the updated weight data indicates a weight loss is less than a lower weight loss threshold; and
   reducing the dosage if the updated weight data indicates a weight loss greater than an upper weight loss threshold.

13. The method of claim 11, wherein the updated patient data includes patient satiety data and processing the updated patient data with the dosage calculator to determine an updated dosage comprises one or more of:
   reducing the dosage if the patient satiety data indicates a patient satiety greater than a first patient satiety threshold; and
   increasing the dosage if the patient satiety data indicates a patient satiety less than a second patient satiety threshold.

14. The method of claim 11, wherein the updated patient data includes reported side effect data and wherein processing the updated patient data with the dosage calculator to determine an updated dosage comprises reducing the dosage if the reported side effect data satisfies one or more side effect severity thresholds.

15. The method of claim 11, wherein the updated patient data includes a patient metabolism metric from a physiological test result and the method comprises updating the dosage calculator based on the patient metabolism metric.

16. The method of claim 1, wherein the dosage calculator comprises a machine learning algorithm trained using a PK model.

17. The method of claim 1, wherein processing the patient data with the dosage calculator to determine the dosage of Cagrisema for administering to the patient comprises:
   processing the patient data with the dosage calculator to determine an ideal dosage regime; and
   selecting the dosage for administering to the patient from a selection of available dosage regimes based on the ideal dosage regime.

18. The method of claim 17, wherein the selection of available dosage regimes comprise:
   dosage amounts of subcutaneous Cagrisema comprising any integer multiple of 0.05 mg from 0.05 mg up to 10.00 mg.

19. The method of claim 17, wherein the selection of available dosage regimes comprise dosage amounts comprising one or more of: 0.25, 0.5, 1.0, 1.7 2.0, 2.4, 3.4 and 4.8 mg of subcutaneous Cagrisema for administration once weekly.

20. The method of claim 1, comprising processing the patient data with the dosage calculator to determine one or more of: a dosage amount; and a dosage frequency.

21. The method of claim 20, comprising processing the patient data with the dosage calculator to determine:
   a personalised dosage amount for a fixed dosage frequency;
   a personalised dosage frequency for a fixed dosage amount; or
   a personalised dosage amount and a personalised dosage frequency.

22. The method of claim 1 further comprising:
   setting a calorie intake regimen based on the patient data; and
   indicating the calorie intake regimen.

23. The method of claim 22, wherein the dosage comprises an initial dosage and the method comprises:
   setting the calorie intake regimen based on an initial weight and a target weight of the patient weight data; or
   determining an expected energy intake trajectory based on the initial dosage; and
   setting the calorie intake regimen based on the expected energy intake trajectory.

24. A method for treating a patient for obesity, the method comprising:
   receiving patient data relating to the patient, wherein the patient data includes patient weight data;
   processing a target end point and the patient data including the patient weight data with a dosage calculator to calculate an effective dosage of Cagrisema to administer to the patient, wherein the dosage calculator is derived from a pharmacokinetic, PK, model comprising a time-based differential equation model for modelling a dependence of a Cagrisema concentration in the patient as a function of patient data and dosage of Cagrisema, wherein the target end point comprises one or more of:
   a target weight loss; or
   a target side effect level; and
   administering the calculated effective dosage of Cagrisema to the patient to treat the patient for obesity.

* * * * *